US012570757B2

(12) United States Patent
Alberts et al.

(10) Patent No.: US 12,570,757 B2
(45) Date of Patent: Mar. 10, 2026

(54) ANTIBODIES AGAINST THE POLIOVIRUS RECEPTOR (PVR) AND USES THEREOF

(71) Applicant: NECTIN THERAPEUTICS LTD., Jerusalem (IL)

(72) Inventors: Philipp Alberts, Amsterdam (NL); Arif Jetha, Toronto (CA); Johan Fransson, San Diego, CA (US); Yazen Jmeian, New Haven, CT (US); Joanne Hulme, Toronto (CA); Pinchas Tsukerman, Jerusalem (IL)

(73) Assignee: NECTIN THERAPEUTICS LTD., Jerusalem (IL)

( * ) Notice: Subject to any disclaimer, the term of this patent is extended or adjusted under 35 U.S.C. 154(b) by 1018 days.

(21) Appl. No.: 17/764,373

(22) PCT Filed: Oct. 7, 2020

(86) PCT No.: PCT/IL2020/051082
§ 371 (c)(1),
(2) Date: Mar. 28, 2022

(87) PCT Pub. No.: WO2021/070181
PCT Pub. Date: Apr. 15, 2021

(65) Prior Publication Data
US 2022/0372161 A1      Nov. 24, 2022

Related U.S. Application Data

(60) Provisional application No. 62/912,534, filed on Oct. 8, 2019.

(51) Int. Cl.
| | |
|---|---|
| *C07K 16/28* | (2006.01) |
| *A61K 39/00* | (2006.01) |
| *A61P 31/14* | (2006.01) |
| *A61P 35/02* | (2006.01) |
| *A61P 37/02* | (2006.01) |

(52) U.S. Cl.
CPC .......... *C07K 16/2896* (2013.01); *A61P 31/14* (2018.01); *A61P 35/02* (2018.01); *A61P 37/02* (2018.01); *A61K 2039/505* (2013.01); *C07K 2317/24* (2013.01); *C07K 2317/30* (2013.01); *C07K 2317/565* (2013.01); *C07K 2317/622* (2013.01); *C07K 2317/76* (2013.01); *C07K 2317/92* (2013.01)

(58) Field of Classification Search
CPC ........... C07K 16/2896; C07K 2317/24; C07K 2317/565; C07K 2317/622; C07K 2317/76; C07K 14/7051; A61P 35/00; C12N 2510/00
See application file for complete search history.

(56) References Cited

U.S. PATENT DOCUMENTS

| | | | |
|---|---|---|---|
| 3,791,932 | A | 2/1974 | Schuurs |
| 3,839,153 | A | 10/1974 | Schuurs |
| 3,850,578 | A | 11/1974 | McConnell |
| 3,850,752 | A | 11/1974 | Schuurs |
| 3,853,987 | A | 12/1974 | Dreyer |
| 3,867,517 | A | 2/1975 | Ling |
| 3,879,262 | A | 4/1975 | Schuurs |
| 3,901,654 | A | 8/1975 | Gross |
| 3,935,074 | A | 1/1976 | Rubenstein |
| 3,984,533 | A | 10/1976 | Uzgiris |
| 3,996,345 | A | 12/1976 | Ullman |
| 4,034,074 | A | 7/1977 | Miles |
| 4,036,945 | A | 7/1977 | Haber |
| 4,098,876 | A | 7/1978 | Piasio |
| 4,331,647 | A | 5/1982 | Goldenberg |
| 4,666,828 | A | 5/1987 | Gusella |
| 4,683,202 | A | 7/1987 | Mullis |
| 4,801,531 | A | 1/1989 | Frossard |
| 4,816,567 | A | 3/1989 | Cabilly |
| 4,879,219 | A | 11/1989 | Wands |
| 4,946,778 | A | 8/1990 | Ladner |
| 5,011,771 | A | 4/1991 | Bellet |
| 5,192,659 | A | 3/1993 | Simons |
| 5,225,539 | A | 7/1993 | Winter |
| 5,272,057 | A | 12/1993 | Smulson |
| 5,281,521 | A | 1/1994 | Trojanowski |
| 5,500,362 | A | 3/1996 | Robinson |
| 5,530,101 | A | 6/1996 | Queen |
| 5,545,806 | A | 8/1996 | Lonberg |
| 5,545,807 | A | 8/1996 | Surani |
| 5,569,825 | A | 10/1996 | Lonberg |

(Continued)

FOREIGN PATENT DOCUMENTS

| | | |
|---|---|---|
| CN | 109071666 A | 12/2018 |
| CN | 110256558 A | 9/2019 |

(Continued)

OTHER PUBLICATIONS

Caldas et al. Humanization of the anti-CD18 antibody 6.7: an unexpected effect of a framework residue in binding to antigen. Molecular Immunology 39 (2003) 941-952 (Year: 2003).*

(Continued)

*Primary Examiner* — Janet L Andres
*Assistant Examiner* — Brian Hartnett
(74) *Attorney, Agent, or Firm* — Rothwell, Figg, Ernst & Manbeck, P.C.

(57) ABSTRACT

The present invention provides humanized antibodies and antigen binding fragments thereof that bind to human poliovirus (PVR). The antibodies are useful in the treatment of tumors or cancers.

19 Claims, 25 Drawing Sheets
Specification includes a Sequence Listing.

(56) References Cited

U.S. PATENT DOCUMENTS

| 5,585,089 | A | 12/1996 | Queen |
|---|---|---|---|
| 5,624,821 | A | 4/1997 | Winter |
| 5,625,126 | A | 4/1997 | Lonberg |
| 5,633,425 | A | 5/1997 | Lonberg |
| 5,641,870 | A | 6/1997 | Rinderknecht |
| 5,648,260 | A | 7/1997 | Winter |
| 5,661,016 | A | 8/1997 | Lonberg |
| 5,693,761 | A | 12/1997 | Queen |
| 5,693,762 | A | 12/1997 | Queen |
| 5,821,337 | A | 10/1998 | Carter |
| 6,518,033 | B1 | 2/2003 | Gromeier |
| 7,045,605 | B2 | 5/2006 | Bander |
| 7,244,429 | B2 | 7/2007 | Zhou |
| 7,365,167 | B2 | 4/2008 | Watkins |
| 7,371,826 | B2 | 5/2008 | Presta |
| 7,709,610 | B2 | 5/2010 | Williams |
| 7,744,874 | B2 | 6/2010 | Korytko |
| 7,785,593 | B2 | 8/2010 | Barske |
| 8,637,643 | B2 | 1/2014 | Latham |
| 8,652,469 | B2 | 2/2014 | Kavanaugh |
| 8,841,418 | B2 | 9/2014 | Karsunky |
| 2005/0014934 | A1 | 1/2005 | Hinton |
| 2005/0153447 | A1 | 7/2005 | Berenson |
| 2007/0041985 | A1 | 2/2007 | Unger |
| 2008/0019974 | A1 | 1/2008 | Kim |
| 2009/0215175 | A1 | 8/2009 | Unger |
| 2009/0258013 | A1 | 10/2009 | Clark |
| 2009/0280128 | A1 | 11/2009 | Kamogawa |
| 2013/0095116 | A1 | 4/2013 | Gurney |
| 2014/0056890 | A1 | 2/2014 | Gurney |
| 2014/0186380 | A1 | 7/2014 | Gurney |
| 2014/0302034 | A1 | 10/2014 | Bankovich |
| 2015/0216970 | A1 | 8/2015 | Grogan |
| 2017/0037133 | A1 | 2/2017 | Fiedler |

FOREIGN PATENT DOCUMENTS

| EP | 0404097 | A2 | 12/1990 |
|---|---|---|---|
| EP | 1481993 | A1 | 12/2004 |
| JP | 2011153992 | A | 8/2011 |
| JP | 2014198710 | A | 10/2014 |
| JP | 2015134764 | A | 7/2015 |
| JP | 2018531914 | A | 11/2018 |
| RU | 2451689 | C2 | 5/2012 |
| WO | 8601533 | A1 | 3/1986 |
| WO | 9007861 | A1 | 7/1990 |
| WO | 9222653 | A1 | 12/1992 |
| WO | 9311161 | A1 | 6/1993 |
| WO | 9315210 | A1 | 8/1993 |
| WO | 9402610 | A1 | 2/1994 |
| WO | 9429351 | A2 | 12/1994 |
| WO | 9503832 | A1 | 2/1995 |
| WO | 9613583 | A2 | 5/1996 |
| WO | 9637621 | A2 | 11/1996 |
| WO | 0008166 | A1 | 2/2000 |
| WO | 03080672 | A1 | 10/2003 |
| WO | 2004074324 | A2 | 9/2004 |
| WO | 2006124667 | A2 | 11/2006 |
| WO | 2007072866 | A1 | 6/2007 |
| WO | 2014130879 | A2 | 8/2014 |
| WO | 2015009856 | A2 | 1/2015 |
| WO | 2015031693 | A1 | 3/2015 |
| WO | 2015051159 | A1 | 4/2015 |
| WO | 2015142303 | A1 | 9/2015 |
| WO | 2017021526 | A1 | 2/2017 |
| WO | 2017149538 | A1 | 9/2017 |

OTHER PUBLICATIONS

Tamura et al., (2000) Structural correlates of an anticarcinoma antibody: identification of specificity-determining 1 residues (SDRs) and development of a minimally immunogenic antibody variant by retention of SDRs only. J Immunol 164(3): 1432-1441.

Al-Lazikani et al., (1997) Standard conformations for the canonical structures of immunoglobulins. J Mol Biol 273(4): 927-948.

Altschul et al., (1990) Basic local alignment search tool. J Mol Biol 215(3): 403-410.

Beerli et al., (1994) Intracellular expression of single chain antibodies reverts ErbB-2 transformation. J Biol Chem 269 (39): 23931-23936.

Berman and Henson (2003) Classifying the precancers: a metadata approach. BMC Med Inform Decis Mak 3: 8; 9 pages.

Biocca et al., (1994) Intracellular immunization with cytosolic recombinant antibodies. Biotechnology (N Y) 12(4): 396-399.

Bird et al., (1988) Single-chain antigen-binding proteins. Science 242(4877): 423-426.

Blake et al., (2016) Suppression of Metastases Using a New Lymphocyte Checkpoint Target for Cancer Immunotherapy. Cancer Discov 6(4): 446-459.

Boerner et al., (1991) Production of antigen-specific human monoclonal antibodies from in vitro-primed human splenocytes. J Immunol 147(1): 86-95.

Bottino et al., (2003) Identification of PVR (CD155) and Nectin-2 (CD112) as cell surface ligands for the human DNAM-1 (CD226) activating molecule. J Exp Med 198(4): 557-567.

Brennan et al., (1985) Preparation of bispecific antibodies by chemical recombination of monoclonal immunoglobulin G1 fragments. Science 229(4708): 81-83.

Bryson et al., (2010) Prediction of immunogenicity of therapeutic proteins: validity of computational tools. BioDrugs 24 (1): 1-8.

Carlson (1993) A new use for intracellular antibody expression: inactivation of human immunodeficiency virus type 1. Proc Natl Acad Sci U S A 90(16): 7427-7428.

Carter et al., (1992) High level *Escherichia coli* expression and production of a bivalent humanized antibody fragment. Biotechnology (N Y) 10(2): 163-167.

Chauvin et al., (2015) TIGIT and PD-1 impair tumor antigen-specific CD8+ T cells in melanoma patients. J Clin Invest 125(5): 2046-2058.

Chen et al., (1994) Intracellular antibodies as a new class of therapeutic molecules for gene therapy. Hum Gene Ther 5(5): 595-601.

Chen et al., (1994) Combined intra- and extracellular immunization against human immunodeficiency virus type 1 infection with a human anti-gp120 antibody. Proc Natl Acad Sci U S A 91(13): 5932-5936.

Chothia et al., (1989) Conformations of immunoglobulin hypervariable regions. Nature 342(6252): 877-883.

Chowdhury (2003) Engineering hot spots for affinity enhancement of antibodies. Methods Mol Biol 207: 179-196.

Clackson et al., (1991) Making antibody fragments using phage display libraries. Nature 352(6336): 624-628.

Colman (1994) Effects of amino acid sequence changes on antibody-antigen interactions. Res Immunol 145(1): 33-36.

Cunningham and Wells (1989) High-resolution epitope mapping of hGH-receptor interactions by alanine-scanning mutagenesis. Science 244(4908): 1081-1085.

Deng Huping (2007); "The mechanism of soluble CD155 production". Master's thesis. Department of Immunology, The Fourth Military Medical University, Xi'an, China. total 82 pages including English abstract appear on pp. 7-9.

Deshane et al., (1994) Intracellular single-chain antibody directed against erbB2 down-regulates cell surface erbB2 and exhibits a selective anti-proliferative effect in erbB2 overexpressing cancer cell lines. Gene Ther 1(5): 332-337. (Abstract only, total 1 page).

Duan et al., (1994) Potent inhibition of human immunodeficiency virus type 1 replication by an intracellular anti-Rev single-chain antibody. Proc Natl Acad Sci U S A 91(11): 5075-5079 with retraction and corrections.

Duncan and Winter (1988) The binding site for C1q on IgG. Nature 332(6166): 738-740.

Fields et al., (2013) Creation of recombinant antigen-binding molecules derived from hybridomas secreting specific antibodies. Nat Protoc 8(6): 1125-1148.

(56)           References Cited

OTHER PUBLICATIONS

Fishwild et al., (1996) High-avidity human IgG kappa monoclonal antibodies from a novel strain of minilocus transgenic mice. Nat Biotechnol 14(7): 845-851.
Fuchs et al., (2004) Cutting edge: CD96 (tactile) promotes NK cell-target cell adhesion by interacting with the poliovirus receptor (CD155). J Immunol 172(7): 3994-3998.
Gilfillan et al., (2008) DNAM-1 promotes activation of cytotoxic lymphocytes by nonprofessional antigen-presenting cells and tumors. J Exp Med 205(13): 2965-2973.
Gupta et al., (2015) PEITC treatment suppresses myeloid derived tumor suppressor cells to inhibit breast tumor growth. Oncoimmunology 4(2): e981449; 9 pages.
Holliger et al., (1993) "Diabodies": small bivalent and bispecific antibody fragments. Proc Natl Acad Sci U S A 90(14): 6444-6448.
Honegger and Pluckthun (2001) Yet another numbering scheme for immunoglobulin variable domains: an automatic modeling and analysis tool. J Mol Biol 309(3): 657-670.
Hoogenboom and Winter (1992) By-passing immunisation. Human antibodies from synthetic repertoires of germline VH gene segments rearranged in vitro. J Mol Biol 227(2): 381-388.
Huntress Rick; Patient-derived tumor xenografts in humanized NSGTM mice: a model to study immune responses in cancer therapy. The Jackson Laboratory. Retrieved from: http://immune-checkpoint.com/wp-content/uploads/sites/24/2015/01/Day-1-15.45-Rick-Huntress.pdf, on Feb. 27, 2017. 34 pages.
Huston et al., (1988) Protein engineering of antibody binding sites: recovery of specific activity in an anti-digoxin single-chain Fv analogue produced in Escherichia coli. Proc Natl Acad Sci U S A 85(16): 5879-5883.
Inbar et al., (1972) Localization of antibody-combining sites within the variable portions of heavy and light chains. Proc Natl Acad Sci U S A 69(9): 2659-2662.
Inozuka et al., (2013) Development of a novel immunotherapy for melanoma which inhibits interaction between CD155 on melanoma cells and TIGIT on activated CTL. Journal of Investigative Dermatology 133(suppl 1): S3. Abstract No. 018.
Johnston et al., (2014) The immunoreceptor TIGIT regulates anti-tumor and antiviral CD8(+) T cell effector function. Cancer Cell 26(6): 923-937.
Jones et al., (1986) Replacing the complementarity-determining regions in a human antibody with those from a mouse. Nature 321(6069): 522-525.
Kakunaga et al., (2004) Enhancement of serum- and platelet-derived growth factor-induced cell proliferation by Necl-5/Tage4/poliovirus receptor/CD155 through the Ras-Raf-MEK-ERK signaling. J Biol Chem 279(35): 36419-36425.
Karlin and Altschul (1990) Methods for assessing the statistical significance of molecular sequence features by using general scoring schemes. Proc Natl Acad Sci U S A 87(6): 2264-2268.
Karlin and Altschul (1993) Applications and statistics for multiple high-scoring segments in molecular sequences. Proc Natl Acad Sci U S A 90(12): 5873-5877.
Kinugasa et al., (2012) Necl-5/poliovirus receptor interacts with VEGFR2 and regulates VEGF-induced angiogenesis. Circ Res 110(5): 716-726.
Köhler and Milstein (1975) Continuous cultures of fused cells secreting antibody of predefined specificity. Nature 256 (5517): 495-497.
Kučan Brlić et al., (2019) Targeting PVR (CD155) and its receptors in anti-tumor therapy. Cell Mol Immunol 16(1): 40-52.
Larrick and Fry (1991) PCR amplification of antibody genes. Methods 2(2): 106-110.
Lee et al., (2014) Inhibition of breast cancer growth and metastasis by a biomimetic peptide. Sci Rep 4: 7139; 12 pages.
Lee et al., (2020) Combination of PD-L1 and PVR determines sensitivity to PD-1 blockade. JCI Insight 5(14): e128633; 16 pages.
Lefranc et al., (2003) IMGT unique numbering for immunoglobulin and T cell receptor variable domains and Ig superfamily V-like domains. Dev Comp Immunol 27(1): 55-77.

Li et al., (2010) Cell culture processes for monoclonal antibody production. MAbs 2(5): 466-479.
Li et al., (2018) CD155 loss enhances tumor suppression via combined host and tumor-intrinsic mechanisms. J Clin Invest 128(6): 2613-2625.
Liu et al., (2015) Affinity-Tuned ErbB2 or EGFR Chimeric Antigen Receptor T Cells Exhibit an Increased Therapeutic Index against Tumors in Mice. Cancer Res 75(17): 3596-3607.
Lonberg and Huszar (1995) Human antibodies from transgenic mice. Int Rev Immunol 13(1): 65-93.
Lonberg et al., (1994) Antigen-specific human antibodies from mice comprising four distinct genetic modifications. Nature 368(6474): 856-859.
MacCallum et al., (1996) Antibody-antigen interactions: contact analysis and binding site topography. J Mol Biol 262(5): 732-745.
Makabe et al., (2008) Thermodynamic consequences of mutations in vernier zone residues of a humanized anti-human epidermal growth factor receptor murine antibody, 528. J Biol Chem 283(2): 1156-1166.
Marasco et al., (1998) Intracellular antibodies against HIV-1 envelope protein for AIDS gene therapy. Hum Gene Ther 9(11): 1627-1642.
Mariuzza et al., (1987) The structural basis of antigen-antibody recognition. Annu Rev Biophys Biophys Chem 16: 139-159.
Marks et al., (1991) By-passing immunization. Human antibodies from V-gene libraries displayed on phage. J Mol Biol 222(3): 581-597.
Marks et al., (1992) By-passing immunization: building high affinity human antibodies by chain shuffling. Biotechnology (N Y) 10(7): 779-783.
Martin et al., (1989) Modeling antibody hypervariable loops: a combined algorithm. Proc Natl Acad Sci U S A 86(23): 9268-9272.
Meuer et al., (1984) An alternative pathway of T-cell activation: a functional role for the 50 kd T11 sheep erythrocyte receptor protein. Cell 36(4): 897-906.
Mhashilkar et al., (1995) Inhibition of HIV-1 Tat-mediated LTR transactivation and HIV-1 infection by anti-Tat single chain intrabodies. EMBO J 14(7): 1542-1551.
Morimoto and Inouye (1992) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24(1-2): 107-117.
Morimoto et al., (2008) Interaction of cancer cells with platelets mediated by Necl-5/poliovirus receptor enhances cancer cell metastasis to the lungs. Oncogene 27(3): 264-273.
Morrison (1994) Immunology. Success in specification. Nature 368(6474): 812-813.
Morrison et al., (1984) Chimeric human antibody molecules: mouse antigen-binding domains with human constant region domains. Proc Natl Acad Sci U S A 81(21): 6851-6855.
Nelson et al., (2000) Demystified . . . Monoclonal antibodies. Mol Pathol 53(3): 111-117.
Neuberger (1996) Generating high-avidity human Mabs in mice. Nat Biotechnol 14(7): 826.
Nishiwada et al., (2015) Clinical significance of CD155 expression in human pancreatic cancer. Anticancer Res 35(4): 2287-2297 with correction.
Pack et al., (1993) Improved bivalent miniantibodies, with identical avidity as whole antibodies, produced by high cell density fermentation of Escherichia coli. Biotechnology (N Y) 11(11): 1271-1277.
Perry et al., (2008) New approaches to prediction of immune responses to therapeutic proteins during preclinical development. Drugs R D 9(6): 385-396.
Podsypanina et al., (2008) Oncogene cooperation in tumor maintenance and tumor recurrence in mouse mammary tumors induced by Myc and mutant Kras. Proc Natl Acad Sci U S A 105(13): 5242-5247.
Porter (1959) The hydrolysis of rabbit y-globulin and antibodies with crystalline papain. Biochem J 73(1): 119-126.
Portolano et al., (1993) Lack of promiscuity in autoantigen-specific H and L chain combinations as revealed by human H and L chain "roulette". J Immunol 150(3): 880-887.

(56) References Cited

OTHER PUBLICATIONS

Presta (1992) Antibody engineering. Current Opinion in Structural Biology 2(4): 593-596.

Refaeli et al., (2005) The protooncogene MYC can break B cell tolerance. Proc Natl Acad Sci U S A 102(11): 4097-4102.

Refaeli et al., (2008) The B cell antigen receptor and overexpression of MYC can cooperate in the genesis of B cell lymphomas. PLoS Biol 6(6): 1208-1225.

Richardson and Marasco (1995) Intracellular antibodies: development and therapeutic potential. Trends Biotechnol 13(8): 306-310.

Richardson et al., (1995) Phenotypic knockout of the high-affinity human interleukin 2 receptor by intracellular single-chain antibodies against the alpha subunit of the receptor. Proc Natl Acad Sci U S A 92(8): 3137-3141.

Riechmann et al., (1988) Reshaping human antibodies for therapy. Nature 332(6162): 323-327.

Roh et al., (2006) Transgenic mice for Cre-inducible overexpression of the oncogenes c-MYC and Pim-1 in multiple tissues. Genesis 44(10): 447-453.

Rudikoff et al., (1982) Single amino acid substitution altering antigen-binding specificity. Proc Natl Acad Sci U S A 79(6): 1979-1983.

Sakahara et al., (1985) Effect of DTPA conjugation on the antigen binding activity and biodistribution of monoclonal antibodies against alpha-fetoprotein. J Nucl Med 26(7): 750-755.

Scarano et al., (2010) Surface plasmon resonance imaging for affinity-based biosensors. Biosens Bioelectron 25(5): 957-966.

Schmidt et al., (1988) Transgenic mice bearing the human c-myc gene activated by an immunoglobulin enhancer: a pre-B-cell lymphoma model. Proc Natl Acad Sci U S A 85(16): 6047-6051.

Shaheen et al., (1996) Targeting human immunodeficiency virus type 1 reverse transcriptase by intracellular expression of single-chain variable fragments to inhibit early stages of the viral life cycle J Virol 70(6): 3392-3400.

Shibuya et al., (1996) DNAM-1, a novel adhesion molecule involved in the cytolytic function of T lymphocytes. Immunity 4(6): 573-581.

Shibuya et al., (1999) Physical and functional association of LFA-1 with DNAM-1 adhesion molecule. Immunity 11(5): 615-623.

Solecki et al., (2002) Expression of the human poliovirus receptor/CD155 gene is activated by sonic hedgehog. J Biol Chem 277(28): 25697-25702.

Stanietsky et al., (2009) The interaction of TIGIT with PVR and PVRL2 inhibits human NK cell cytotoxicity. Proc Natl Acad Sci U S A 106(42): 17858-17863.

Stanietsky et al., (2013) Mouse TIGIT inhibits NK-cell cytotoxicity upon interaction with PVR. Eur J Immunol 43(8): 2138-2150.

Topalian et al., (2015) Immunotherapy: The path to win the war on cancer?. Cell 161(2): 185-186.

Verhoeyen et al., (1988) Reshaping human antibodies: grafting an antilysozyme activity. Science 239(4847): 1534-1536.

Wang et al., (2019) Improvement of in vitro potency assays by a resting step for clinical-grade chimeric antigen receptor engineered T cells. Cytotherapy 21(5): 566-578.

Ward et al., (1989) Binding activities of a repertoire of single immunoglobulin variable domains secreted from Escherichia coli. Nature 341(6242): 544-546.

Werge et al., (1990) Intracellular immunization. Cloning and intracellular expression of a monoclonal antibody to the p21ras protein. FEBS Lett 274(1-2): 193-198.

Whitelegg and Rees (2000) WAM: an improved algorithm for modelling antibodies on the WEB. Protein Eng 13(12): 819-824.

Whitlow and Filpula (1991) Single-chain Fv proteins and their fusion proteins. Methods 2(2): 97-105.

Wu and Kabat (1970) An analysis of the sequences of the variable regions of Bence Jones proteins and myeloma light chains and their implications for antibody complementarity. J Exp Med 132(2): 211-250.

Yang et al., (1986) A common pathway for T lymphocyte activation involving both the CD3-Ti complex and CD2 sheep erythrocyte receptor determinants. J Immunol 137(4): 1097-1100. (Abstract only, 1 page).

Yu et al., (2009) The surface protein TIGIT suppresses T cell activation by promoting the generation of mature immunoregulatory dendritic cells. Nat Immunol 10(1): 48-57.

Zapata et al., (1995) Engineering linear F(ab')2 fragments for efficient production in Escherichia coli and enhanced antiproliferative activity. Protein Eng 8(10): 1057-1062.

Zhang Qing et al., (2015) "Anti-tumor immunotherapy and effect mechanism of TIGIT blocking monoclonal antibody". Institute of Immunology, School of Life Sciences, University of Science and Technology of China. with Machine translation, total 2 pages.

Zhu et al., (2016) Identification of CD112R as a novel checkpoint for human T cells. J Exp Med 213(2): 167-176.

* cited by examiner

| scFv 324P sample | $k_a$ (1/Ms) | $k_d$ (1/s) | $K_D$ (nM) | Relative $K_D$ * | $R_{max}$ (RU) | Chi$^2$ (RU$^2$) |
|---|---|---|---|---|---|---|
| VH0/Vκ0 WT | $1.40 \times 10^5$ | $7.15 \times 10^{-4}$ | 5.12 | 1.00 | 90.5 | 0.24 |
| VH0/Vκ0 Ala$_{56}$ | $1.54 \times 10^5$ | $7.01 \times 10^{-4}$ | 4.57 | 0.89 | 67.5 | 0.08 |
| VH0/Vκ0 Asp$_{56}$ | $1.95 \times 10^5$ | $6.37 \times 10^{-4}$ | 3.27 | 0.64 | 89.6 | 0.08 |
| VH0/Vκ0 Glu$_{56}$ | $1.84 \times 10^5$ | $6.53 \times 10^{-4}$ | 3.55 | 0.69 | 72.9 | 0.10 |
| VH0/Vκ0 Ser$_{56}$ | $1.52 \times 10^5$ | $7.01 \times 10^{-4}$ | 4.61 | 1.05 | 76.4 | 0.16 |
| VH0/Vκ0 Pro$_{56}$ | $1.38 \times 10^5$ | $1.05 \times 10^{-3}$ | 7.58 | 1.48 | 79.7 | 0.09 |
| VH0/Vκ0 Thr$_{56}$ | $1.56 \times 10^5$ | $6.88 \times 10^{-4}$ | 4.40 | 0.86 | 66.4 | 0.07 |

FIG. 1A

| Antibody IgG4 (S241P) | $IC_{50}$ [nM] | Relative $IC_{50}$ to WT* |
|---|---|---|
| WT | 0.77 | 1.00 |
| $Ala_{56}$ | 0.57 | 0.73 |
| $Asp_{56}$ | 0.66 | 0.85 |
| $Arg_{56}$ | 0.92 | 1.19 |
| $Glu_{56}$ | 0.55 | 0.71 |
| $Pro_{56}$ | 0.85 | 1.10 |
| $Thr_{56}$ | 0.79 | 1.02 |
| $Ser_{56}$ | 0.75 | 0.96 |

FIG. 1B

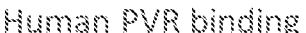
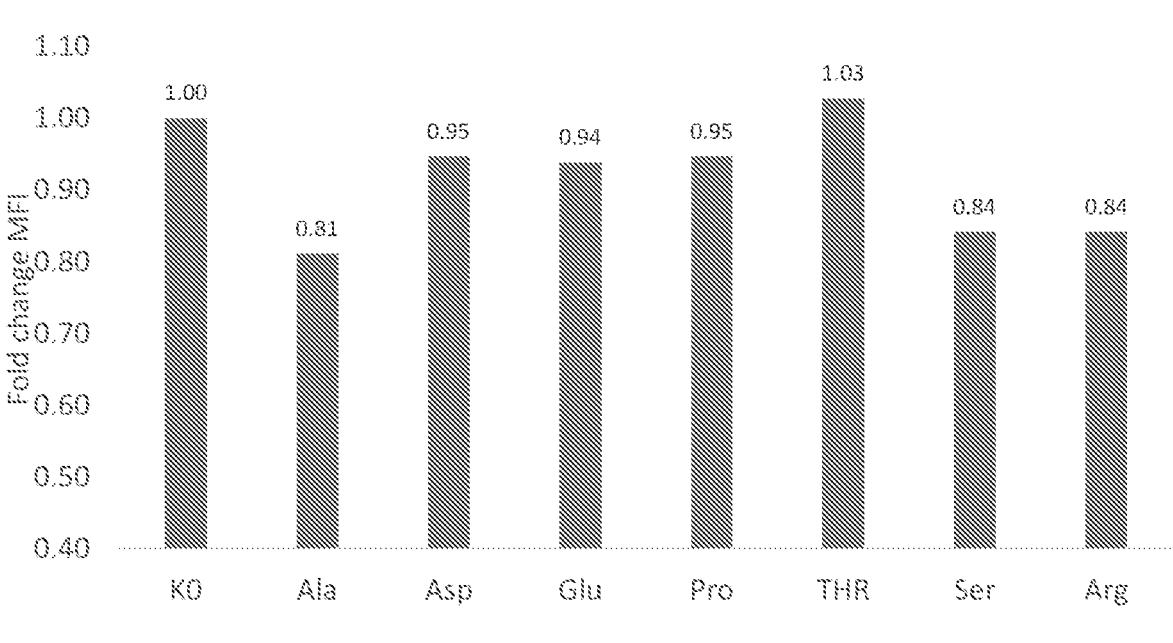
FIG. 2A
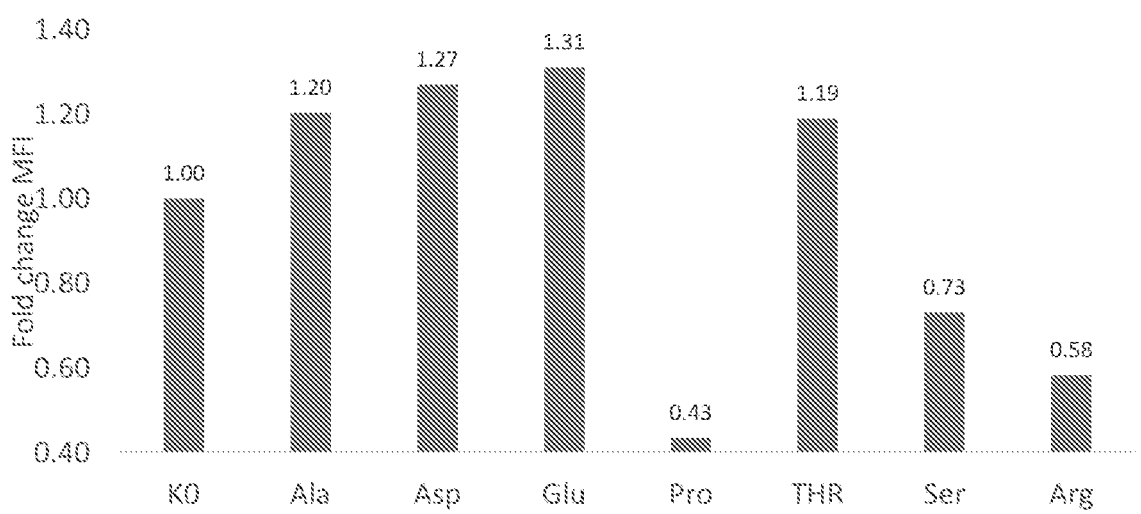
FIG. 2B

| Antibody | $K_D$ (nM) | Relative $K_D$ | Chi² (RU) |
|---|---|---|---|
| IgG4($S_{241}P$)_N56E_VH0/Vκ0 | 5.54 | 1.00 | 0.136 |
| IgG4($S_{241}P$)_N56E_VH0/Vκ1 | 4.03 | 0.73 | 0.0478 |
| IgG4($S_{241}P$)_N56E_VH1/Vκ0 | 4.50 | 0.81 | 0.0654 |
| IgG4($S_{241}P$)_N56E_VH1/Vκ1 | 4.17 | 0.75 | 0.155 |
| IgG4($S_{241}P$)_N56E_VH1/Vκ2 | 4.01 | 0.72 | 0.0449 |
| IgG4($S_{241}P$)_N56E_VH1/Vκ3 | 4.98 | 0.90 | 0.0655 |
| IgG4($S_{241}P$)_N56E_VH1/Vκ4 | 69.30 | 12.51 | 0.00276 |
| IgG4($S_{241}P$)_N56E_VH2/Vκ1 | 3.96 | 0.71 | 0.0559 |
| IgG4($S_{241}P$)_N56E_VH2/Vκ2 | 4.67 | 0.84 | 0.0666 |
| IgG4($S_{241}P$)_N56E_VH2/Vκ3 | 5.14 | 0.93 | 0.0677 |
| IgG4($S_{241}P$)_N56E_VH2/Vκ4 | 78.30 | 14.13 | 0.00322 |
| IgG4($S_{241}P$)_N56E_VH3/Vκ1 | 4.56 | 0.82 | 0.144 |
| IgG4($S_{241}P$)_N56E_VH3/Vκ2 | 4.32 | 0.78 | 0.0593 |
| IgG4($S_{241}P$)_N56E_VH3/Vκ3 | 5.42 | 0.98 | 0.0766 |
| IgG4($S_{241}P$)_N56E_VH3/Vκ4 | 75.20 | 13.57 | 0.0021 |
| IgG4($S_{241}P$)_N56E_VH4/Vκ1 | 4.62 | 0.83 | 0.0398 |
| IgG4($S_{241}P$)_N56E_VH4/Vκ2 | 6.76 | 1.22 | 0.0451 |
| IgG4($S_{241}P$)_N56E_VH4/Vκ3 | 5.11 | 0.92 | 0.0408 |
| IgG4($S_{241}P$)_N56E_VH4/Vκ4 | 96.00 | 17.33 | 0.00499 |
| IgG4($S_{241}P$)_N56E_VH5/Vκ1 | 5.91 | 1.07 | 0.0851 |
| IgG4($S_{241}P$)_N56E_VH5/Vκ2 | 5.68 | 1.03 | 0.0677 |
| IgG4($S_{241}P$)_N56E_VH5/Vκ3 | 7.41 | 1.34 | 0.0462 |
| IgG4($S_{241}P$)_N56E_VH5/Vκ4 | 76.80 | 13.86 | 0.00500 |

FIG. 5A

| Antibody Variant | $EC_{50}$ (nM) | Relative $EC_{50}$ |
|---|---|---|
| IgG4($S_{241}P$)_N56E_VH0/Vκ0 | 0.79 | 1.00 |
| IgG4($S_{241}P$)_N56E_VH2/Vκ2 | 0.64 | 0.81 |
| IgG4($S_{241}P$)_N56E_VH2/Vκ3 | 0.60 | 0.76 |
| IgG4($S_{241}P$)_N56E_VH3/Vκ2 | 0.52 | 0.66 |
| IgG4($S_{241}P$)_N56E_VH3/Vκ3 | 0.53 | 0.68 |
| IgG4($S_{241}P$)_N56E_VH4/Vκ2 | 0.67 | 0.86 |
| IgG4($S_{241}P$)_N56E_VH4/Vκ3 | 0.59 | 0.75 |
| IgG4($S_{241}P$)_N56E_VH5/Vκ2 | 0.64 | 0.82 |
| IgG4($S_{241}P$)_N56E_VH5/Vκ3 | 0.57 | 0.72 |

FIG. 5B

| Antibody Variant | IgG1 Isotype (µg/mL) | IgG4(S₂₈P) Isotype (µg/mL) |
|---|---|---|
| VH0/Vκ0 | 11.9 | 8.7 |
| VH0/Vκ1 | 45.0 | 54.3 |
| VH1/Vκ0 | 8.5 | 7.1 |
| VH1/Vκ1 | 33.8 | 54.2 |
| VH1/Vκ2 | 33.7 | 35.6 |
| VH1/Vκ3 | 35.7 | 73.2 |
| VH1/Vκ4 | 47.6 | 51.4 |
| VH2/Vκ1 | 34.6 | 69.0 |
| VH2/Vκ2 | 33.4 | 37.7 |
| VH2/Vκ3 | 47.1 | 86.4 |
| VH2/Vκ4 | 29.4 | 61 |
| VH3/Vκ1 | 32.2 | 44.9 |
| VH3/Vκ2 | 22.0 | 46.6 |
| VH3/Vκ3 | 32.5 | 90.0 |
| VH3/Vκ4 | 18.2 | 105.4 |
| VH4/Vκ1 | 38.6 | 46.3 |
| VH4/Vκ2 | 46.0 | 108.7 |
| VH4/Vκ3 | 59.6 | 77.5 |
| VH4/Vκ4 | 45.8 | 58.4 |
| VH5/Vκ1 | 39.1 | 56.1 |
| VH5/Vκ2 | 45.1 | 52.5 |
| VH5/Vκ3 | 29.6 | 62.2 |
| VH5/Vκ4 | 18.2 | 76.7 |

FIG. 6A

| VH variant | % identity with closest human germline gene |
|------------|---------------------------------------------|
| VH2        | 75.5                                        |
| VH3        | 78.6                                        |
| VH4        | 80.6                                        |
| VH5        | 82.7                                        |

| VK variant | % identity |
|------------|------------|
| VK2        | 83         |
| VK3        | 84.2       |

FIG. 6B

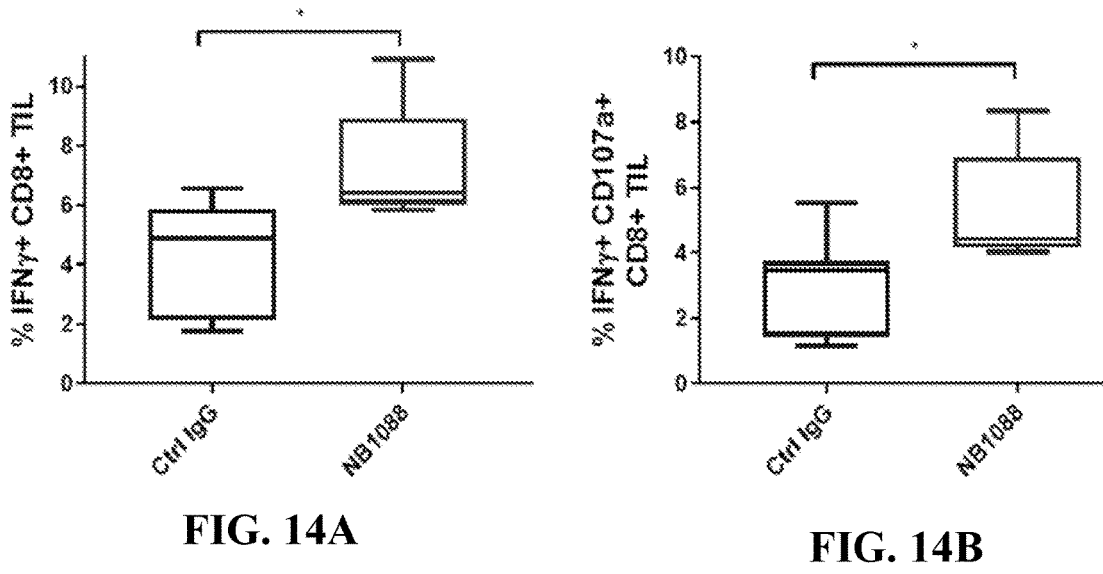
FIG. 14A                                          FIG. 14B
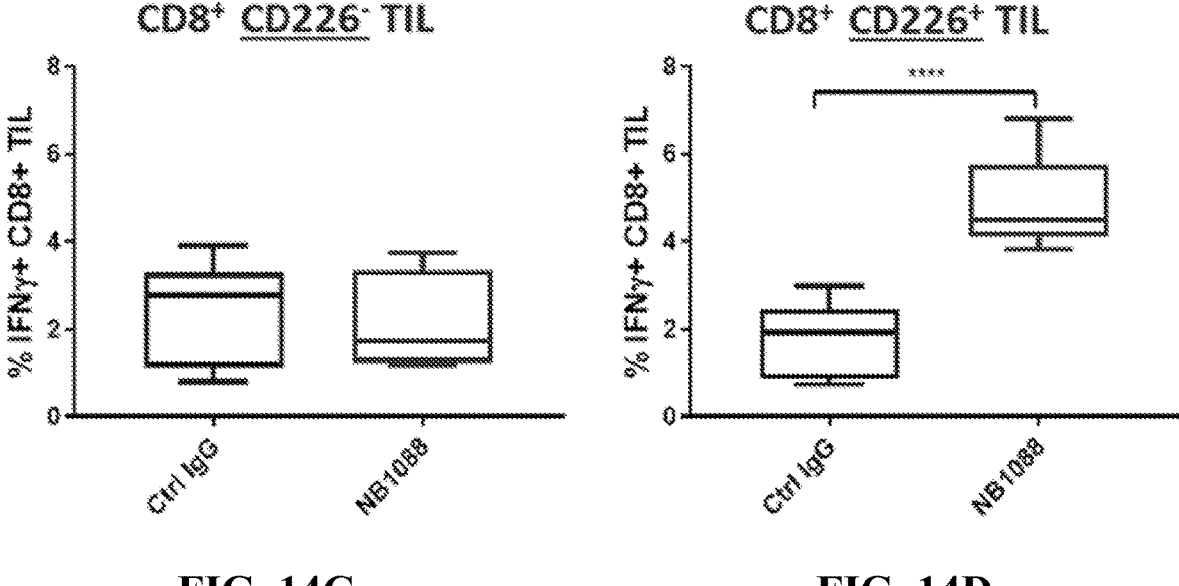
FIG. 14C                                          FIG. 14D ScFv

ANTIBODIES AGAINST THE POLIOVIRUS RECEPTOR (PVR) AND USES THEREOF

CROSS-REFERENCE TO RELATED APPLICATIONS

The present application is a National Stage filing under 35 U.S.C. § 371 of PCT/IL2020/051082, filed on Oct. 7, 2020, and claims the benefit of priority to U.S. Provisional Application No. 62/912,534, filed on Oct. 8, 2019. Each application is incorporated herein by references in their entirety.

The present application includes a Sequence Listing filed in electronic format. The Sequence Listing is entitled "NECTIN001PCT-sequence_listing_ST25.txt" created on Mar. 24, 2022, and is 48000 bytes in size. The information in the electronic format of the Sequence Listing is part of the present application and is incorporated herein by reference in its entirety.

FIELD OF THE INVENTION

The present invention is in the field of immunotherapy and relates to humanized antibodies, comprising specific sets of CDR and framework sequences that specifically bind to human poliovirus receptor (PVR). Pharmaceutical compositions comprising these humanized antibodies and their uses are also included.

BACKGROUND OF THE INVENTION

Poliovirus receptor (PVR), also termed CD155, is a transmembrane glycoprotein involved in mediating cell adhesion to extracellular matrix molecules. It was previously described as a tumor antigen and as a potential target for therapeutic intervention as its expression is up-regulated in neuroectodermal cancers, including glioblastoma multiforme, medulloblastoma, and colorectal carcinoma (Solecki et al., J. Biol. Chem. 2002, 277: 25697-700), as well as in pancreatic cancer (Nishiwada et al., Anticancer Res. 2015, 35(4): 2287-97). PVR is also known to enhance the serum-induced activation of the Ras-Raf-MEK-ERK signaling, up-regulating cyclins D2 and E, and down-regulated p27Kip1, eventually shortening the period of the G0/G1 phase of the cell cycle (Kakunaga 2004, J. Biological Chemistry, 279, 36419-36425. For that reason, blocking of PVR on tumor cells is anticipated to reduce their viability. PVR has also a critical role in angiogenesis and is suggested to regulate the VEGF-induced angiogenesis by controlling the interaction of Vascular endothelial growth factor receptor 2 (VEGFR2) with integrin $\alpha(v)\beta(3)$, and the VEGFR2-mediated Rap1-Akt signaling pathway (Kinugasa et al., 2012, Circ Res. 2012, 110(5), 716-26). Additionally, PVR is complexing with IGF1R and participating in tyrosine-protein kinase Met (cMet) signaling and blocking the complex formation reduced cell viability and angiogenesis (Lee et al., Scientific Reports 2014, 20, 4, 7139).

In recent years it became evident that PVR is a critical immune check point ligand (Brilc P. K. et al 2019 Cell Mol Immunology). PVR expression is upregulated in both malignant cells and tumor-infiltrating myeloid cells in humans and mice. PVR−/− mice display reduced tumor growth and metastasis via DNAM-1 (CD226) upregulation and enhanced effector function of CD8+ T and NK cells, respectively. Blockade of Programmed cell death protein 1 (PD-1) or both PD-1 and cytotoxic T-lymphocyte-associated protein 4 (CTLA4) is more effective in settings in which PVR was limiting, suggesting the clinical potential of combinatory therapy using PD-1/PD-L1 and PVR blockade (LI X. Y et.al JCI 2018). Moreover, in clinical settings, the expression of PD-L1 and PVR is independently regulated, which allowed stratification of patients who were treated with anti-PD-1 antibody into 4 groups according to the expression levels of PD-L1 and PVR. High PVR expression in PD-L1-low-expressing patients enriched non-responders. This was further validated using a genetically engineered cancer model. These findings bolster the significance of PVR as a critical immune check point in tumor immune-therapy (Lee B. R et al JCI. Insight 2020). PVR involvement in metastasis was demonstrated by injecting cancer cells to the tail of mice and measuring metastasis to the lungs. It has been shown that the upregulated PVR in cancer cells transinteracts with its counter-receptor in platelets, and that this trans-interaction enhances the metastasis of the cancer cells to the lungs (Morimoto et al., Oncogene (2008) 27, 264-273).

WO2017149538 to one of the present inventors discloses murine antibodies and fragments thereof which bind to PVR as well as encoding polynucleotide sequences and hybridoma cells producing these antibodies.

U.S. Patent Application No. 20070041985 discloses molecules specifically binding to at least one intra- or extracellular domain of the PVR, wherein the molecule has the ability to modulate a receptor mediated adhesion, trafficking and/or invasion behavior of a cell expressing the PVR or any derivative thereof.

U.S. Patent Application No. 20090215175 provides molecules (e.g. small chemical compounds, oligonucleotides, polypeptides, antibodies, and antibody fragments) which modulate the PVR functions necessary for adhesion, trafficking, invasion and/or metastatic potential of cells. The molecules can be used for the treatment of cells having a metastatic potential, metastasis and cancer.

There is an unmet need to provide humanized antibodies recognizing human PVR which are safer and more potent and can be used diagnostically and therapeutically in diseases involving PVR expression.

SUMMARY OF THE INVENTION

Described herein, according to some embodiments, are humanized antibodies that specifically bind human poliovirus receptor (PVR; CD155) and prevent binding of PVR to at least one of ligands, T cell immunoreceptor with Ig and ITIM domains (TIGIT), CD96 and CD226 (DNAM-1). The humanized antibodies of the present invention, selected from a larger collection of antibody clones, have improved properties compared to other known anti-PVR antibodies. These improved properties include but are not limited to reduced immunogenicity potential, improved binding affinity and activity, biophysical properties and improved expression. As PVR binding to CD226 results in down-regulation of surface expression of CD226 on T and NK cells and reduced activity of CD226 to stimulate T and NK cells and tumor cell killing, the antibodies of the present invention can restore the expression and/or activity of CD226 on these cells. Proper expression and functioning of CD226 allows for increased tumor killing by immune cells, especially CD8+ T cells and NK cells.

A large collection of humanized antibodies was produced by combining specific sets of CDR sequences and human framework sequences and introducing specific mutations in these sequences to produce improved antibodies with modified variable regions. The newly designed humanized variable regions preserve the residues critical for the maintenance of the antibody's conformation and binding affinity, while having the lowest incidence of potential T cell epitopes, thus minimizing the risk of adverse immune response towards the antibodies. The antibodies disclosed herein were designed based on factors including homology, T-cell epitopes, key residues, and predicted structures.

Unexpectedly, variants having a combination of specific human frameworks a point mutation of Glutamic acid to Asparagine in the last residue of CDR2 of the light chain variable region (position 56 according to Kabat numbering), show strong affinity to human PVR and improved immune activity.

Several humanized antibody variants according to the invention were found to be particularly suitable for chimeric antigen receptor (CAR) applications due to their lower affinity, which may be useful in targeting the highly expressed PVR tumor cells, without targeting normal tissues.

Advantageously, several humanized antibody variants according to the present invention have improved producibility and are capable of being produced with exceptionally high yield compared to other variants.

It is now disclosed that the humanized antibody described herein show high efficacy in cytotoxic T and NK cell stimulation, and in treatment of cancer in humanized mouse models, including in vivo models of pancreatic cancer and lung cancer.

The present invention thus provides, in some embodiments, highly-specific, non-immunogenic, humanized antibodies against human PVR having improved affinity, activity and/or reproducibility.

The present invention provides, according to one aspect, a humanized antibody that specifically binds human poliovirus receptor (PVR, CD155), or a fragment thereof comprising at least the antigen binding site, wherein the antibody or a fragment thereof comprises a heavy chain and a light chain, wherein the heavy chain comprises a variable region having an amino acid sequence at least about 90% identical to a sequence selected from the group consisting of SEQ ID NO: 1, SEQ ID NO: 3, SEQ ID NO: 4, SEQ ID NO: 5 and SEQ ID NO: 6; and wherein the light chain comprises a variable region having an amino acid sequence at least about 90% identical to a sequence selected from the group consisting of SEQ ID NO: 2, SEQ ID NO: 7, SEQ ID NO: 8 and SEQ ID NO: 9.

According to some embodiments, the antibody comprises heavy-chain variable region amino-acid sequence comprising the CDR sequences set forth in SEQ ID NO:10, SEQ ID NO:11 and SEQ ID NO:12, and light-chain variable region amino-acid sequence comprising the CDR sequences set forth in SEQ ID NO:13, SEQ ID NO:14 and SEQ ID NO:15.

According to some embodiments, the humanized antibody or fragment thereof is an IgG monoclonal antibody. According to some embodiments, the humanized monoclonal antibody has a heavy chain constant region selected from IgG4 and IgG1. In certain embodiments, the humanized antibody or fragment thereof is an IgG4 subclass. In certain embodiments, the humanized antibody or antigen binding fragment thereof is an IgG1 subclass.

According to some embodiments, the humanized antibody or fragment thereof comprises a human IgG4 constant region having S228P (also named S241P) substitution in the hinge region.

According to some embodiments, the humanized antibody or fragment thereof is a monoclonal antibody, Fab, F(ab)$_2$, a single-domain antibody, or a single chain variable fragment (scFv).

According to some embodiments, the humanized antibody or antigen binding fragment thereof comprises a heavy chain variable region comprising the amino acid sequence QVQLVQSGAE(L/V)KKPGASVK(I/V)SCK-ATGYTFSNYWIEW(I/V)(K/R)QAPGQGLEW(I/M)GEI-FPGSGRINFNEKFKGR(A/V)TFTADTSI(D/S)T(T/A)YM(Q/E)LS(S/R)L(T/R)SDD(S/T)AVYYCARTKIYGNSFDYWGQGT(T/L)VTVSS (SEQ ID NO: 47); and a light chain variable region comprising the amino acid sequence DI(M/Q)MTQSPS(F/S)LSASVGDRVTITC(K/R)ASQDVGTAV(V/A)WYQQKPGKAPK(L/S)LIYWASSRHEGVP(D/S)RF(T/S)GSGSGTDFTLTISSLQ(S/P)EDFA(D/T)YFCQQYSRYPLTFGQGT KLEIK (SEQ ID NO: 48).

According to some embodiments, the humanized antibody or fragment thereof comprises a heavy chain variable region comprising:
  i. a set of three CDR sequences comprising the sequences set forth in SEQ ID Nos. 10-12; and
  ii. a set of four heavy chain framework (FR) sequences: (A) FR-H1 selected from the group consisting of SEQ ID NOs: 18, 22, and 26; (B) FR-H2 selected from the group consisting of SEQ ID NOs: 19, 23, and 28; (C) FR-H3 selected from the group consisting of SEQ ID NOs: 20, 24, 27, and 29; and (D) FR-H4 selected from the group consisting of SEQ ID NOs: 21 and 25.

According to some embodiments, the humanized antibody or antigen binding fragment thereof comprising a light chain variable region comprising:
  i. a set of three CDR sequences comprising the sequences set forth in SEQ ID Nos. 13-15; and
  ii. a set of four light chain framework sequences: (A) FR-L1 selected from the group consisting of SEQ ID NOs: 30 and 34; (B) FR-L2 selected from the group consisting of SEQ ID NOs: 31 and 37; (C) FR-L3 selected from the group consisting of SEQ ID NOs: 32, 35, and 36; and (D) FR-L4 is SEQ ID NO: 33.

According to some embodiments, the humanized antibody or antigen binding fragment thereof comprising a heavy chain variable region and a light chain variable region, the heavy chain variable region comprising:
  i. a set of three CDR sequences comprising the sequences set forth in SEQ ID Nos. 10-12; and
  ii. a set of four heavy chain (HC) framework (FR) sequences: (A) FR-H1 selected from the group consisting of SEQ ID NOs: 18, 22, and 26; (B) FR-H2 selected from the group consisting of SEQ ID NOs: 19, 23, and 28; (C) FR-H3 selected from the group consisting of SEQ ID NOs: 20, 24, 27, and 29; (D) FR-H4 selected from the group consisting of SEQ ID NOs: 21 and 25;
  and the light chain variable region comprising:
  i. a set of three CDR sequences comprising the sequences set forth in SEQ ID Nos. 13-15; and
  ii. a set of four light chain (LC) framework (FR) sequences: (A) FR-L1 selected from the group consisting of SEQ ID NOs: 30 and 34; (B) FR-L2 selected from the group consisting of SEQ ID NOs: 31 and 37; (C) FR-L3 selected from the group consisting of SEQ ID NOs: 32, 35, and 36; and (D) FR-L4 is SEQ ID NO: 33.

According to some embodiments, the heavy chain variable region of the humanized monoclonal antibody comprises an amino acid sequence at least about 90% identical to a sequence selected from the group consisting of SEQ ID NO: 1, SEQ ID NO: 3, SEQ ID NO: 4, SEQ ID NO: 5 and SEQ ID NO: 6; and the light chain variable region comprises an amino acid sequence at least about 90% identical to a sequence selected from the group consisting of SEQ ID NO: 2, SEQ ID NO: 7, SEQ ID NO: 8 and SEQ ID NO: 9. According to some embodiments, the heavy chain variable region of the humanized monoclonal antibody comprises an amino acid sequence at least about 95% identical to a sequence selected from the group consisting of SEQ ID NO: 1, SEQ ID NO: 3, SEQ ID NO: 4, SEQ ID NO: 5 and SEQ ID NO: 6; and the light chain variable region comprises an amino acid sequence at least about 95% identical to a sequence selected from the group consisting of SEQ ID NO: 2, SEQ ID NO: 7, SEQ ID NO: 8 and SEQ ID NO: 9. In certain embodiments, the heavy chain variable region of the humanized monoclonal antibody comprises an amino acid sequence at least about 97% identical to a sequence selected from the group consisting of SEQ ID NO: 1, SEQ ID NO: 3, SEQ ID NO: 4, SEQ ID NO: 5 and SEQ ID NO: 6, and the light chain variable region comprises an amino acid sequence at least about 97% identical to a sequence selected from the group consisting of SEQ ID NO: 2, SEQ ID NO: 7, SEQ ID NO: 8 and SEQ ID NO: 9. In certain embodiments, the heavy chain variable region of the humanized monoclonal antibody comprises an amino acid sequence selected from the group consisting of SEQ ID NO: 1, SEQ ID NO: 3, SEQ ID NO: 4, SEQ ID NO: 5 and SEQ ID NO: 6, and the light chain variable region comprises an amino acid sequence selected from the group consisting of SEQ ID NO: 2, SEQ ID NO: 7, SEQ ID NO: 8 and SEQ ID NO: 9.

According to some embodiments, the humanized antibody comprises a combination of a heavy chain variable region and a light chain variable region, wherein the combination is selected from the group consisting of:

i. a heavy chain variable region sequence set forth in SEQ ID NO: 1 and a light chain variable region sequence set forth in SEQ ID NO: 2;

ii. a heavy chain variable region sequence set forth in SEQ ID NO: 4 and a light chain variable region sequence set forth in SEQ ID NO: 8;

iii. a heavy chain variable region sequence set forth in SEQ ID NO: 5 and a light chain variable region sequence set forth in SEQ ID NO: 2;

iv. a heavy chain variable region sequence set forth in SEQ ID NO: 5 and a light chain variable region sequence set forth in SEQ ID NO: 8;

v. a heavy chain variable region sequence set forth in SEQ ID NO: 4 and a light chain variable region sequence set forth in SEQ ID NO: 2;

vi. a heavy chain variable region sequence set forth in SEQ ID NO: 1 and a light chain variable region sequence set forth in SEQ ID NO: 8;

vii. a heavy chain variable region sequence set forth in SEQ ID NO: 6 and a light chain sequence set forth in SEQ ID NO: 2; and viii. a heavy chain variable region sequence set forth in SEQ ID NO: 6 and a light chain variable region sequence set forth in SEQ ID NO: 8.

According to some embodiments, the heavy chain variable region of the humanized monoclonal antibody comprises an amino acid sequence at least about 90% identical to that set forth in SEQ ID NO: 1, and the light chain variable region comprises an amino acid sequence at least about 90% identical to that set forth in SEQ ID NO: 2.

According to some embodiments, the heavy chain variable region of the humanized monoclonal antibody comprises an amino acid sequence identical to that set forth in SEQ ID NO: 1, and the light chain variable region comprises an amino acid sequence identical to that set forth in SEQ ID NO: 2.

According to some embodiments, the humanized antibody inhibits binding of PVR to at least one of TIGIT, CD96, and CD226.

According to some embodiments, the antibody inhibits binding of PVR to TIGIT, CD96, and CD226.

According to some embodiments, the humanized antibody is an IgG4 antibody comprising a heavy chain sequences set forth in SEQ ID NO: 49, or a sequence having at least 90% identity. According to some embodiments, the humanized antibody is an IgG1 comprising a heavy chain sequence set forth in SEQ ID NO: 50 or a sequence having at least 90% identity.

According to some embodiments, the humanized antibody comprising a light chain sequence set forth in SEQ ID NO: 49.

According to some embodiments, the humanized antibody exhibits improved antibody-dependent cellular cytotoxicity (ADCC) or complement dependent cytotoxicity (CDC) compared to other, known antibodies.

Polynucleotide sequences encoding the humanized antibody or antigen binding fragment thereof, are provided according to another aspect of the invention.

According to some embodiments, a polynucleotide sequence encoding the amino acid sequences of a heavy chain variable region, a light chain variable region or both, as described above is provided.

According to some embodiments, a polynucleotide is provided encoding a heavy chain variable region comprising an amino acid sequence selected from the group consisting of SEQ ID NO: 1, SEQ ID NO: 3, SEQ ID NO: 4, SEQ ID NO: 5 and SEQ ID NO: 6.

According to some embodiments, a polynucleotide is provided encoding a light chain variable region comprising an amino acid sequence selected from the group consisting of SEQ ID NO: 2, SEQ ID NO: 7, SEQ ID NO: 8 and SEQ ID NO: 9.

According to some embodiments, the polynucleotide encodes a humanized antibody or antibody fragment thereof comprising: a heavy chain variable region comprising an amino acid sequence selected from the group consisting of SEQ ID NO: 1, SEQ ID NO: 3, SEQ ID NO: 4, SEQ ID NO: 5 and SEQ ID NO: 6; and a light chain variable region comprising an amino acid sequence selected from the group consisting of SEQ ID NO: 2, SEQ ID NO: 7, SEQ ID NO: 8 and SEQ ID NO: 9. Each combination of heavy and light chain variable regions represents a separate embodiment of the invention.

According to some embodiments, the polynucleotide sequence encoding the humanized antibody heavy chain variable region comprises a sequence selected from the group consisting of SEQ ID NOs: 38-42, or a variant thereof having at least 90% sequence identity. Each possibility represents a separate embodiment of the invention.

According to some embodiments, the polynucleotide sequence encoding the humanized antibody light chain variable region comprises a sequence selected from the group consisting of SEQ ID NOs: 43-46, or a variant thereof having at least 90% sequence identity. Each possibility represents a separate embodiment of the invention.

In a further aspect, the present invention provides a nucleic acid construct comprising a nucleic acid molecule encoding at least one humanized antibody chain or fragment thereof as described herein. According to some embodiments the nucleic acid construct is a plasmid.

Also described is a cell line comprising the nucleic acids encoding the antibodies of the present invention. The cell line is for expression of the humanized antibody or fragment thereof as described herein. In certain embodiments, the cell line is a mammalian cell line such as a Chinese Hamster Ovary (CHO) cell line.

According to some embodiments, the cell line is a bacterial, plant, murine (e.g., NS0 and Sp2/0), rat (e.g., YB2/0), hamster (e.g., BHK and CHO) or human (e.g., PER.C6).

According to an aspect, the present invention provides a chimeric antigen receptor (CAR) comprising an extracellular portion (binding domain), containing any of the humanized antibodies or fragment thereof as described herein. According to some embodiments, a CAR comprising a combination of heavy and light chain variable region sequences described above, having unique combination of CDR and framework sequences and improved binding and other properties, is provided.

According to some embodiments, the CAR comprises a combination of heavy and light chain variable regions, the heavy chain variable region comprises an amino acid sequence with at least 90% sequence identity to a sequence selected from the group consisting of SEQ ID NO: 1, SEQ ID NO: 3, SEQ ID NO: 4, SEQ ID NO: 5 and SEQ ID NO: 6; and the light chain variable region comprises an amino acid sequence with at least 90% sequence identity to a sequence selected from the group consisting of SEQ ID NO: 2, SEQ ID NO: 7, SEQ ID NO: 8 and SEQ ID NO: 9.

According to some embodiments, the CAR comprises a heavy chain variable region comprising an amino acid sequence selected from the group consisting of SEQ ID NO: 1, SEQ ID NO: 3, SEQ ID NO: 4, SEQ ID NO: 5 and SEQ ID NO: 6, and a light chain variable region comprising an amino acid sequence selected from the group consisting of SEQ ID NO: 2, SEQ ID NO: 7, SEQ ID NO: 8 and SEQ ID NO: 9.

According to some embodiments, the CAR comprises a combination of a humanized antibody heavy and light chain variable regions, wherein the combination is selected from the group consisting of:

i. a heavy chain variable region sequence set forth in SEQ ID NO: 1 and a light chain variable region sequence set forth in SEQ ID NO: 9;

ii. a heavy chain variable region sequence set forth in SEQ ID NO: 3 and a light chain variable region sequence set forth in SEQ ID NO: 9;

iii. a heavy chain variable region sequence set forth in SEQ ID NO: 4 and a light chain variable region sequence set forth in SEQ ID NO: 9;

iv. a heavy chain variable region sequence set forth in SEQ ID NO: 5 and a light chain variable region sequence set forth in SEQ ID NO: 9; and v. a heavy chain variable region sequence set forth in SEQ ID NO: 6 and a light chain variable region sequence set forth in SEQ ID NO: 9.

According to some embodiments, the CAR comprises a heavy chain variable region sequence selected from the group consisting of SEQ ID NO: 1, 3, 4, 5, and 6, and a light chain variable region sequence set forth in SEQ ID NO: 9, a transmembrane domain, and an intracellular T cell signaling domain.

A single chain variable region (scFv) comprising the heavy chain and light chain variable regions of the antibodies described herein is also provided according to the present invention. According to certain embodiments, there is a hinge region between the variable regions.

According to some embodiments, the amino acid sequence of the scFv is set forth in a sequence selected from SEQ ID NO: 56, SEQ ID NO: 57, and an analog thereof having at least 90% sequence similarity to any of said sequences.

According to some embodiments, the CAR comprises an amnio acid sequences set forth in any one of SEQ ID NO: 56 and SEQ ID NO: 57.

According to some embodiments, the CAR comprises a scFv sequence and at least one protein domain selected from the group consisting of a CD8 Stalk domain, a CD28 TM domain, a 41BB domain, and a CD3ζ (CD3Z, Zetta) domain. According to some embodiments, the CAR comprises a CD8 Stalk domain. According to some embodiments, the CAR comprises a CD28 TM domain. According to some embodiments, the CAR comprises a CD3Z domain. According to some embodiments, the CAR comprises a 41BB domain. According to specific embodiments, the CAR comprises a CD8 Stalk domain, a CD28 TM domain, a 41BB domain, and a CD3Z domain.

According to some embodiments, the CAR comprises a scFv sequence comprising the PVR binding site of any antibody disclosed above and at least one domain selected from the group consisting of: CD8 Stalk domain, a CD28 TM domain, a 41BB domain, and a CD3Z domain. According to specific embodiments, the CAR comprises a scFv sequence comprising the PVR binding site of any antibody disclosed above and a CD8 Stalk domain, a CD28 TM domain, a 41BB domain, and a CD3Z domain.

According to some embodiments, a lymphocyte engineered to express the CAR described herein is provided. According to some embodiments, a T cell engineered to express the CAR described herein is provided. According to additional embodiments, an NK cell engineered to express the CAR described herein is provided.

According to specific embodiments, an engineered T cell is provided, expressing a scFv sequence selected from the group consisting of: SEQ ID NO: 56, SEQ ID NO: 57, or an analog thereof having at least 90% sequence similarity to any of said sequences; a CD8 Stalk domain, a CD28 TM domain, a 41BB domain, and a CD3Z domain.

According to an aspect, the present invention provides a method of treating cancer in a subject comprising administering a therapeutically effective amount of at least one lymphocyte comprising the CAR as described herein to said subject.

The present invention provides, according to another aspect, a pharmaceutical composition comprising the humanized antibody or antigen binding fragment described herein and a pharmaceutically acceptable excipient, carrier, or diluent.

Any administration mode may be used to deliver the compositions of the present invention to a subject in need thereof, including parenteral and enteral administration modes.

According to some embodiments, the pharmaceutical composition is formulated for injection or infusion. According to some embodiments, the pharmaceutical composition is formulated for intravenous administration. In certain embodiments, the pharmaceutical composition is formulated for intratumoral administration.

According to some embodiments, the humanized antibody or antigen binding fragment thereof or the pharmaceutical composition is for use in increasing surface expression and/or signaling of CD226 on CD8+ and CD4+ T cells.

According to embodiments, the humanized antibody or antigen binding fragment thereof, or the pharmaceutical composition is for use in treating a cancer in an individual. In certain embodiments, the cancer comprises a solid tumor. In certain embodiments, the cancer is selected from the group consisting of lung cancer, colon cancer, glioblastoma, adrenal cancer, uterine cancer, head and neck cancer, pancreatic cancer, and breast cancer. Each possibility represents a separate embodiment of the invention.

According to some embodiments, the cancer is a hematological cancer.

According to some embodiments, the hematological cancer is selected from leukemia including acute myeloid leukemia (AML), chronic myeloid leukemia (CML), acute lymphocytic leukemia (ALL), and chronic lymphocytic leukemia (CLL); lymphoma, including Hodgkin disease, and non-Hodgkin lymphoma; and multiple myeloma.

According to some embodiments, the individual is human.

According to some embodiments of the invention, the use further comprises the use of an agent that downregulates the activity or expression of an immune co-inhibitory receptor.

According to some embodiments, the immune co-inhibitory receptor is selected from the group consisting of PD-1, PD-L1, TIGIT, CTLA-4, LAGS, TIM3, BTLA, VISTA, B7H4, CD96, BY55 (CD 160), LAIR1, SIGLEC10, CD112R, CD112, ILT-4 and 2B4. Each possibility represents a separate embodiment of the invention.

According to some embodiments of the invention, the use further comprises the use in a combination with an anti-endothelial growth factor receptor (EGFR) antibody.

The present invention provides, according to another aspect, a method of increasing surface expression and/or signaling of CD226 in the CD8+ and CD4+ T cells of an individual, the method comprising administering to the individual a therapeutically effective amount of the humanized antibody or antigen binding fragment thereof, or the pharmaceutical composition described herein. In certain embodiments, the CD8+ T cells are tumor infiltrating CD8+ T cells.

The present invention provides, according to another aspect, a method of treating a cancer in an individual in need of such treatment, the method comprising administering to the individual a therapeutically effective amount of the humanized antibody or antigen binding fragment thereof or the pharmaceutical composition. In certain embodiments, the cancer comprises a solid tumor. According to additional embodiments, the cancer is a non-solid tumor. In certain embodiments, the cancer is selected from the group consisting of glioblastoma, pancreatic cancer, breast cancer, bladder cancer, kidney cancer, head and neck cancer, ovarian cancer, colon cancer, cervical cancer, prostate cancer, and lung cancer. In certain embodiments, the method of treating cancer involves preventing or reducing formation, growth or spread of metastases in a subject.

The present invention provides, according to another aspect, a method of treating a cancer in an individual afflicted with a cancer comprising administering to the individual a therapeutically effective amount of the humanized antibody or antigen binding fragment thereof or the pharmaceutical composition, and an inhibitor of PD-1, PD-L1, CTLA-4 or CD112R signaling. In certain embodiments, the cancer comprises a solid tumor. In certain embodiments, the cancer is selected from the group consisting of glioblastoma, pancreatic cancer, breast cancer, bladder cancer, kidney cancer, head and neck cancer, ovarian cancer, colon cancer, cervical cancer, prostate cancer, or lung cancer. In certain embodiments, the inhibitor of PD-1 signaling is an antibody or fragment thereof that binds to PD-1. In certain embodiments, the antibody or fragment thereof that binds to PD-1 is Pembrolizumab, Nivolumab, AMP-514, Tislelizumab, Spartalizumab, or a PD-1 binding fragment thereof. In certain embodiments, the inhibitor of PD-1 signaling is an antibody that specifically binds PD-L-1 or PD-L-2. In certain embodiments, the antibody that specifically binds PD-L1 or PD-L2 comprises Durvalumab, Atezolizumab, Avelumab, BMS-936559, or FAZ053, or a PD-L1 or PD-L2 binding fragment thereof. In certain embodiments, the inhibitor of PD-1 signaling comprises an Fc-fusion protein that binds PD-1, PD-L1, or PD-L2. In certain embodiments, the Fc-fusion protein comprises AMP-224 or a PD-1 binding fragment thereof. In certain embodiments, the inhibitor of PD-1 signaling comprises a small molecule inhibitor of PD-1, PD-L1, or PD-L2. In certain embodiments, the small molecule inhibitor of PD-1, PD-L1, or PD-L2 signaling comprises on or more of: N-{2-[({2-methoxy-6-[(2-methyl[1,1'-biphenyl]-3-yl)methoxy]pyridin-3-yl}methyl)amino]ethyl}acetamide (BMS 202); (2-((3-cyanobenzyl)oxy)-4-((3-(2,3-dihydrobenzo[b][1,4]dioxin-6-yl)-2-methylbenzyl)oxy)-5-methylbenzyl)-D-serine hydrochloride; (2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid; 3-(4,6-dichloro-1,3,5-triazin-2-yl)-1-phenylindole; 3-(4,6-dichloro-1,3,5-triazin-2-yl)-1-phenyl-1h-indole; L-α-Glutamine, N2,N6-bis(L-seryl-L-asparaginyl-L-threonyl-L-seryl-L-α-glutamyl-L-seryl-L-phenylalanyl)-L-lysyl-L-phenylalanyl-L-arginyl-L-valyl-L-threonyl-L-glutaminyl-L-leucyl-L-alanyl-L-prolyl-L-lysyl-L-alanyl-L-glutaminyl-L-isoleucyl-L-lysyl; (2S)-1-[[2,6-dimethoxy-4-[(2-methyl[1,1'-biphenyl]-3-yl)methoxy]phenyl] methyl]-2-piperidinecarboxylic acid; Glycinamide, N-(2-mercaptoacetyl)-L-phenylalanyl-N-methyl-L-alanyl-L-asparaginyl-L-prolyl-L-histidyl-L-leucyl-N-methylglycyl-L-tryptophyl-L-seryl-L-tryptophyl-N-methyl-L-norleucyl-N-methyl-L-norleucyl-L-arginyl-L-cysteinyl-, cyclic (1→14)-thioether; or a derivative or analog thereof.

Also described herein is a method of making composition for treating a cancer in an individual afflicted with cancer comprising admixing the humanized antibody or antigen binding fragment thereof and a pharmaceutically acceptable excipient, carrier, or diluent. In certain embodiments, the cancer comprises a solid tumor. In certain embodiments, the cancer is selected from the group consisting of glioblastoma, pancreatic cancer, breast cancer, bladder cancer, kidney cancer, head and neck cancer, ovarian cancer, colon cancer, cervical cancer, prostate cancer, and lung cancer. Also described herein is a method of producing the humanized antibody or antigen binding fragment thereof comprising incubating the cell line described herein in a cell culture medium under conditions sufficient to allow expression and secretion of the humanized antibody or antigen binding fragment thereof.

The present invention further provides, according to an aspect, a method of diagnosing or prognosing cancer in a subject, the method comprises determining the expression level of PVR in a biological sample of said subject using at least one humanized antibody, fragment or scFv as described herein.

The present invention further provides, according to another aspect, a method of determining or quantifying the expression of PVR, the method comprising contacting a biological sample with an antibody or antibody fragment as described herein, and measuring the level of complex formation.

According to some embodiments, the method for detecting or quantifying the expression of PVR comprises the steps of:

i. incubating a sample with an antibody specific to PVR or an antibody fragment thereof comprising at least an antigen-binding portion;

ii. detecting the bound PVR using a detectable probe.

According to some embodiments, the method further comprises the steps of:

iii. comparing the amount of (ii) to a standard curve obtained from a reference sample containing a known amount of PVR; and iv. calculating the amount of the PVR in the sample from the standard curve.

According to some embodiments, the method comprises indicating a subject as having a PVR positive cancer if the PVR amount is higher than a control or a given reference.

According to some particular embodiments, the sample is a body fluid or solid tissue. In some embodiments, the method is performed in-vitro or ex-vivo.

A kit for measuring the expression of PVR in biological sample is also provided comprising at least one antibody or antibody fragment as described herein and means for measuring PVR expression. In some embodiment, the kit further comprising instruction material directing the use of the kit.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The novel features described herein are set forth with particularity in the appended claims. A better understanding of the characteristics and advantages of the features described herein will be obtained by reference to the following detailed description that sets forth illustrative examples, in which the principles of the features described herein are utilized, and the accompanying drawings of which:

FIGS. 1A-1B. Affinity and competition assays of N56 substitutions. FIG. 1A. Improved affinity for PVR binding by N56E and N56D variants. Biacore assay showing relative and absolute affinity of the N56 substitutions (hIgG4 variants) to PVR-HIS tagged (Sino Cat. no. 10109-H08H). Affinity shift of >25% were considered significant. (*) Relative $K_D$s for each variant were established by dividing the $K_D$ of the substitution by the $K_D$ of the parental N56 variant (VH0VK0). FIG. 1B compares the potency of chimeric antibodies (5B9 wild type—WT, having IgG4 (S241P) HC) with variable regions carrying the LC CDR2 sequence with single amino acid substitutions (to remove a deamidation site). Potency was measured in a competition assay using parental 5B9. Relative IC50 was determined for each variant by dividing its IC50 by that of the chimeric WT antibody tested in parallel.

FIGS. 2A-2B. Improved cross-reactivity for monkey PVR binding by N56E and N56D variants. To assess maximal binding, saturating dose (10 ug/ml) of the N56 variant monoclonal antibodies (shown at the X axis) were used to stain PVR-expressing cells, and mean fluorescence intensity (MFI) values were determined by FACS analysis. The fold change was calculated by dividing the MFI of each variant by the MFI of the parental antibody (K0). (FIG. 2A) NCI-H1975 (human lung) cells and (FIG. 2B) Vero (African green monkey kidney) cells. Affinity shifts of >25% were considered significant.

FIGS. 5A-5B illustrate the affinities of humanized variants to human PVR as measured by surface plasmon resonance (SPR) (FIG. 5A) or their surface binding to PVR-expressing HEK 293 cells as measured by flow cytometry (FIG. 5B). Shown are absolute results and relative ones, using chimeric N56E mutated parental antibody (N56E VH0/Vk0) as a baseline.

FIGS. 6A-6B show the expression levels (FIG. 6A) and similarity of humanized variants to human variable domain germline sequences (FIG. 6B). The titers of individual variants after transient expression in HEK 293 EBNA cells are shown (FIG. 6A). Variable domain sequence identity of humanized heavy and light chain variants to human germ line sequence is shown (FIG. 6B).

FIG. 7A. and FIG. 7B show reduced generation of acidic species in NB1088 over time following stress test at low pH (FIG. 7A) or at high concentration at 40° C. (FIG. 7B).

Figure 10A:
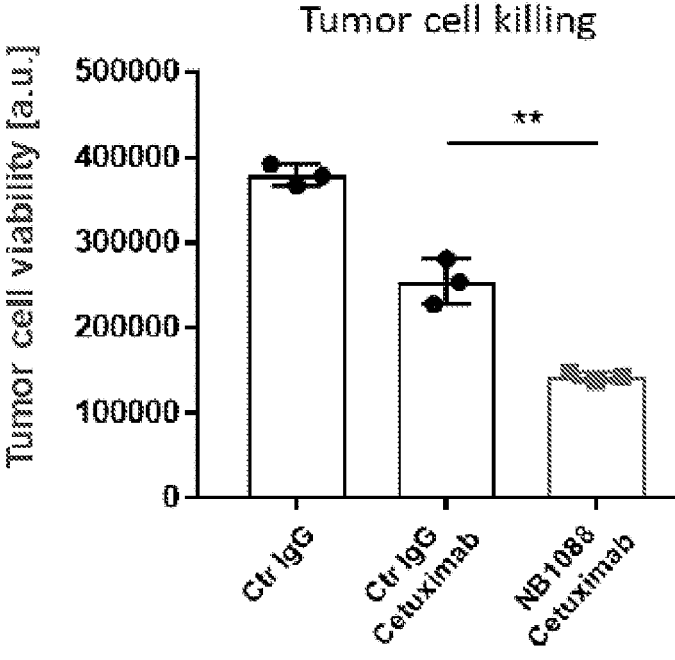
FIGS. 10A-10B illustrate that NB1088 increases antibody dependent cell cytotoxicity when combined with an endothelial growth factor receptor (EGFR) binding antibody in an EGFR expressing breast cancer cell line A549 (FIG.
Figure 10B:
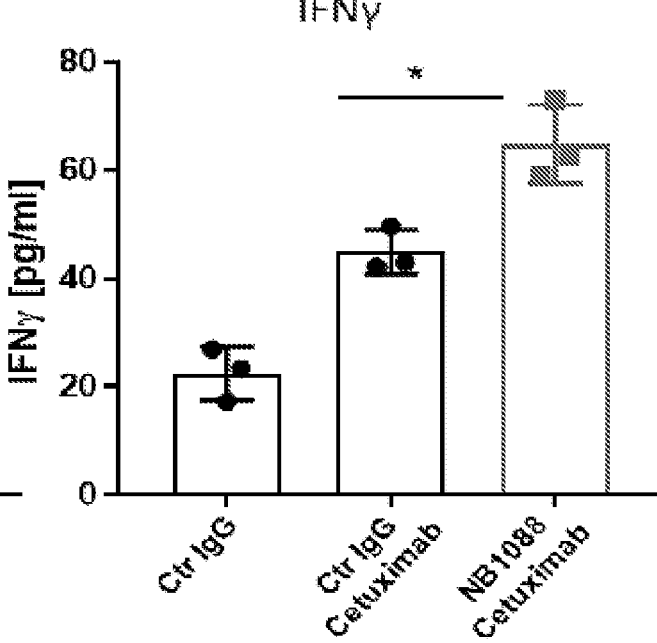

10A), and that this coincides with increased interferon gamma release (FIG. 10B). (*p<0.05, **p<0.01 one-way Anova.

Figure 11B:
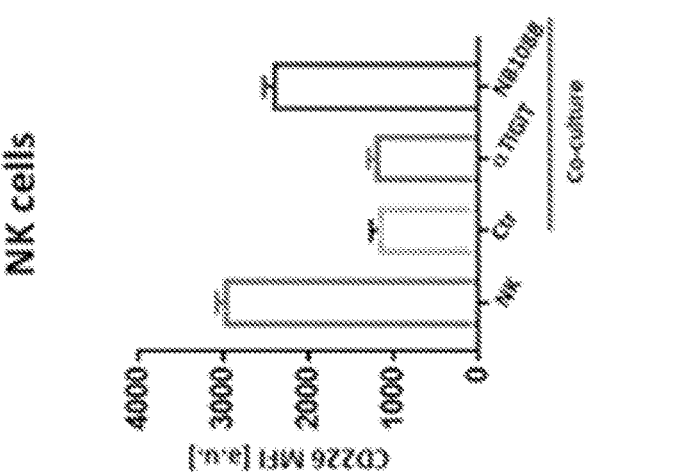
Figure 11A:
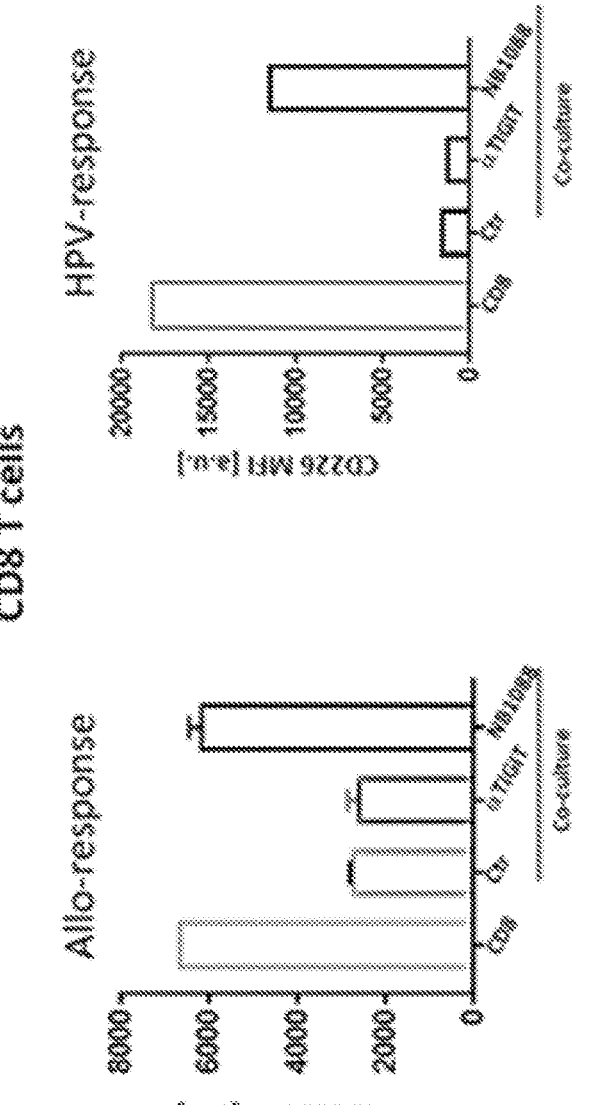

FIGS. 11A-11B illustrate that PVR expressing tumor cell lines (A549 or CaSki) can induce downregulation of CD226 expressed on CD8 T-cells (FIG. 11A) and NK-cells (FIG. 11B) that can be restored by NB1088 whereas anti-TIGIT cannot (FIGS. 11A and B). FIG. 11A shows results obtained in coculture system using an antigen specific T cell assay (human papillomavirus; HPV), or a non-specific allogenic T cell assay.

Figures 12A, 12B:
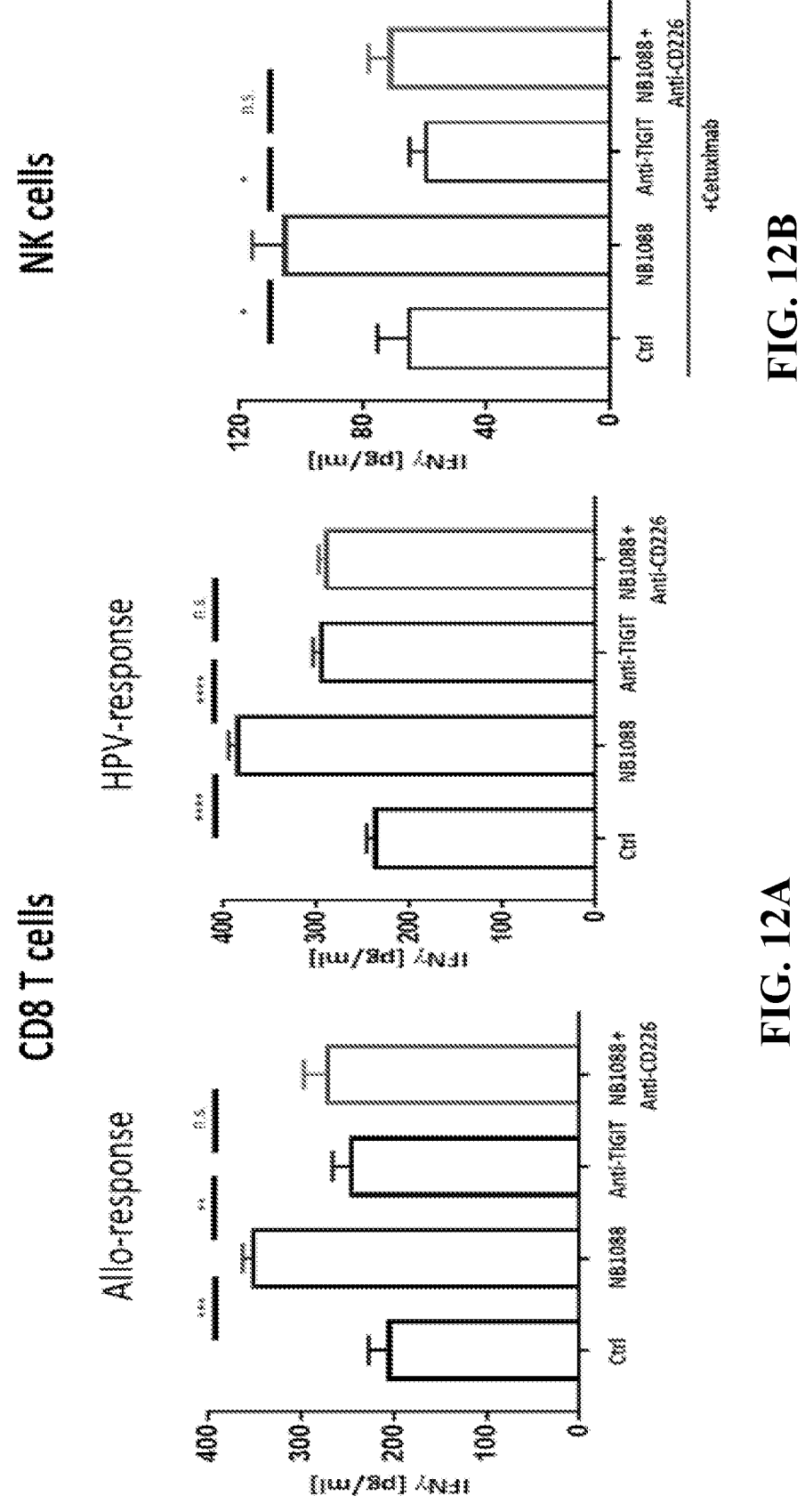

FIGS. 12A-12B illustrate NB1088 dependent increase in interferon gamma release by allo- or antigen-responsive CD8+ T cells (FIG. 12A) or that NB1088 induction of Antibody-dependent cellular cytotoxicity (ADCC)-responsive NK cells in the presence of EGFR blocking (FIG. 12B) depend on CD226 activity, and that in both cases NB1088 shows superior activity over TIGIT inhibition (both Abs are at 10 ug/ml).

Figure 13A:
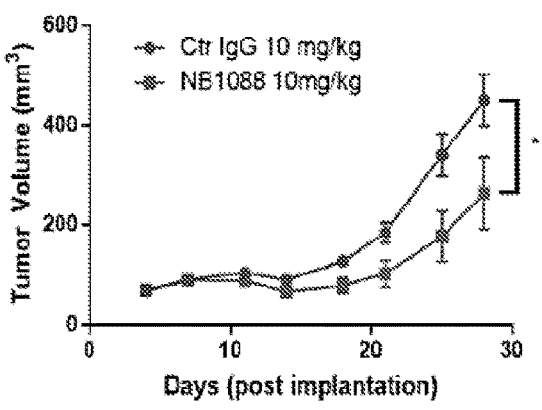
Figure 13B:
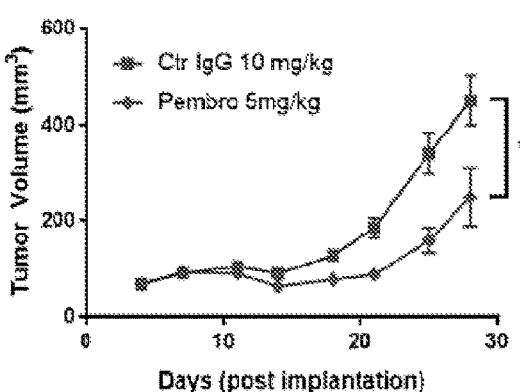
Figure 13C:
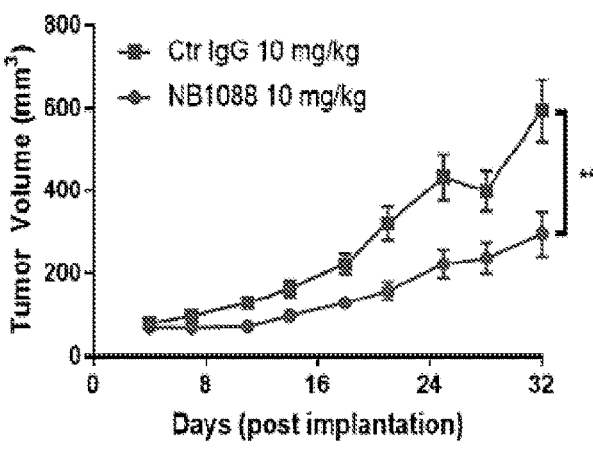
Figure 13D:
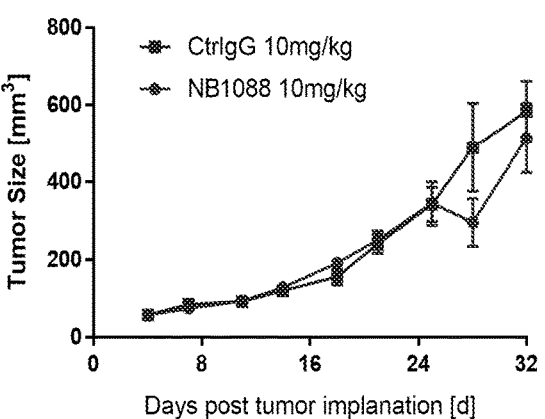
Figure 13E:
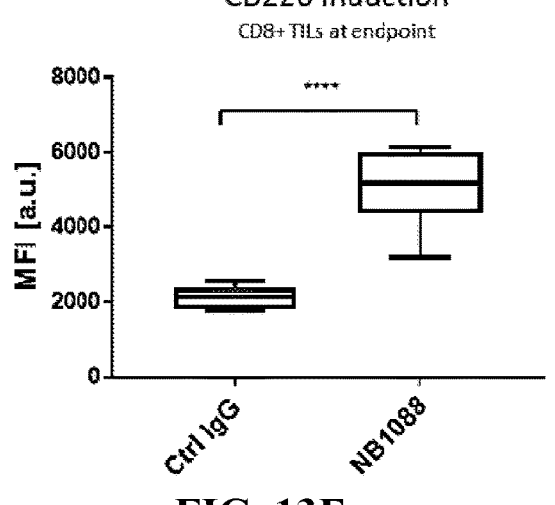

FIGS. 13A-13E illustrate that NB1088 has efficacy as monotherapy in a humanized mouse model of pancreatic cancer (FIG. 13A) that rivals pembrolizumab (anti-PD-1, given at the standard dose established for these models) (FIG. 13B) and in a humanized mouse model of lung adenocarcinoma (FIG. 13C, humanized mice), and that in this lung adenocarcinoma model efficacy depends on the presence of human immune cells (FIG. 13D, non-humanized mice) and correlates with increased CD226 expression on tumor infiltrating CD8+ T cells (FIG. 13E). (*p<0.05, ***p<0.001 by two-way Anova).

FIGS. 14A-14D relate to the model at FIGS. 13C and 13E and illustrate that NB1088 increases the frequency of interferon gamma positive (FIG. 14A) and interferon gamma/CD107a double positive (FIG. 14B) CD8 TIL cells and that NB1088 increases the frequencies of interferon gamma+/CD226+ double positive CD8 T-cells (FIG. 14D), but not interferon gamma+/CD226– single positive CD8 T-cells (FIG. 14C). *p=0.0210 ***<0.0001 unpaired TTEST.

Figures 15A, 15B:
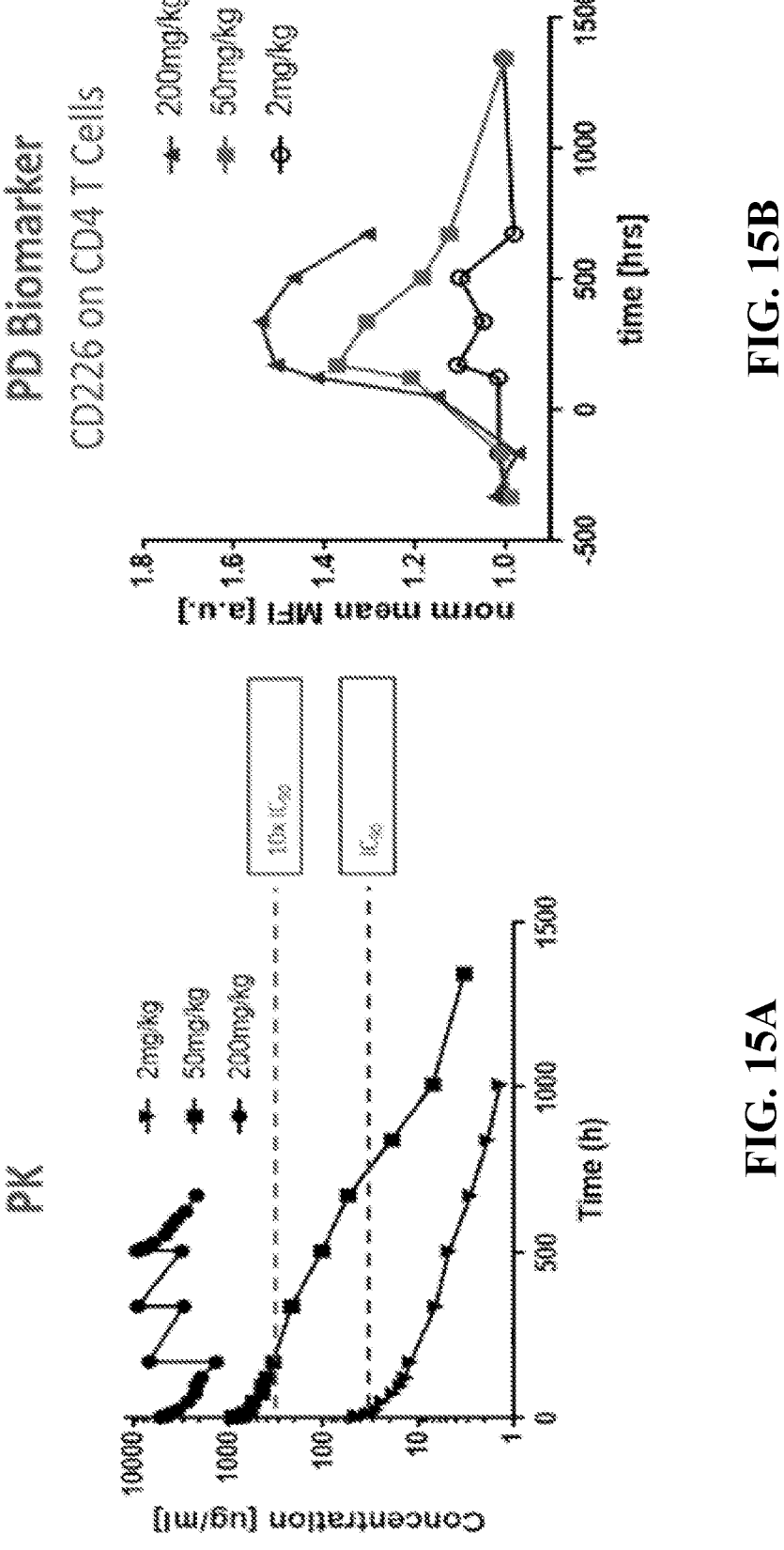

FIGS. 15A-15B illustrate the pharmacokinetics of NB1088 (FIG. 15A) and corresponding pharmacodynamic changes in CD226 surface expression (FIG. 15B) on circulating CD4 T cells in cynomolgus monkey that were treated with various doses of the antibody either once (for the 20 and 50 mg/kg doses), or 4 times, one week apart (for the 200 mg/kg dose).

Figure 16:
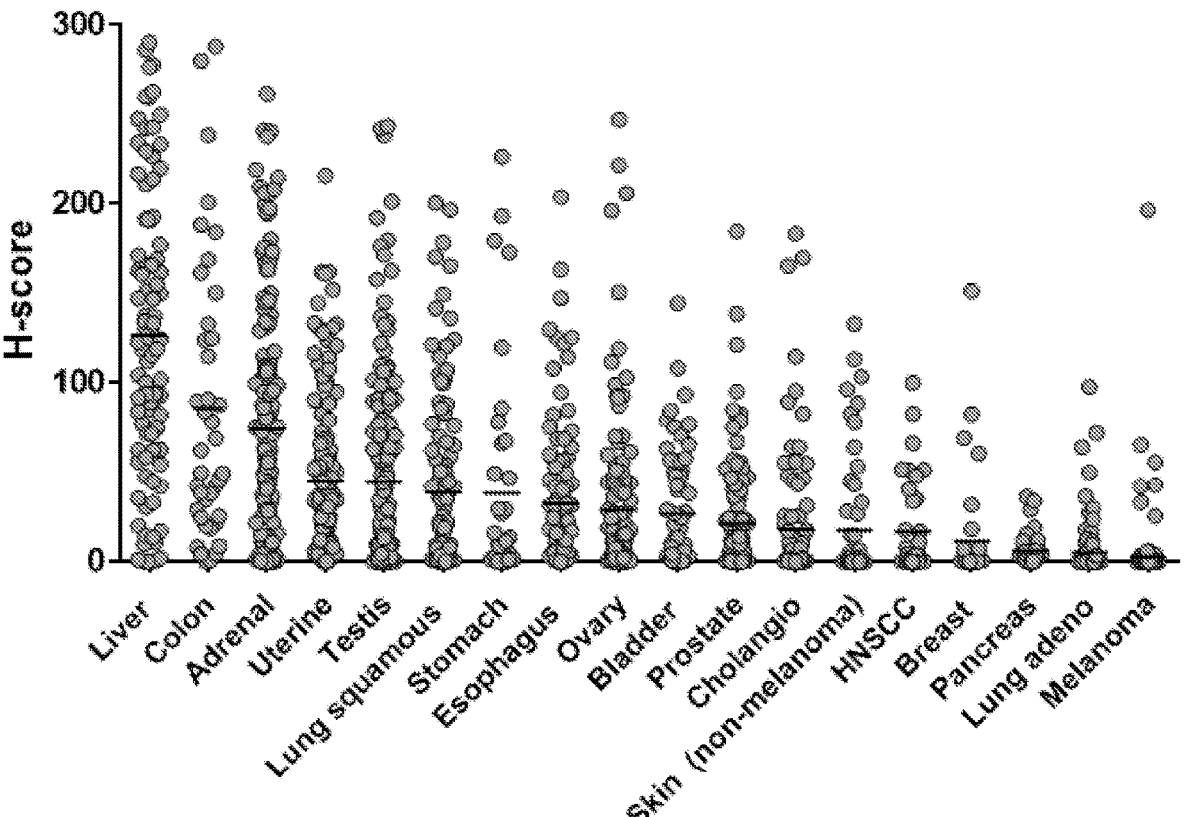

FIG. 16 shows the expression of human PVR across biopsies of different cancer types measured by immunohistochemistry and evaluated by H-score.

Figure 17:
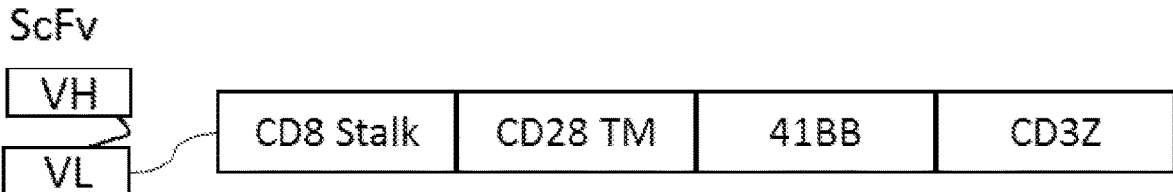

FIG. 17 is a general schematic drawing of CAR-T constructs. The scFv includes the heavy and light chains (VH and VL, respectively) of the humanized antibodies according to the invention.

Figure 18:
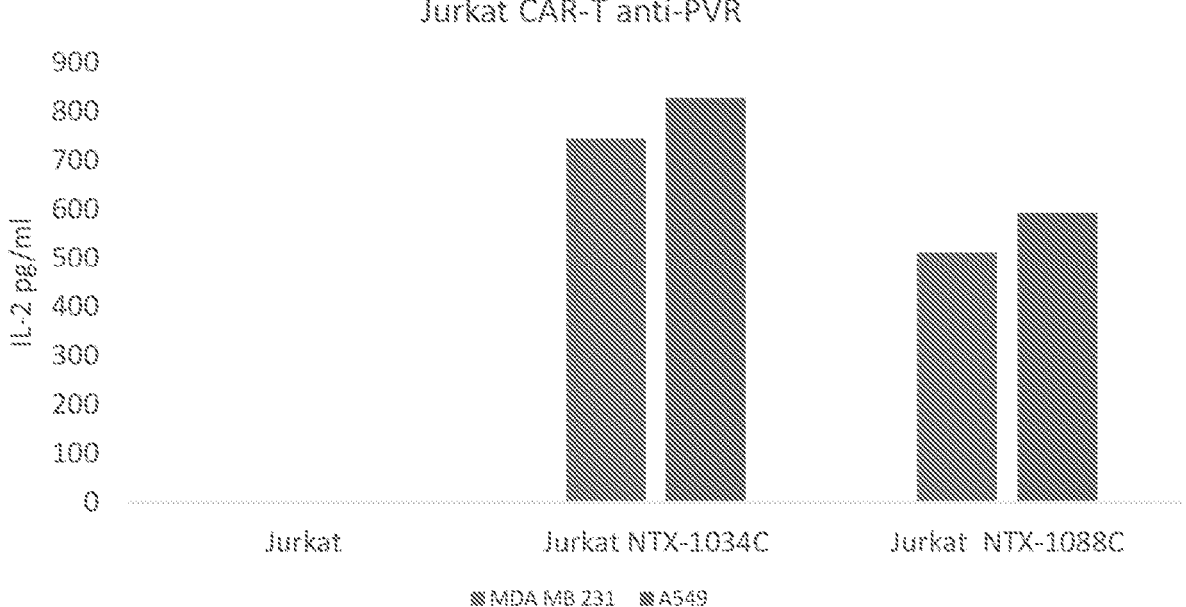

FIG. 18 Illustrates robust Interleukin 2 (IL2) secretion of Jurkat cells overexpressing αPVR CAR-T constructs over parental Jurkat cells. Parental Jurkat cells or Jurkat cells overexpressing αPVR CAR-T constructs H4K2-NTX1088C or H3K4-NTX1034C (40K cells/well) were incubated with A549 or MDA-231 cells at 1:1 E:T ratio for 24 hours IL2 secretion was quantified using Biolegend hIL-2 (cat 431804). Both CAR-T drivers increased the IL2 secretion over 100-fold over the parental Jurkat cells in presence of the indicated targets.

Figure 19A:
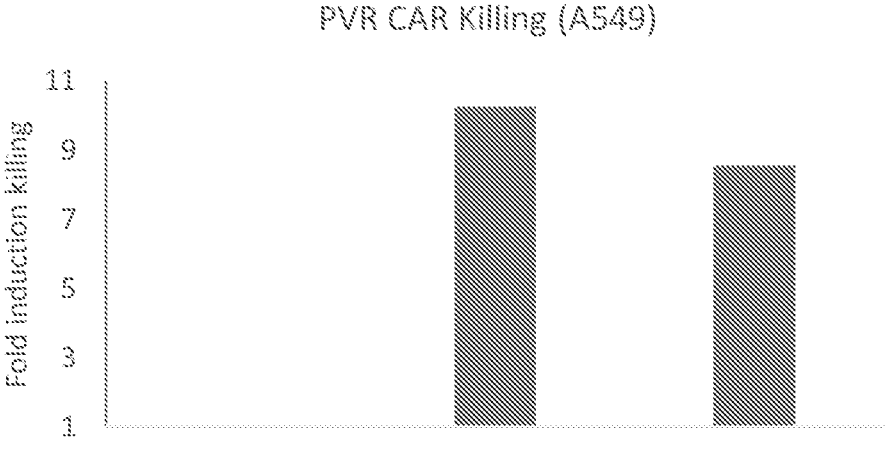
Figure 19B:
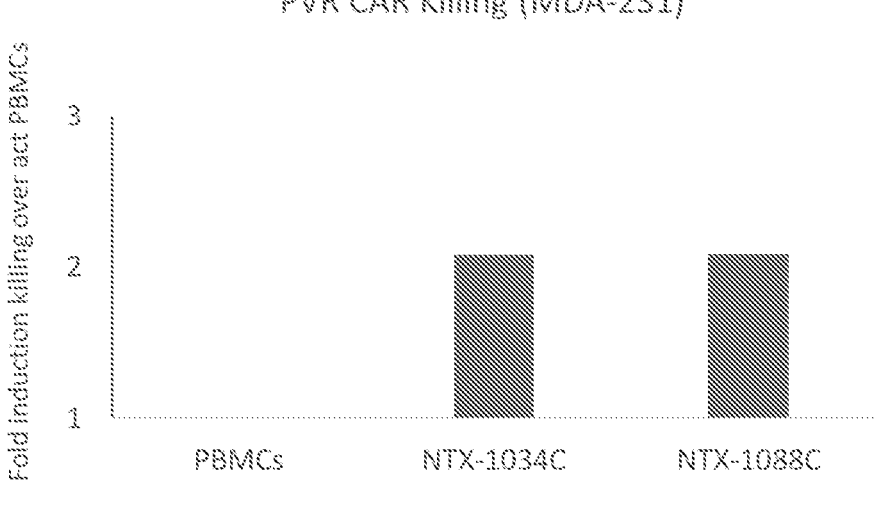
Figure 19C:
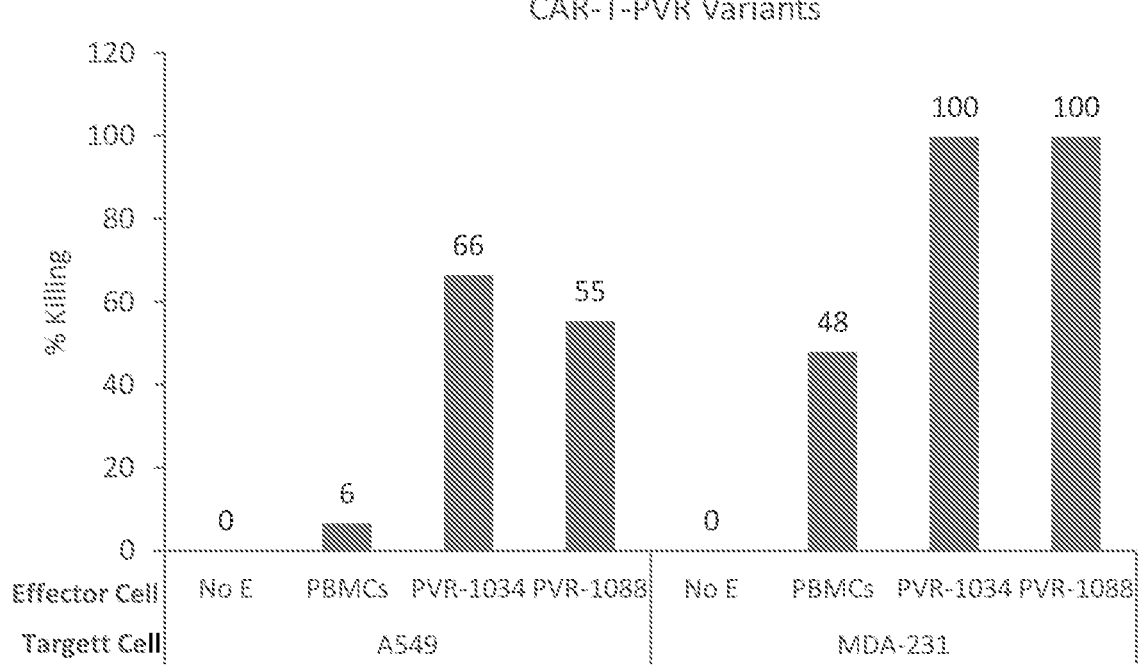

FIGS. 19A-19C Illustrate increased target cell killing by anti PVR (αPVR) CAR-T. A549 (FIG. 19A) or MDA-231 (FIG. 19B) cells (both at 200K cells) were plated in a 12 well plate with CAR-T-PVR variants NTX-1088C and NTX-1034C in NK media for 72 hours, at E:T ratios of 0.4 and 0.8 to 1, respectively (based on GFP positivity). Tumor cell killing was assessed using the standard CTG protocol (Promega G9241).

Figure 20:
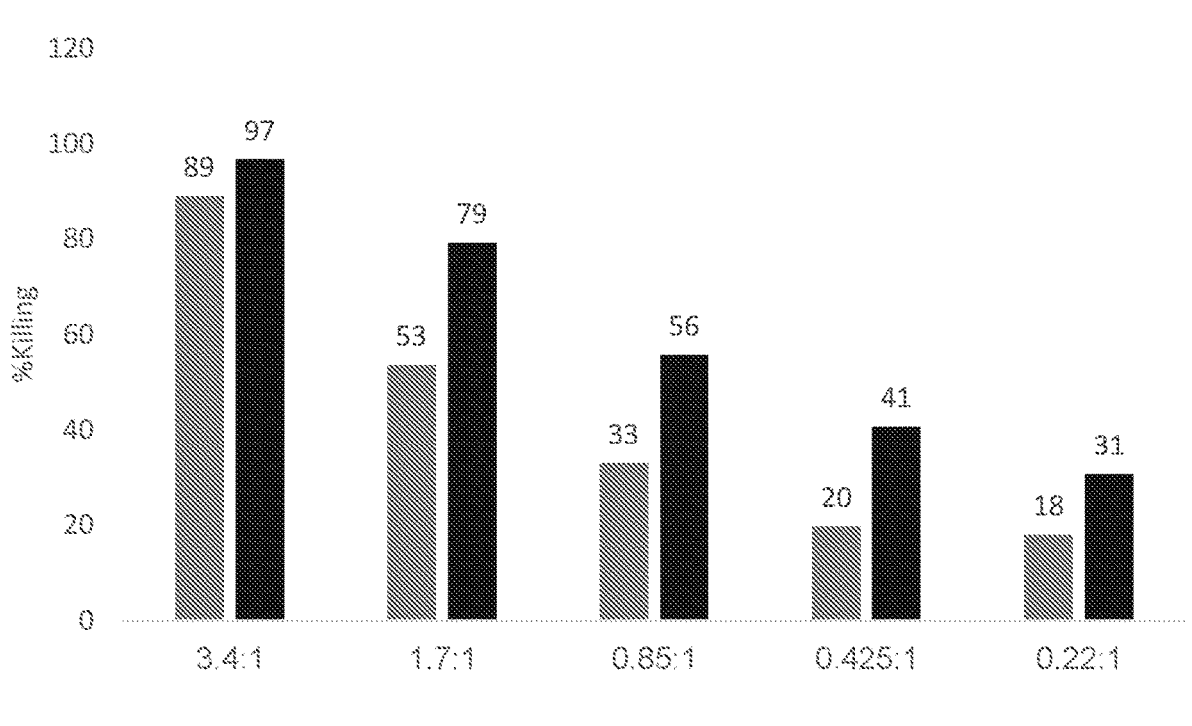

FIG. 20. Illustrates efficient hematological target cell killing by αPVR CAR-Ts. K562 (an AML model) cells were incubated with αPVR CAR-T variants NTX-1088C and NTX-1034C in RPMI+IL-2 for 18 hours at E:T ratios indicated at the X axis. Tumor cell killing was assessed using the flow cytometry. Significant target cell killing was observed for both CAR-T drivers.

DETAILED DESCRIPTION OF THE INVENTION

The present invention provides humanized monoclonal antibodies which recognize poliovirus receptor (PVR). Advantageously, the antibodies of the invention are almost fully humanized, thus avoiding the risk of adverse immune response towards the antibodies and are therefore safe for in-vivo use in humans. The antibodies of the invention are characterized by having unique CDR sequence and novel humanized framework sequences and design. More specifically, the monoclonal antibodies provided by the present invention have specific combinations of CDRs and non-fully-humanized framework sequences, and possess unique properties and improved safety and potency over known anti-PVR antibodies.

Some of the variants described herein possess increased producibility and expresses at higher levels compared to other humanized PVR antibodies comprising the same CDR regions. Also disclosed herein are methods of using these antibodies to treat a cancer in an individual.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

The term "PVR" as used herein refers to the poliovirus receptor, also known as CD155 (cluster of differentiation 155), Protein ID: Q92692 according to some embodiments. The PVR is a transmembrane glycoprotein with a N-terminal signal sequence, three extracellular immunoglobulin (Ig)-like domains, a transmembrane domain and a cytoplasmic tail. It has a molecular size of approximately 80 kDa and a structure composed of three Ig-like domains, specifically an outermost V-like domain followed by two C2-like domains. The humanized antibodies described herein have affinity to human PVR (hPVR). In some embodiments, the antibodies have some affinity to PVR proteins from other animals, in particular primates. Advantageously, the affinity for other primates, such as the African green monkey, enables further testing of the humanized antibodies for safety and efficiency in non-clinical trials. No affinity was seen for PVR from more evolutionarily distant animals, such as rodents.

As used herein the term "about" refers to an amount that is near the stated amount by 10% or less.

As used herein the term "individual," "patient," or "subject" refers to individuals diagnosed with, suspected of being afflicted with, or at-risk of developing at least one disease for which the described compositions and method are useful for treating. According to some embodiments the individual is a mammal. According to some embodiments, the mammal is a mouse, rat, rabbit, dog, cat, horse, cow, sheep, pig, goat, llama, alpaca, or yak. According to some embodiments, the individual is a human.

As used herein the term "combination" or "combination treatment" can refer either to concurrent administration of the articles to be combined or sequential administration of the articles to be combined. As described herein, when the combination refers to sequential administration of the articles, the articles can be administered in any temporal order.

The terms "cancer" and "tumor" relate to the physiological condition in mammals characterized by deregulated cell growth. Cancer is a class of diseases in which a group of cells display uncontrolled growth or unwanted growth. Cancer cells can also spread to other locations, which can lead to the formation of metastases. Spreading of cancer cells in the body can, for example, occur via lymph or blood. Uncontrolled growth, intrusion, and metastasis formation are also termed malignant properties of cancers. These malignant properties differentiate cancers from benign tumors, which typically do not invade or metastasize.

As used herein the term an "effective amount" refers to the amount of a therapeutic that causes a biological effect when administered to a mammal. Biological effects include, but are not limited to, inhibition or blockade of a receptor ligand interaction (e.g., PVR-TIGIT, PD-1-PD-L1/PD-L-2), inhibition of a signaling pathway, reduced tumor growth, reduced tumor metastasis, or prolonged survival of an animal bearing a tumor. A "therapeutic amount" is the concertation of a drug calculated to exert a therapeutic effect. A therapeutic amount encompasses the range of dosages capable of inducing a therapeutic response in a population of individuals. The mammal can be a human individual. The human individual can be afflicted with or suspected or being afflicted with a tumor.

As used herein "checkpoint inhibitor" refers a drug that inhibits a biological molecule ("checkpoint molecule") produced by an organism that negatively regulates the anti-tumor/cancer activity of T cells in the organism. Checkpoint molecules include without limitation PD-1, PD-L-1, PD-L-2, CTLA4, TIM-3, LAG-3, VISTA, SIGLEC7, PVR, TIGIT, IDO, KIR, A2AR, B7-H3, B7H4, CEACAM1, NOX2, CD112R, and CD112.

Among the provided antibodies are monoclonal antibodies, polyclonal antibodies, multispecific antibodies (for example, bispecific antibodies and polyreactive antibodies), and antibody fragments. The antibodies include antibody-conjugates and molecules comprising the antibodies, such as chimeric molecules. Thus, an antibody includes, but is not limited to, full-length, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A polyclonal antibody is a preparation that includes different antibodies of varying sequences that generally are directed against two or more different determinants (epitopes). The monoclonal antibody can comprise a human IgG1 constant region. The monoclonal antibody can comprise a human IgG4 constant region.

The term "antibody" herein is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments the CDRs of the antibodies described herein can be defined by a method selected from Kabat, Chothia, IMGT, Aho, AbM, or combinations thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology*, 6th ed., W. H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

Among the provided antibodies are antibody fragments. An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (e.g. scFv or sFv); and multispecific antibodies formed from antibody fragments. In particular embodiments, the antibodies are single-chain antibody fragments comprising a variable heavy chain region and/or a variable light chain region, such as scFvs.

The term "antigen" as used herein refers to a molecule or a portion of a molecule capable of eliciting antibody formation and being specifically bound by an antibody. An antigen may have one or more than one epitope. The specific binding referred to above is meant to indicate that the antigen will react, in a highly selective manner, with its corresponding antibody and not with the multitude of other antibodies which may be evoked by other antigens. An antigen according to some embodiments of the present invention is a human PVR.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., polypeptide linkers, and/or those that are not produced by enzyme digestion of a naturally-occurring intact antibody. According to some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. According to some embodiments, some FR residues in a humanized antibody are substituted with corresponding residues from a non-human antibody (e.g., the antibody from which the CDR residues are derived), e.g., to restore or improve antibody specificity or affinity.

A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

The terms "polypeptide" and "protein" are used interchangeably to refer to a polymer of amino acid residues, and are not limited to a minimum length. Polypeptides, including the provided antibodies and antibody chains and other peptides, e.g., linkers and binding peptides, may include amino acid residues including natural and/or non-natural amino acid residues. The terms also include post-expression modifications of the polypeptide, for example, glycosylation, sialylation, acetylation, phosphorylation, and the like. According to some embodiments, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "homologous", "homology" or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for mutagenesis by substitution include the CDRs and FRs. Amino acid substitutions may be introduced into an antibody of interest and the products screened for a desired activity, e.g., retained/improved antigen binding, decreased immunogenicity, or improved antibody-dependent cellular cytotoxicity (ADCC) or complement dependent cytotoxicity (CDC).

In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots". In some embodiments of the variant $V_H$ and $V_L$ sequences, each CDR is unaltered.

Alterations (e.g., substitutions) may be made in CDRs, e.g., to improve antibody affinity. Such alterations may be made in CDR encoding codons with a high mutation rate during somatic maturation (See e.g., Chowdhury, *Methods Mol. Biol.* 207:179-196 (2008)), and the resulting variant can be tested for binding affinity. Affinity maturation (e.g., using error-prone PCR, chain shuffling, randomization of CDRs, or oligonucleotide-directed mutagenesis) can be used to improve antibody affinity (See e.g., Hoogenboom et al. in *Methods in Molecular Biology* 178:1-37 (2001)). CDR residues involved in antigen binding may be specifically identified, e.g., using alanine scanning mutagenesis or modeling (See e.g., Cunningham and Wells *Science,* 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

In some embodiments, an antibody provided herein has a dissociation constant ($K_D$) of about 1 µM, 100 nM, 50 nM, 40 nM, 30 nM, 20 nM, 10 nM, 5 nM, 2 nM, 1 nM, 0.5 nM, 0.1 nM, 0.05 nM, 0.01 nM, or 0.001 nM or less (e.g., $10^{-8}$ M or less, e.g., from $10^{-8}$ M to $10^{-13}$ M, e.g., from $10^{-9}$ M to $10^{-13}$ M) for the antibody target, human poliovirus receptor (CD155). $K_D$ can be measured by any suitable assay. In certain embodiments, KD can be measured using surface plasmon resonance (SPR) assays (e.g., using a BIACORE®-2000 or a BIACORE®-3000).

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some embodiments, the antibodies of this disclosure are variants that possess some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. Non-limiting examples of in vitro assays to assess ADCC activity of a molecule of interest is described in U.S. Pat.

Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

Antibodies can have increased half-lives and improved binding to the neonatal Fc receptor (FcRn) (See e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See e.g., U.S. Pat. No. 7,371,826). Other examples of Fc region variants are also contemplated (See e.g., Duncan & Winter, Nature 322:738-40 (1988); U.S. Pat. Nos. 5,648,260 and 5,624,821; and WO94/29351).

In some embodiments, it may be desirable to create cysteine engineered antibodies, e.g., "thioMAbs," in which one or more residues of an antibody are substituted with cysteine residues. According to some embodiments, the substituted residues occur at accessible sites of the antibody. Reactive thiol groups can be positioned at sites for conjugation to other moieties, such as drug moieties or linker drug moieties, to create an immunoconjugate. In some embodiments, any one or more of the following residues may be substituted with cysteine: V205 (Kabat numbering) of the light chain; A118 (EU numbering) of the heavy chain; and S400 (EU numbering) of the heavy chain Fc region.

In some embodiments, an antibody provided herein may be further modified to contain additional nonproteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone)polyethylene glycol, polypropylene glycol homopolymers, polypropylen oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if two or more polymers are attached, they can be the same or different molecules.

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large-scale cell culture are known in the art. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NSO murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

In certain embodiments, described herein, is a master cell bank comprising: (a) a mammalian cell line comprising a nucleic acid encoding an antibody described herein integrated at a genomic location; and (b) a cryoprotectant. In certain embodiments, the cryoprotectant comprises glycerol. In certain embodiments, the master cell bank comprises: (a) a CHO cell line comprising a nucleic acid encoding an antibody with (i) a heavy chain amino acid sequence set forth by any one of SEQ ID NOs: 1, 3, 4, 5 or 6; and (ii) a light chain amino acid sequence set forth by any one of SEQ ID NOs: 2, 7, 8 or 9 integrated at a genomic location; and (b) a cryoprotectant. In certain embodiments, the cryoprotectant comprises glycerol. In certain embodiments, the master cell bank is contained in a suitable vial or container able to withstand freezing by liquid nitrogen.

Also described herein are methods of making an antibody described herein. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

Antibodies Described Herein

In a certain aspect described herein is an anti-human PVR (anti-hPVR) antibody or antigen binding fragment thereof. In certain embodiments, the antibody or antigen binding fragment thereof binds to the human PVR at the PVR-TIGIT interface. In certain embodiments, the anti-hPVR antibody or antigen binding fragment thereof is able to compete with any one or more of TIGIT, CD96, and CD226.

In certain embodiments, the $EC_{50}$ of a humanized antibody or antigen binding fragment thereof for binding human PVR is less than about 10 nM, 9 nM, 8 nM, 7 nM, 6 nM, 5 nM, 4 nM, 3 nM, 2 nM, 1 nM, 0.5 nM, 0.1 nM, 0.05 nM, or 0.01 nM. In certain embodiments, the $EC_{50}$ of the hPVR antibody for binding to PVR is between about 5 nM and 1 nM, between about 5 nM and about 2 nM, between about 4 nM and about 2 nM, between about 4 nM and about 3 nM, or between about 3 nM and about 2 nM.

Half maximal effective concentration ($EC_{50}$) refers to the concentration of the antibody which induces a response halfway between the baseline and maximum after a specified exposure time.

According to some embodiments, the antibody is a recombinant antibody. According to specific embodiments, the antibody is a recombinant humanized monoclonal antibody.

According to some embodiments, the humanized antibody or antigen binding fragment thereof comprises a heavy chain sequence selected from the group consisting of SEQ ID NO: 1, SEQ ID NO: 3, SEQ ID NO: 4, SEQ ID NO: 5, and SEQ ID NO: 6.

According to some embodiments, the humanized antibody or antigen binding fragment thereof comprises a light chain sequence selected from the group consisting of SEQ ID NO: 2, SEQ ID NO: 7, SEQ ID NO: 8, and SEQ ID NO: 9.

According to some embodiments, the humanized antibody or antigen binding fragment thereof is NB1088 (SEQ ID NO: 1 and SEQ ID NO: 2).

In one aspect described herein is a humanized antibody or antigen binding fragment thereof, wherein the antibody or antigen binding fragment thereof comprises a heavy chain and a light chain, wherein the heavy chain comprises an amino acid sequence at least about 90% identical to a sequence selected from the group consisting of SEQ ID NO: 1, SEQ ID NO: 3, SEQ ID NO: 4, SEQ ID NO: 5 and SEQ ID NO: 6; and wherein the light chain comprises an amino acid sequence at least about 90% identical to a sequence selected from the group consisting of SEQ ID NO: 2, SEQ ID NO: 7, SEQ ID NO: 8 and SEQ ID NO: 9, wherein the antibody or antigen binding fragment thereof binds to human poliovirus receptor (CD155).

In another aspect described herein is a humanized antibody or antigen binding fragment thereof, wherein the antibody or antigen binding fragment thereof comprises a heavy chain and an immunoglobulin light chain, wherein the heavy chain comprises an amino acid sequence at least about 90% identical to that set forth in SEQ ID NO: 1, and wherein the light chain comprises an amino acid sequence at least about 90% identical to that set forth in SEQ ID NO: 2, wherein the antibody or antigen binding fragment thereof binds to human poliovirus receptor (CD155).

In certain embodiments, described herein is a humanized antibody or antigen binding fragment thereof, wherein the antibody or antigen binding fragment thereof comprises a heavy chain and a light chain, wherein the heavy chain comprises an amino acid sequence at least about 95% identical to a sequence selected from the group consisting of SEQ ID NO: 1, SEQ ID NO: 3, SEQ ID NO: 4, SEQ ID NO: 5 and SEQ ID NO: 6; and wherein the light chain comprises an amino acid sequence at least about 95% identical to a sequence selected from the group consisting of SEQ ID NO:

2, SEQ ID NO: 7, SEQ ID NO: 8 and SEQ ID NO: 9, wherein the antibody or antigen binding fragment thereof binds to human poliovirus receptor (CD155).

In certain embodiments, described herein is a humanized antibody or antigen binding fragment thereof, wherein the antibody or antigen binding fragment thereof comprises a heavy chain and a light chain, wherein the heavy chain comprises an amino acid sequence at least about 95%, 96%, 97%, 98%, or 99% identical to a sequence selected from the group consisting of SEQ ID NO: 1, SEQ ID NO: 3, SEQ ID NO: 4, SEQ ID NO: 5 and SEQ ID NO: 6, and wherein the light chain comprises an amino acid sequence at least about 95%, 96%, 97%, 98%, or 99% identical to a sequence selected from the group consisting of SEQ ID NO: 2, SEQ ID NO: 7, SEQ ID NO: 8 and SEQ ID NO: 9, wherein the antibody or antigen binding fragment thereof binds to human poliovirus receptor (CD155). Each possibility represents a separate embodiment of the invention.

In certain embodiments, described herein is a humanized antibody or antigen binding fragment thereof, wherein the antibody or antigen binding fragment thereof comprises a heavy chain and a light chain, wherein the heavy chain comprises an amino acid sequence at least about 98% identical to that set forth in SEQ ID NO: 1, and wherein the light chain comprises an amino acid sequence at least about 98% identical to that set forth in SEQ ID NO:2, wherein the antibody or antigen binding fragment thereof binds to human poliovirus receptor (CD155).

In certain embodiments, described herein is a humanized antibody or antigen binding fragment thereof, wherein the antibody or antigen binding fragment thereof comprises a heavy chain and a light chain, wherein the heavy chain comprises an amino acid sequence at least about 99% identical to that set forth in SEQ ID NO: 1, and wherein the light chain comprises an amino acid sequence at least about 99% identical to that set forth in SEQ ID NO:2, wherein the antibody or antigen binding fragment thereof binds to human poliovirus receptor (CD155).

In certain embodiments, described herein is a humanized antibody or antigen binding fragment thereof, wherein the antibody or antigen binding fragment thereof comprises a heavy chain and a light chain, wherein the heavy chain comprises an amino acid sequence identical to that set forth in SEQ ID NO: 1, and wherein the light chain comprises an amino acid sequence identical to that set forth in SEQ ID NO:2, wherein the antibody or antigen binding fragment thereof binds to human poliovirus receptor(CD155).

According to some embodiments, the antibody or antigen binding fragment thereof comprises the heavy chain sequence set forth in SEQ ID NO: 1, and the light chain sequence set forth in SEQ ID NO: 7. According to some embodiments, the antibody or antigen binding fragment thereof comprises the heavy chain sequence set forth in SEQ ID NO: 1, and the light chain sequence set forth in SEQ ID NO: 8. According to some embodiments, the antibody or antigen binding fragment thereof comprises the heavy chain sequence set forth in SEQ ID NO: 1, and the light chain sequence set forth in SEQ ID NO: 9. According to some embodiments, the antibody or antigen binding fragment thereof comprises the heavy chain sequence set forth in SEQ ID NO: 3, and the light chain sequence set forth in SEQ ID NO: 2. According to some embodiments, the antibody or antigen binding fragment thereof comprises the heavy chain sequence set forth in SEQ ID NO: 3, and the light chain sequence set forth in SEQ ID NO: 7. According to some embodiments, the antibody or antigen binding fragment thereof comprises the heavy chain sequence set forth in SEQ ID NO: 3, and the light chain sequence set forth in SEQ ID NO: 8. According to some embodiments, the antibody or antigen binding fragment thereof comprises the heavy chain sequence set forth in SEQ ID NO: 3, and the light chain sequence set forth in SEQ ID NO: 9. According to some embodiments, the antibody or antigen binding fragment thereof comprises the heavy chain sequence set forth in SEQ ID NO: 4, and the light chain sequence set forth in SEQ ID NO: 2. According to some embodiments, the antibody or antigen binding fragment thereof comprises the heavy chain sequence set forth in SEQ ID NO: 4, and the light chain sequence set forth in SEQ ID NO: 7. According to some embodiments, the antibody or antigen binding fragment thereof comprises the heavy chain sequence set forth in SEQ ID NO: 4, and the light chain sequence set forth in SEQ ID NO: 8. According to some embodiments, the antibody or antigen binding fragment thereof comprises the heavy chain sequence set forth in SEQ ID NO: 4, and the light chain sequence set forth in SEQ ID NO: 9. According to some embodiments, the antibody or antigen binding fragment thereof comprises the heavy chain sequence set forth in SEQ ID NO: 5, and the light chain sequence set forth in SEQ ID NO: 2. According to some embodiments, the antibody or antigen binding fragment thereof comprises the heavy chain sequence set forth in SEQ ID NO: 5, and the light chain sequence set forth in SEQ ID NO: 7. According to some embodiments, the antibody or antigen binding fragment thereof comprises the heavy chain sequence set forth in SEQ ID NO: 5, and the light chain sequence set forth in SEQ ID NO: 8. According to some embodiments, the antibody or antigen binding fragment thereof comprises the heavy chain sequence set forth in SEQ ID NO: 5, and the light chain sequence set forth in SEQ ID NO: 9. According to some embodiments, the antibody or antigen binding fragment thereof comprises the heavy chain sequence set forth in SEQ ID NO: 6, and the light chain sequence set forth in SEQ ID NO: 2. According to some embodiments, the antibody or antigen binding fragment thereof comprises the heavy chain sequence set forth in SEQ ID NO: 6, and the light chain sequence set forth in SEQ ID NO: 7. According to some embodiments, the antibody or antigen binding fragment thereof comprises the heavy chain sequence set forth in SEQ ID NO: 6, and the light chain sequence set forth in SEQ ID NO: 8. According to some embodiments, the antibody or antigen binding fragment thereof comprises the heavy chain sequence set forth in SEQ ID NO: 6, and the light chain sequence set forth in SEQ ID NO: 9.

According to some embodiments, the humanized antibody or antigen binding fragment thereof comprising a heavy chain comprises the amino acid sequence QVQLVQSGAE(L/V)KKPGASVK(I/V)SCK-ATGYTFSNYWIEW(I/V)(K/R)QAPGQGLEW(I/M)GEI-FPGSGRINFNEKFKGR(A/V)TFTADTSI(D/S)T(T/A)YM(Q/E)LS(S/R)L(T/R)SDD(S/T)AVYYCARTKIYGNSFDYWGQGT(T/L)VTVSS (SEQ ID NO: 47); and a light chain comprises the amino acid sequence DI(M/Q)MTQSPS(F/S)LSASVGDRVTITC(K/R)ASQDVGTAV(V/A)WYQQKPGKAPK(L/S)LIYWAS-SRHEGVP(D/S)RF(T/S)GSGSGTDFTLTISSLQ(S/P)EDFA(D/T)YFCQQYSRYPLTFGQGT KLEIK (SEQ ID NO: 48).

According to some embodiments, the heavy chain comprises an amino acid sequence set forth in SEQ ID NO: 47, wherein position 11 is L, or position 20 is I, or position 37 is I, or position 38 is K, or position 48 is I, or position 68 is A, or position 77 is D, or position 79 is T, or position 82 is Q, or position 85 is S, or position 87 is T, or position 91 is S, or position 114 is T, or any combination thereof. Each possibility represents a separate embodiment of the invention.

According to some embodiments, the heavy chain comprises an amino acid sequence set forth in SEQ ID NO: 47, wherein position 11 is V, or position 20 is I, or position 37 is I, or position 38 is K, or position 48 is I, or position 68 is A, or position 77 is D, or position 79 is T, or position 82 is E, or position 85 is R, or position 87 is R, or position 91 is T, or position 114 is L, or any combination thereof. Each possibility represents a separate embodiment of the invention.

According to some embodiments, the heavy chain comprises an amino acid sequence set forth in SEQ ID NO: 47, wherein position 11 is V, or position 20 is V, or position 37 is V, or position 38 is R, or position 48 is M, or position 68 is V, or position 77 is S, or position 79 is A, or position 82 is E, or position 85 is R, or position 87 is R, or position 91 is T, or position 114 is L, or any combination thereof. Each possibility represents a separate embodiment of the invention.

According to some embodiments, the heavy chain comprises an amino acid sequence set forth in SEQ ID NO: 47, wherein position 11 is V, or position 20 is V, or position 37 is I, or position 38 is K, or position 48 is I, or position 68 is V, or position 77 is S, or position 79 is T, or position 82 is E, or position 85 is R, or position 87 is R, or position 91 is T, or position 114 is L, or any combination thereof. Each possibility represents a separate embodiment of the invention.

According to some embodiments, the heavy chain comprises an amino acid sequence set forth in SEQ ID NO: 47, wherein position 11 is V, or position 20 is V, or position 37 is V, or position 38 is R, or position 48 is I, or position 68 is V, or position 77 is S, or position 79 is T, or position 82 is E, or position 85 is R, or position 87 is R, or position 91 is T, or position 114 is L, or any combination thereof. Each possibility represents a separate embodiment of the invention.

According to some embodiments, the light chain comprises an amino acid sequence set forth in SEQ ID NO: 48, wherein position 3 is M, or position 10 is F, or position 24 is K, or position 34 is V, or position 46 is L, or position 60 is D, or position 63 is T, or position 80 is S, or position 85 is D, or any combination thereof. Each possibility represents a separate embodiment of the invention.

According to some embodiments, the light chain comprises an amino acid sequence set forth in SEQ ID NO: 48, wherein position 3 is Q, or position 10 is S, or position 24 is K, or position 34 is V, or position 46 is L, or position 60 is D, or position 63 is S, or position 80 is P, or position 85 is D, or any combination thereof. Each possibility represents a separate embodiment of the invention.

According to some embodiments, the light chain comprises an amino acid sequence set forth in SEQ ID NO: 48, wherein position 3 is Q, or position 10 is S, or position 24 is R, or position 34 is V, or position 46 is L, or position 60 is S, or position 63 is S, or position 80 is P, or position 85 is T, or any combination thereof. Each possibility represents a separate embodiment of the invention.

According to some embodiments, the light chain comprises an amino acid sequence set forth in SEQ ID NO: 48, wherein position 3 is Q, or position 10 is S, or position 24 is R, or position 34 is A, or position 46 is L, or position 60 is S, or position 63 is S, or position 80 is P, or position 85 is T, or any combination thereof. Each possibility represents a separate embodiment of the invention.

According to some embodiments, the humanized antibody or antigen binding fragment thereof comprising a heavy chain variable region and a light chain variable region, the heavy chain comprises an amino acid sequence set forth in SEQ ID NO: 47, wherein position 11 is V, or position 20 is V, or position 37 is V, or position 38 is R, or position 48 is I, or position 68 is V, or position 77 is S, or position 79 is T, or position 82 is E, or position 85 is R, or position 87 is R, or position 91 is T, or position 114 is L, or any combination thereof; and the light chain comprises an amino acid sequence set forth in SEQ ID NO: 48, wherein position 3 is Q, or position 10 is S, or position 24 is K, or position 34 is V, or position 46 is L, or position 60 is D, or position 63 is S, or position 80 is P, or position 85 is D, or any combination thereof.

According to additional embodiments, the heavy chain CDR1 sequence is GYTFSNYWIE (SEQ ID NO: 58).

According to some embodiments the human constant regions of the antibody are selected from the group consisting of: human IgG1, human IgG2, human IgG3, and human IgG4.

According to some embodiments the human constant regions of the antibody are selected from the group consisting of: human IgG1 and human IgG4.

According to some embodiments, the humanized antibody is an IgG4 antibody comprising a heavy chain sequences set forth in SEQ ID NO: 49, or a sequence having at least 90% identity. According to some embodiments, the humanized antibody is an IgG1 comprising a heavy chain sequence set forth in SEQ ID NO: 50 or a sequence having at least 90% identity.

According to some embodiments, the humanized antibody comprising a light chain sequence set forth in SEQ ID NO: 49.

Therapeutic Methods

In certain embodiments, disclosed herein, are anti-hPVR antibodies useful for the treatment of a cancer or tumor. Treatment refers to a method that seeks to improve or ameliorate the condition being treated. With respect to cancer, treatment includes, but is not limited to, reduction of tumor volume, reduction in growth of tumor volume, increase in progression-free survival, or overall life expectancy. In certain embodiments, treatment will affect remission of a cancer being treated. In certain embodiments, treatment encompasses use as a prophylactic or maintenance dose intended to prevent reoccurrence or progression of a previously treated cancer or tumor. It is understood by those of skill in the art that not all individuals will respond equally or at all to a treatment that is administered, nevertheless these individuals are considered to be treated.

In certain embodiments, the anti-hPVR antibodies and antigen binding fragments described herein are for use in the manufacture of a medicament for or for use in a method of treating a PVR positive cancer.

In certain embodiments, the anti-hPVR antibody or antigen binding fragments described herein is for treating a cancer or tumor that is refractory to treatment with a checkpoint inhibitor as a monotherapy. Refractory cancer refers to a cancer/tumor that develops progressive disease despite treatment with the checkpoint inhibitor alone. In certain embodiments the checkpoint inhibitor is a PD-1, PD-L1, or PD-L2 inhibitor. In certain embodiments, the PD-1, PD-L1, or PD-L2 inhibitor is an antibody or antigen binding fragment that specifically binds PD-1 (CD279) comprises Pembrolizumab, Nivolumab, AMP-514, Spartalizumab, Tislelizumab (BGB-A317), or a PD-1 (CD279) binding fragment thereof. In certain embodiments PD-1, PD-L1, or PD-L2 inhibitor is a PD-L2 Fc fusion protein (e.g., AMP-224). In certain embodiments PD-1, PD-L1, or PD-L2 inhibitor comprises an antibody or PD-L1 binding fragment that specifically binds PD-L1 (CD274). In certain embodiments, the antibody or antigen binding fragment that specifically binds to PD-L1 (CD274) comprises Durvalumab (MEDI 4376), Atezolizumab, Avelumab, BMS-936559, or FAZ053, or a PD-L1 (CD274) binding fragment thereof. In certain embodiments PD-1, PD-L1, or PD-L2 inhibitor comprises an antibody or PD-L2 binding fragment thereof that specifically binds PD-L2 (CD273). In certain embodiments PD-1, PD-L1, or PD-L2 inhibitor comprises one or more small molecule inhibitor such as N-{2-[({2-methoxy-6-[(2-methyl[1,1'-biphenyl]-3-yl)methoxy]pyridin-3-yl}methyl)amino]ethyl}acetamide (BMS 202); (2-((3-cyanobenzyl)oxy)-4-((3-(2,3-dihydrobenzo[b][1,4]dioxin-6-yl)-2-methylbenzyl)oxy)-5-methylbenzyl)-D-serine hydrochloride; (2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid; 3-(4,6-dichloro-1,3,5-triazin-2-yl)-1-phenylindole; 3-(4,6-dichloro-1,3,5-triazin-2-yl)-1-phenyl-1h-indole; L-α-Glutamine, N2,N6-bis(L-seryl-L-asparaginyl-L-threonyl-L-seryl-L-α-glutamyl-L-seryl-L-phenylalanyl)-L-lysyl-L-phenylalanyl-L-arginyl-L-valyl-L-threonyl-L-glutaminyl-L-leucyl-L-alanyl-L-prolyl-L-lysyl-L-alanyl-L-glutaminyl-L-isoleucyl-L-lysyl; (2S)-1-[[2,6-dimethoxy-4-[(2-methyl[1,1'-biphenyl]-3-yl)methoxy]phenyl]methyl]-2-piperidinecarboxylic acid; Glycinamide, N-(2-mercaptoacetyl)-L-phenylalanyl-N-methyl-L-alanyl-L-asparaginyl-L-prolyl-L-histidyl-L-leucyl-N-methylglycyl-L-tryptophyl-L-seryl-L-tryptophyl-N-methyl-L-norleucyl-N-methyl-L-norleucyl-L-arginyl-L-cysteinyl-, cyclic (1→14)-thioether; or a derivative or analog thereof.

In certain embodiments, the anti-hPVR antibody or antigen binding fragments thereof are for use in combination with a PD-1, PD-L1, or PD-L2 inhibitor. In certain embodiments, the PD-1, PD-L1, or PD-L2 inhibitor is an antibody or antigen binding fragment that specifically binds PD-1 (CD279) comprises Pembrolizumab, Nivolumab, AMP-514, Spartalizumab, Tislelizumab (BGB-A317), or a PD-1 (CD279) binding fragment thereof. In certain embodiments PD-1, PD-L1, or PD-L2 inhibitor is a PD-L2 Fc fusion protein (e.g., AMP-224). In certain embodiments PD-1, PD-L1, or PD-L2 inhibitor comprises an antibody or PD-L-1 binding fragment that specifically binds PD-L-1 (CD274). In certain embodiments, the antibody or antigen binding fragment that specifically binds to PD-L-1 (CD274) comprises Durvalumab (MEDI 4376), Atezolizumab, Avelumab, BMS-936559, or FAZ053, or a PD-L-1 (CD274) binding fragment thereof. In certain embodiments PD-1, PD-L1, or PD-L2 inhibitor comprises an antibody or PD-L2 binding fragment thereof that specifically binds PD-L2 (CD273). In certain embodiments PD-1, PD-L1, or PD-L2 inhibitor comprises one or more small molecule inhibitor such as N-{2-[({2-methoxy-6-[(2-methyl[1,1'-biphenyl]-3-yl)methoxy]pyridin-3-yl}methyl)amino]ethyl}acetamide (BMS 202); (2-((3-cyanobenzyl)oxy)-4-((3-(2,3-dihydrobenzo[b][1,4]dioxin-6-yl)-2-methylbenzyl)oxy)-5-methylbenzyl)-D-serine hydrochloride; (2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid; 3-(4,6-dichloro-1,3,5-triazin-2-yl)-1-phenylindole; 3-(4,6-dichloro-1,3,5-triazin-2-yl)-1-phenyl-1h-indole; L-α-Glutamine, N2,N6-bis(L-seryl-L-asparaginyl-L-threonyl-L-seryl-L-α-glutamyl-L-seryl-L-phenylalanyl)-L-lysyl-L-phenylalanyl-L-arginyl-L-valyl-L-threonyl-L-glutaminyl-L-leucyl-L-alanyl-L-prolyl-L-lysyl-L-alanyl-L-glutaminyl-L-isoleucyl-L-lysyl; (2S)-1-[[2,6-dimethoxy-4-[(2-methyl[1,1'-biphenyl]-3-yl)methoxy]phenyl]methyl]-2-piperidinecarboxylic acid; Glycinamide, N-(2-mercaptoacetyl)-L-phenylalanyl-N-methyl-L-alanyl-L-asparaginyl-L-prolyl-L-histidyl-L-leucyl-N-methylglycyl-L-tryptophyl-L-seryl-L-tryptophyl-N-methyl-L-norleucyl-N-methyl-L-norleucyl-L-arginyl-L-cysteinyl-, cyclic (1→14)-thioether; or a derivative or analog thereof.

In certain embodiments, the anti-hPVR antibody or antigen binding fragments thereof are for use in combination with an EGFR inhibitor or an EGFR binding antibody.

In certain embodiments, the anti-hPVR antibodies or antigen binding fragments thereof are for use in treating a cancer or tumor. In certain embodiments, the cancer or tumor is a solid cancer or tumor. In certain embodiments, the cancer or tumor is a blood cancer or tumor. In certain embodiments, the cancer or tumor comprises breast, heart, lung, small intestine, colon, spleen, kidney, bladder, head, neck, ovarian, prostate, brain, pancreatic, skin, bone, bone marrow, blood, thymus, uterine, testicular, and/or liver tumors. In certain embodiments, tumors which can be treated with the antibodies of the invention comprise adenoma, adenocarcinoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, osteosarcoma, retinoblastoma, rhabdomyosarcoma, sarcoma and/or teratoma. In certain embodiments, the tumor/cancer is selected from the group of acral lentiginous melanoma, actinic keratosis, adenocarcinoma, adenoid cystic carcinoma, adenomas, adenosarcoma, adenosquamous carcinoma, astrocytic tumors, Bartholin gland carcinoma, basal cell carcinoma, bronchial gland carcinoma, capillary carcinoid, carcinoma, carcinosarcoma, cholangiocarcinoma, chondrosarcoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, gastronoma, germ line tumors, glioblastoma, glucagonoma, hemangioblastoma, hemangioendothelioma, hemangioma, hepatic adenoma, hepatic adenomatosis, hepatocellular carcinoma, insulinite, intraepithelial neoplasia, intraepithelial squamous cell neoplasia, invasive squamous cell carcinoma, large cell carcinoma, liposarcoma, lung carcinoma, lymphoblastic leukemia, lymphocytic leukemia, leiomyosarcoma, melanoma, malignant melanoma, malignant mesothelial tumor, nerve sheath tumor, medulloblastoma, medulloepithelioma, mesothelioma, mucoepidermoid carcinoma, myeloid leukemia, neuroblastoma, neuroepithelial adenocarcinoma, nodular melanoma, osteosarcoma, ovarian carcinoma, papillary serous adenocarcinoma, pituitary tumors, plasmacytoma, pseudosarcoma, prostate carcinoma, pulmonary blastoma, renal cell carcinoma, retinoblastoma, rhabdomyosarcoma, sarcoma, serous carcinoma, squamous cell carcinoma, small cell carcinoma, soft tissue carcinoma, somatostatin secreting tumor, squamous carcinoma, squamous cell carcinoma, undifferentiated carcinoma, uveal melanoma, verrucous carcinoma, vagina/vulva carcinoma, VlPpoma, and Wilm's tumor. In certain embodiments, the tumor/cancer to be treated with one or more antibodies of the invention comprise brain cancer, head and neck cancer, colorectal carcinoma, acute myeloid leukemia, pre-B-cell acute lymphoblastic leukemia, bladder cancer, astrocytoma, preferably grade II, III or IV astrocytoma, glioblastoma, glioblastoma multiforme, small cell cancer, and non-small cell cancer, preferably non-small cell lung cancer, lung adenocarcinoma, metastatic melanoma, androgen-independent metastatic prostate cancer, androgen-dependent metastatic prostate cancer, prostate adenocarcinoma, and breast cancer, preferably breast ductal cancer, and/or breast carcinoma. In certain embodiments, the cancer treated with the antibodies of this disclosure comprises glioblastoma. In certain embodiments, the cancer treated with one or more antibodies of this disclosure comprises pancreatic cancer. In certain embodiments, the cancer treated with one or more antibodies of this disclosure comprises ovarian cancer. In certain embodiments, the cancer treated with one or more antibodies of this disclosure comprises lung cancer. In certain embodiments, the cancer treated with one or more antibodies of this disclosure comprises prostate cancer. In certain embodiments, the cancer treated with one or more antibodies of this disclosure comprises colon cancer. In certain embodiments, the cancer treated comprises glioblastoma, pancreatic cancer, ovarian cancer, colon cancer, prostate cancer, or lung cancer. In a certain embodiment, the cancer is refractory to other treatment. In a certain embodiment, the cancer treated is relapsed. In a certain embodiment, the cancer is a relapsed/refractory glioblastoma, pancreatic cancer, ovarian cancer, colon cancer, prostate cancer, or lung cancer.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered, its persistence in the blood circulation, and the judgment of the treating physician.

In certain embodiments, the antibodies can be administered to a subject in need thereof by any route suitable for the administration of antibody-containing pharmaceutical compositions, such as, for example, subcutaneous, intraperitoneal, intravenous, intramuscular, intratumoral, or intracerebral, etc. In certain embodiments, the antibodies are administered intravenously. In certain embodiments, the antibodies are administered subcutaneously. In certain embodiments, the antibodies are administered intratumoral. In certain embodiments, the antibodies are administered on a suitable dosage schedule, for example, weekly, twice weekly, monthly, twice monthly, once every two weeks, once every three weeks, or once a month etc. In certain embodiments, the antibodies are administered once every three weeks. The antibodies can be administered in any therapeutically effective amount. In certain embodiments, the therapeutically acceptable amount is between about 0.1 mg/kg and about 50 mg/kg. In certain embodiments, the therapeutically acceptable amount is between about 1 mg/kg and about 40 mg/kg. In certain embodiments, the therapeutically acceptable amount is between about 5 mg/kg and about 30 mg/kg. Therapeutically effective amounts include amounts are those sufficient to ameliorate one or more symptoms associated with the disease or affliction to be treated.

The antibodies of the present invention can be used in CAR-based adoptive immunotherapies that utilizes engineered lymphocytes comprising the CAR for treating cancer. CAR-T system is described herein as a non-limiting example.

The T cell therapy utilizes a chimeric antigen receptor (CAR) in the treatment of cancer or tumors (i.e., CAR-T cell therapy). CAR-T cell therapy is a cellular immunotherapy which involves administration to a cancer patient genetically engineered T-cells that act on tumor cells and cause apoptosis of the tumor cells. The genetically engineered T cells are prepared by expressing on a T cell a CAR having variable regions of an antibody (VL and VH) combined with an intracellular domain, such as fragment of a CD3ζ chain sequence, using gene transfer technique. CAR is a general term for a chimeric protein in which a light chain and a heavy chain of a variable region of a monoclonal antibody specific for a tumor antigen are linked to each other, which are then linked to a T-cell receptor (TCR) chain at the C-terminal side.

According to some embodiments, the CAR comprises at least one protein domain selected from the group consisting of a CD8 Stalk domain, a CD28 TM domain, a 41BB domain, and a CD3ζ domain. According to some embodiments, the CAR comprises a CD8 Stalk domain. According to some embodiments, the CAR comprises a CD28 TM domain. According to some embodiments, the CAR comprises a CD3ζ signaling domain. According to some embodiments, the CAR comprises a 41BB domain. According to specific embodiments, the CAR comprises a CD8 Stalk domain, a CD28 TM domain, a 41BB domain, and a CD3ζ domain.

According to some embodiments, a chimeric antigen receptor (CAR) comprising the heavy chain variable region (VH) and the light chain variable region (VL) according to the invention is provided. According to certain embodiments, a genetically modified lymphocyte having the CAR being expressed on its surface is provided. According to some specific embodiments, a genetically modified T cell having the CAR being expressed on its surface (CAR-T cell) is provided.

According to some embodiments, the CAR comprises a combination of heavy and light chain variable regions, the heavy chain variable region comprises an amino acid sequence with at least 90%, 92%, 94%, 96%, or 98% sequence identity to a sequence selected from the group consisting of SEQ ID NO: 1, SEQ ID NO: 3, SEQ ID NO: 4, SEQ ID NO: 5 and SEQ ID NO: 6; and the light chain variable region comprises an amino acid sequence with at least 90%, 92%, 94%, 96%, or 98% sequence identity to a sequence selected from the group consisting of SEQ ID NO: 2, SEQ ID NO: 7, SEQ ID NO: 8 and SEQ ID NO: 9.

According to some embodiments, the CAR comprises a heavy chain variable region comprising an amino acid sequence selected from the group consisting of SEQ ID NO: 1, SEQ ID NO: 3, SEQ ID NO: 4, SEQ ID NO: 5 and SEQ ID NO: 6, and a light chain variable region comprising an amino acid sequence selected from the group consisting of SEQ ID NO: 2, SEQ ID NO: 7, SEQ ID NO: 8 and SEQ ID NO: 9.

According to some embodiments, the CAR comprises a combination of a humanized antibody heavy and light chain variable regions, wherein the combination is selected from the group consisting of:

i. a heavy chain variable region sequence set forth in SEQ ID NO: 1 and a light chain variable region sequence set forth in SEQ ID NO: 9;

ii. a heavy chain variable region sequence set forth in SEQ ID NO: 3 and a light chain variable region sequence set forth in SEQ ID NO: 9;

iii. a heavy chain variable region sequence set forth in SEQ ID NO: 4 and a light chain variable region sequence set forth in SEQ ID NO: 9;

iv. a heavy chain variable region sequence set forth in SEQ ID NO: 5 and a light chain variable region sequence set forth in SEQ ID NO: 9; and v. a heavy chain variable region sequence set forth in SEQ ID NO: 6 and a light chain variable region sequence set forth in SEQ ID NO: 9.

According to some embodiments, the CAR comprises a heavy chain variable region sequence selected from the group consisting of SEQ ID NO: 1, 3, 4, 5, and 6, and a light chain variable region sequence set forth in SEQ ID NO: 9, a transmembrane domain, and an intracellular T cell signaling domain.

According to some embodiments, the CAR comprises a scFv sequence set forth in SEQ ID NO: 56 or SEQ ID NO: 57, or an analog thereof having at least 90%, 92%, 94%, 96%, or 98% sequence similarity to any of said sequences is provided. According to a certain aspect, the present invention provides a cell comprising the CAR described herein. According to some embodiments, the cell expresses or capable of expressing the CAR of the present invention. According to some embodiments, the cell is a lymphocyte. According to some embodiments, the cell is selected from a T cell and a natural killer (NK) cell.

According to some embodiments, a lymphocyte engineered to express the CAR described herein is provided. According to some embodiments, a T cell engineered to express the CAR described herein is provided.

According to additional embodiments, an NK cell engineered to express the CAR described herein is provided.

The present invention further discloses methods for diagnosing and prognosing cancer.

According to an aspect, the present invention provides a diagnostic and/or prognostic method of cancer or infectious disease in a subject, the method comprises the step of determining the expression level of PVR in a biological sample of said subject using at least one antibody as described herein.

Pharmaceutically Acceptable Excipients, Carriers, and Diluents

In certain embodiments the anti-PVR antibodies of the current disclosure are included in a pharmaceutical composition comprising one or more pharmaceutically acceptable excipients, carriers, and diluents. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired exposure.

In certain embodiments, the antibodies of the current disclosure are administered suspended in a sterile solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

Typically, the antibodies and fragments and conjugates thereof of the present invention comprising the antigen binding portion of an antibody or comprising another polypeptide including a peptide-mimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid. The rate of release of the molecule according to the present invention, i.e., of an antibody or antibody fragment, from such a matrix depends upon the molecular weight of the molecule, the amount of the molecule within the matrix, and the size of dispersed particles.

In certain embodiments, the antibodies of the current disclosure are shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

In certain embodiments, the lymphocytes bearing the CAR described herein are shipped/stored before use. The cells are usually cryopreserved when not used immediately. Cryopreservation methods and storage media suitable for cells bearing CAR are known in the art, see for example, Wang, et al. 2019 May; 21(5):566-578.

Also described herein are kits comprising one or more of the antibodies described herein in a suitable container and one or more additional components selected from: instructions for use; a diluent, an excipient, a carrier, and a device for administration. In some embodiments, the kit comprises means for measuring expression of human PVR.

In certain embodiments, described herein is a method of preparing a cancer treatment comprising admixing one or more pharmaceutically acceptable excipients, carriers, or diluents and an antibody of the current disclosure. In certain embodiments, described herein is a method of preparing a cancer treatment for storage or shipping comprising lyophilizing one or more antibodies of the current disclosure.

EXAMPLES

The following illustrative examples are representative of embodiments of compositions and methods described herein and are not meant to be limiting in any way.

Example 1—Improved Affinity of PVR Binding by N56E and N56D Variants

The variable region of the chimeric anti-PVR antibody 5B9, disclosed in WO2017149538, carries a deamidation sequence (Asparagine-Glycine), in CDR2 of the light chain (WASSRHNG, SEQ ID NO: 17). Seven chimeric variants were generated by introducing a point mutation at residue asparagine N56. To assess the binding affinity of the N56 substitution variants, wild type (WT) and substitution variants IgG4 (S241P) monoclonal antibodies were immobilized on Protein A capture chip. Binding was tested for the analyte PVR conjugated to Histidine tag (PVR-HIS, Sino Cat. no. 10109-H08H). Dilution range: Five point two-fold dilution from 50 nM to 3.125 nM. Conditions used: Instrument: Biacore T200 (serial no. 1909913) running Biacore T200 Evaluation Software V2.0.1. Running buffer: HBS-P+, 300 mM NaCl, 1 mg/ml BSA. Flow rate: 30 μl/min. Association: 350 s, Dissociation: 800 s. Regeneration: 10 mM glycine pH 1.5. Analysis: 1:1 binding. Relative $K_D$ for each substitution was established by dividing the $K_D$ of the substitution to the $K_D$ of the parental N56 variant (VH0VK0). Significant (>25%) improvement of affinity was noted for the N56E (Asp) and N56D (Glu) variants (FIG. 1A). The binding of chimeric variants to human PVR expressed on HEK 293 EBNA cells was assessed by flow cytometry in a competition assay using parental 5B9 antibody (WT, FIG. 1B).

Example 2—Improved Cross-Reactivity for Monkey PVR Binding by N56E and N56D Variants The binding of the N56 substitution variant antibodies to cell bound PVR of human (protein id: Q92692) and chlorocebus (African green monkey, protein id: UniProtKB-P32506) was examined. FIG. 2A depicts the relative binding of all variants, which were added in saturating concentration (10 ug/ml), to NCI-H1975 cells expressing human PVR. FIG. 2B depicts the relative binding of all variants, which were added in saturating concentration (10 ug/ml), to Vero cells expressing chlorocebus PVR. For detection, Goat anti-human-647 antibody (Jackson immunoresearch 109-606-088) was used at 1:250 dilution. Cell binding of the Abs was analyzed by FACS. The fold change was calculated by dividing the MFI of each variant by the MFI of the parental antibody (K0). Significant (>25%) increase in crossreactivity is seen for N56E and N56D variants.

Example 3—Improved NK Activation by N56E and N56T Variants

Figure 3:
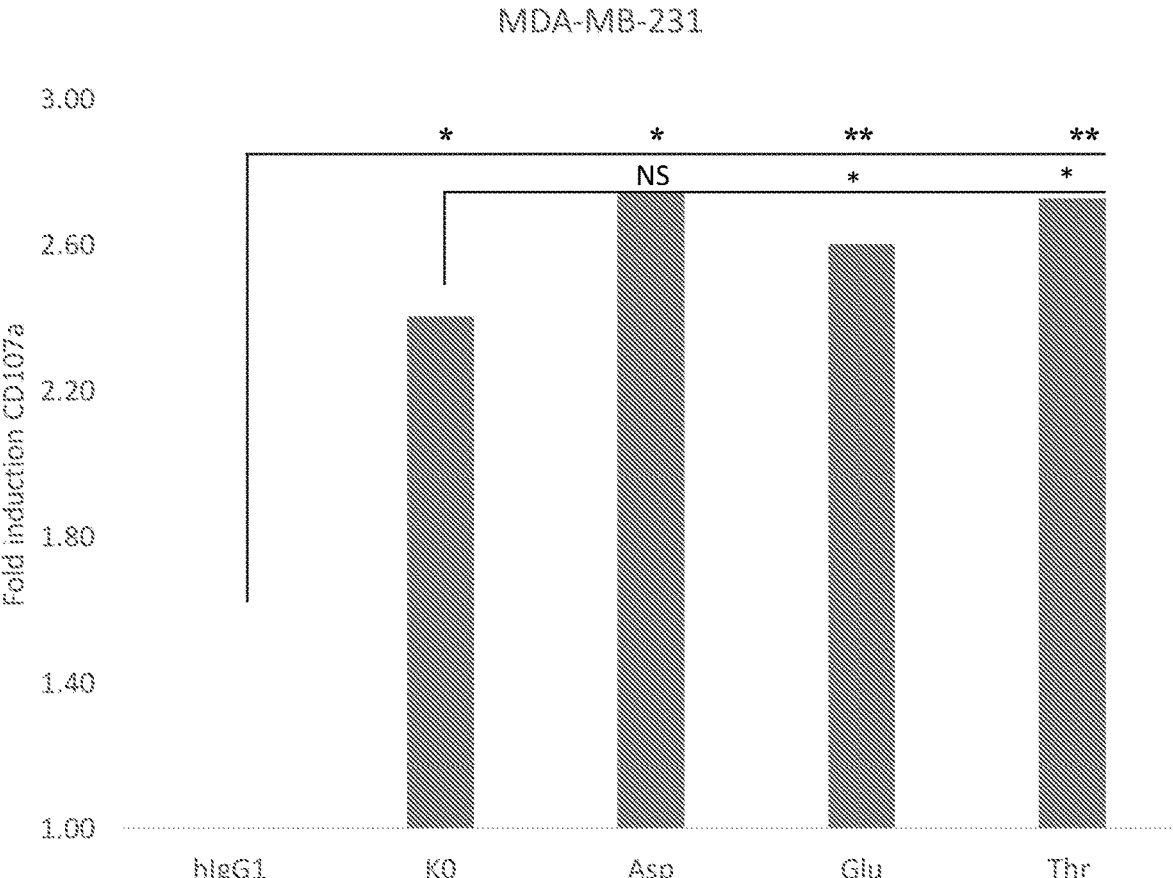
FIG. 3. Improved NK activation by N56E and N56T variants. To characterize the N56 substitution variants, a CD107a induction assay was performed using human NK cells from a healthy donor and MDA-MB-231 as target cells at 2:1 ratio. The Abs were added at 600 pM. K0 is the parental clone (N56). All variants led to significant CD107a induction (>240% over isotype IgG1). Additionally, N56 substitutions N56E & N56T significantly improved CD107a induction compared with K0. (*p<0.04, **p<0.01).

NK cells from healthy donors were incubated in presence of selected N56 substitution variants, and target breast cancer cell line (MDA-MB-231) at 2:1 E:T ratio for 2 hours at 37° C. degrees. NK cell activation was measured by the induction of surface expression of CD107a, and fold change over control IgG was calculated for each variant (Y axis). All monoclonal antibodies were used at 600 pM (0.09 ug/ml). (*p<0.04, **p<0.01 by two tailed student t-test). As shown in FIG. 3, N56E and N56T variants showed improved NK activation, compared to K0, as evidenced by CD107a elevated expression

Example 4—Improved CD8 T Cell Proliferation by N56E and N56T Variants

Human PBMCs were fluorescently labeled with CFSE (C34554 ThermoFischer) and incubated with A549 target breast cancer cells in the presence of 2.5 ul/ml PHA-L (Roche), and with the indicated antibody variants at 4 ug/ml. After incubation for 96 hrs, the immune cells were collected, stained by anti-human CD8 and analyzed by FACS. Cell proliferation of CD8+ T cells was assessed by CFSE signal intensity. CFSE levels of the IgG treated cells were set as 1.

Figure 4:
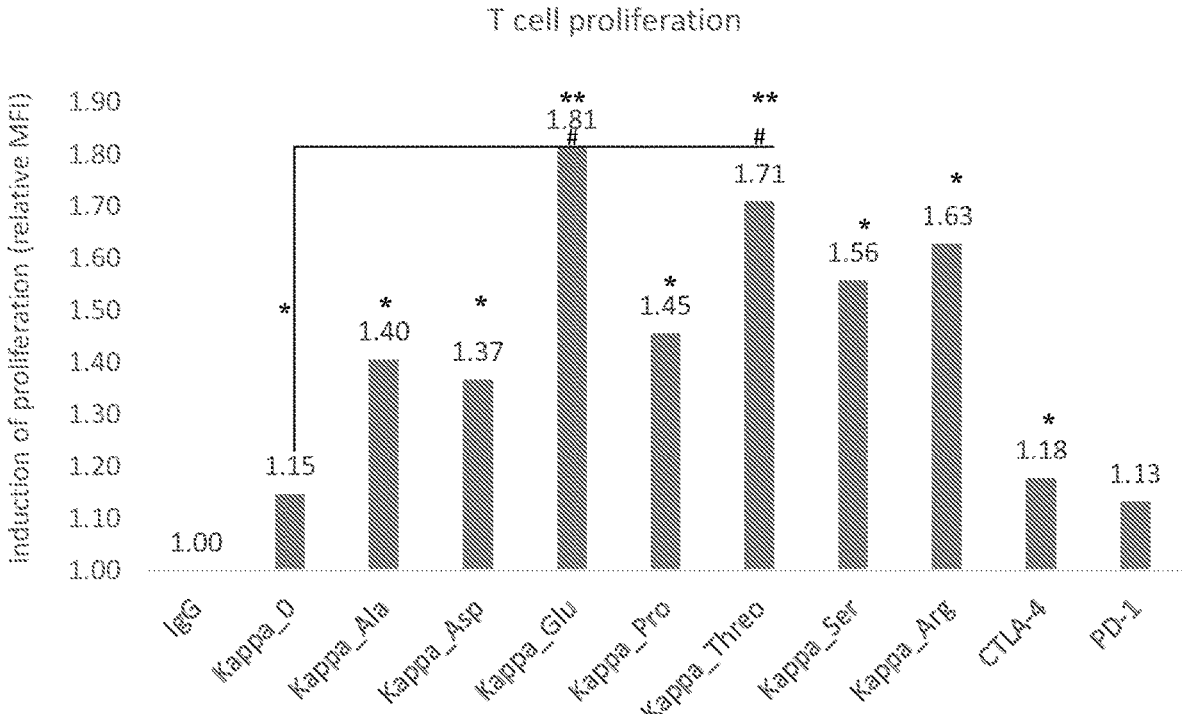
FIG. 4. Improved CD8 T cell proliferation by N56E and N56T variants. To characterize the N56 variants, T cell proliferation assay was performed. A549 cancer cells were used at 4:1 effector-to-target ratio, in presence of 2.5 ul/ml PHA-L and using CFSE labeled fresh human PBMCs. All N56 variant monoclonal antibodies (X axis) were added at 4 ug/ml and the co-culture was incubated for 96 hrs. Presented are the results of FACS analysis gated on CD8+ T cells. The relative MFI of the CFSE labeling was calculated by dividing the MFI of the of the IgG treated group with that of each variant. As increase in proliferation results in reduced CFSE signal, the Y axis depicts the reciprocal value of this ratio. N56E and N56T variants increased CD8 T cell proliferation significantly over parental clone (K0) marked by #. (*p<0.05, #<0.04, **p<0.01).

Results are presented as fold increased proliferation relative to this control. As increase in proliferation results in reduces CFSE signal, the Y axis depicts the reciprocal value of this ratio. Experiments were done in quadruplicates; Shown are results for a single PBMC donor. The data suggest that variants N56E and N56T have significantly stronger effect on the proliferation of CD8+ T cells in presence of tumor cells compared to the parental antibody (FIG. 4; *p<0.05, **p<0.01 by two tailed student t-test).

Example 5—Identification of a Humanized 5B9 Variant having Improved Producibility N56E antibody variant performed the best in the competition assay and was selected as the lead variant for humanization. Based on structural analysis, a large preliminary set of sequence segments were identified that were used to create the 5B9 humanized variants. These segments were selected and analyzed using iTope™ technology for in silico analysis of peptide binding to human MHC class II alleles (Perry et al 2008), and using the TCED™ of known antibody sequence-related T cell epitopes (Bryson et al 2010). Sequence segments that were identified as significant non-human germline binders to human MHC class II or that scored significant hits against the TCED™ were discarded. This resulted in a reduced set of segments, and combinations of these were further analyzed, as described above, to ensure that the junctions between segments did not contain potential T cell epitopes. Selected sequence segments were assembled into complete V region sequences that were devoid of significant T cell epitopes. Five heavy chain (VH1 to VH5) and 4 light chains (containing the N56E substitution) (Vκ1 to Vκ4) sequences were then chosen.

TABLE 1

| | variable regions and CDR sequences | |
|---|---|---|
| SEQ ID NO: | Sequence | Chain |
| 1 | QVQLVQSGAEVKKPGASVKVSCKATGYTFSNYWIEWVRQAPGQGLE WIGEIFPGSGRINFNEKFKGRVTFTADTSISTTYMELSRLRSDDTAVYYC ARTKIYGNSFDYWGQGTLVTVSS | VH4 |
| 2 | DIQMTQSPSSLSASVGDRVTITCKASQDVGTAVVWYQQKPGKAPKLLI YWASSRHEGVPDRFSGSGSGTDFTLTISSLQPEDFADYFCQQYSRYPLT FGQGTKLEIK | VK2 |
| 3 | QVQLVQSGAELKKPGASVKISCKATGYTFSNYWIEWIKQAPGQGLEWI GEIFPGSGRINFNEKFKGR ATFTADTSIDTTYMQLSSLTSDDSAVYYCARTKIYGNSFDYWGQGTTV TVSS | VH1 |
| 4 | QVQLVQSGAEVKKPGASVKISCKATGYTFSNYWIEWIKQAPGQGLEWI GEIFPGSGRINFNEKFKGRATFTADTSIDTTYMELSRLRSDDTAVYYCA RTKIYGNSFDYWGQGTLVTVSS | VH2 |
| 5 | QVQLVQSGAEVKKPGASVKVSCKATGYTFSNYWIEWIKQAPGQGLEW IGEIFPGSGRINFNEKFKGRVTFTADTSISTTYMELSRLRS DDTAVYYCARTKIYGNSFDYWGQGTLVTVSS | VH3 |
| 6 | QVQLVQSGAEVKKPGASVKVSCKATGYTFSNYWIEWVRQAPGQGLE WMGEIFPGSGRINFNEKFKGRVTFTADTSISTAYMELSRLRSDDTAVYY CARTKIYGNSFDYWGQGTLVTVSS | VH5 |
| 7 | DIMMTQSPSFLSASVGDRVTITCKASQDVGTAVVWYQQKPGKAPKLLI YWASSRHEGVPDRFTGSGSGTDFTLTISSLQSEDFADYFCQQYSRYPLT FGQGTKLEIK | VK1 |
| 8 | DIQMTQSPSSLSASVGDRVTITCRASQDVGTAVVWYQQKPGKAPKLLI YWASSRHEGVPSRFSGSGSGTDFTLTISSLQPEDFATYFCQQYSRYPLTF GQGTKLEIK | VK3 |
| 9 | DIQMTQSPSSLSASVGDRVTITCRASQDVGTAVAWYQQKPGKAPKSLI YWASSRHEGVPSRFSGSGSGTDFTLTISSLQPEDFATYFCQQYSRYPLTF GQGTKLEIK | VK4 |
| 10 | NYWIE | HCCDR1 |
| 11 | EIFPGSGRINFNEKFKG | HCCDR2 |
| 12 | TKIYGNSFDY | HCCDR3 |
| 13 | $X_1$ASQDVGTAV$X_2$ $X_1$ = K or R, $X_2$ = V/A | LCCDR1 |
| 14 | WASSRHE | LCCDR2 |
| 15 | QQYSRYPLT | LCCDR3 |
| 16 | QVQLQQSGAELMKPGASVKISCKATGYTFSNYWIEWIKQRPGHGLEWI GEIFPGSGRINFNEKFKGKATFTADTSSDTTYMQLSSLTSADSAVYYCA RTKIYGNSFDYWGQGTTLTVSP | VH0 5B9 |

TABLE 1-continued

| | variable regions and CDR sequences | |
|---|---|---|
| SEQ ID NO: | Sequence | Chain |
| 17 | DIMMTQSHKFMSTSVGDRVNITCKASQDVGTAVVWYQQKPGQSPKLL IYWASSRHNGVPDRFTGSGSGTDFTLTISNVQSEDLSDYFCQQYSRYPL TFGAGTKLELK | VK0 5B9 |

TABLE 2

Framework (Non-CDR) sequences of the humanized heavy chain variable regions.

| Chain | FR-H1 | FR-H2 | FR-H3 | FR-H4 |
|---|---|---|---|---|
| VH 4 | QVQLVQSGAEVKKPGASV KVSCKATGYTFS (SEQ ID NO: 18) | WVRQAPGQGLEW IG (SEQ ID NO: 19) | RVTFTADTSISTTYME LSRLRSDDTAVYYCA R (SEQ ID NO: 20) | WGQGTLVTV SS (SEQ ID NO: 21) |
| VH 1 | QVQLVQSGAELKKPGASV KISCKATGYTFS (SEQ ID NO: 22) | WIKQAPGQGLEWI G (SEQ ID NO: 23) | RATFTADTSIDTTYM QLSSLTSDDSAVYYC AR (SEQ ID NO: 24) | WGQGTTVTV SS (SEQ ID NO: 25) |
| VH 2 | QVQLVQSGAEVKKPGASV KISCKATGYTFS (SEQ ID NO: 26) | WIKQAPGQGLEWI G (SEQ ID NO: 23) | RATFTADTSIDTTYM ELSRLRSDDTAVYYC AR (SEQ ID NO: 27) | WGQGTLVTV SS (SEQ ID NO: 21) |
| VH 3 | QVQLVQSGAEVKKPGASV KVSCKATGYTFS (SEQ ID NO: 18) | WIKQAPGQGLEWI G (SEQ ID NO: 23) | RVTFTADTSISTTYME LSRLRSDDTAVYYCA R (SEQ ID NO: 20) | WGQGTLVTV SS (SEQ ID NO: 21) |
| VH 5 | QVQLVQSGAEVKKPGASV KVSCKATGYTFS (SEQ ID NO: 18) | WVRQAPGQGLEW MG (SEQ ID NO: 28) | RVTFTADTSISTAYME LSRLRSDDTAVYYCA R (SEQ ID NO: 29) | WGQGTLVTV SS (SEQ ID NO: 21) |

TABLE 3

Framework (Non-CDR) sequences of the humanized light variable regions.

| Chain | FR-L1 | FR-L2 | FR-L3 | FR-L4 |
|---|---|---|---|---|
| LK 2 | DIQMTQSPSSLSASVGDR VTITC (SEQ ID NO: 30) | WYQQKPGKAPKLLIY (SEQ ID NO: 31) | GVPDRFSGSGSGTDF TLTISSLQPEDFADYF C (SEQ ID NO: 32) | FGQGTKLEI K (SEQ ID NO: 33) |
| LK 1 | DIMMTQSPSFLSASVGDR VTITC (SEQ ID NO: 34) | WYQQKPGKAPKLLIY (SEQ ID NO: 31) | GVPDRFTGSGSGTDF TLTISSLQPEDFADYF C (SEQ ID NO: 35) | FGQGTKLEI K (SEQ ID NO: 33) |
| LK 3 | DIQMTQSPSSLSASVGDR VTITC (SEQ ID NO: 30) | WYQQKPGKAPKLLIY (SEQ ID NO: 31) | GVPSRFSGSGSGTDFT LTISSLQPEDFATYFC (SEQ ID NO: 36) | FGQGTKLEI K (SEQ ID NO: 33) |
| LK 4 | DIQMTQSPSSLSASVGDR VTITC (SEQ ID NO: 30) | WYQQKPGKAPKSLIY (SEQ ID NO: 37) | GVPSRFSGSGSGTDFT LTISSLQPEDFATYFC (SEQ ID NO: 36) | FGQGTKLEI K (SEQ ID NO: 33) |

All variants were tested for binding by SPR (FIG. 5A) and variants with affinity of 2× from the parental antibody were tested for cell-surface PVR binding by flow cytometry (FIG. 5B). With the exception of variants containing Vk4, all variants showed very similar binding compared to the parental mouse/human chimeric molecule carrying the N56E substitution (IgG4(S241P) N56E_VH0/Vκ0). It is noted that the humanization removed an N-Linked glycosylation at position N20 FR1 light chain.

Figure 7A:
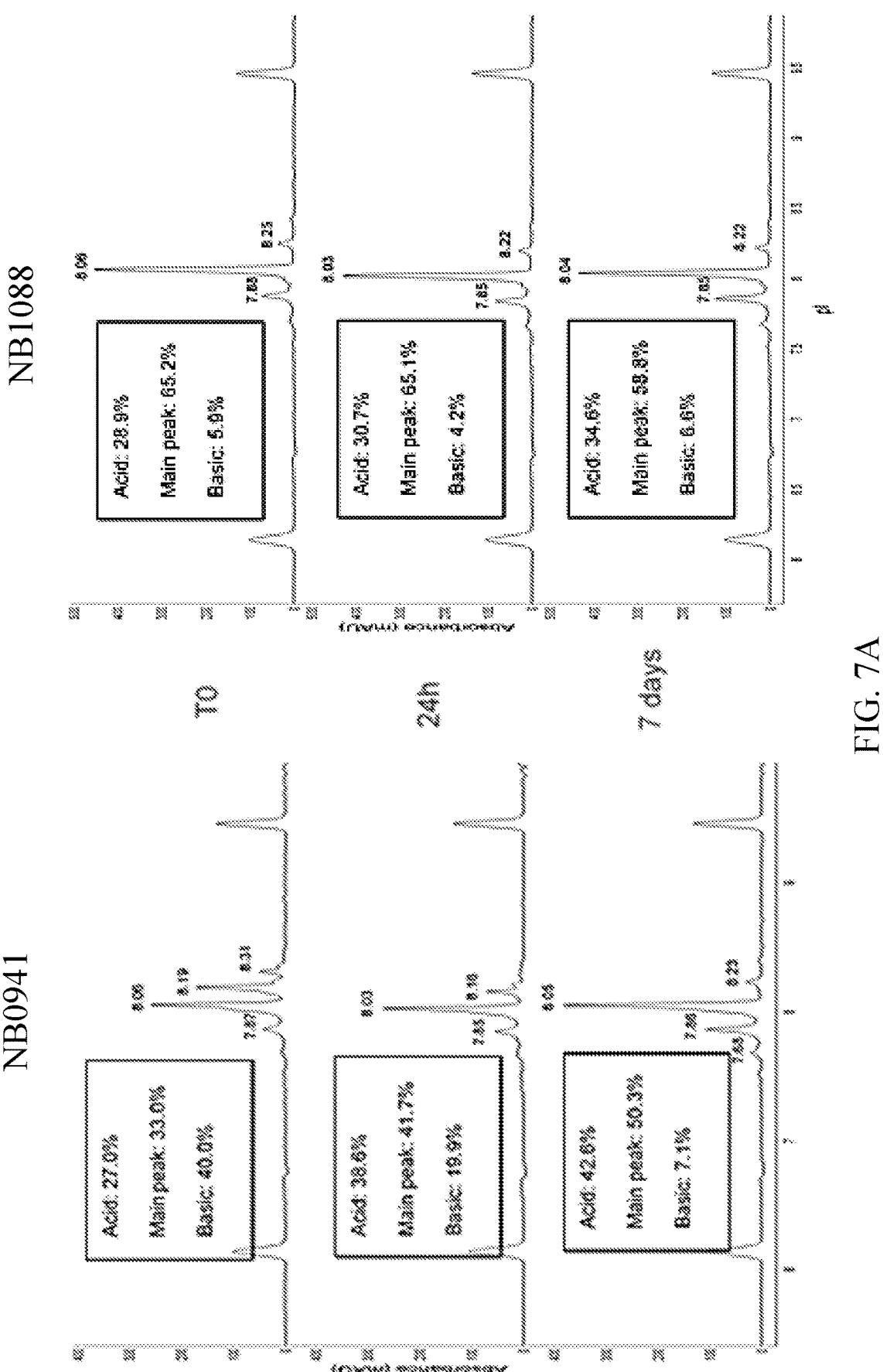
FIGS. 7A-7B compare the biophysical properties of humanized lead variant NB1088 (right column) to the humanized variant NB941 carrying the LC CDR2 5B9 WT sequence (left column).
Figure 7B:
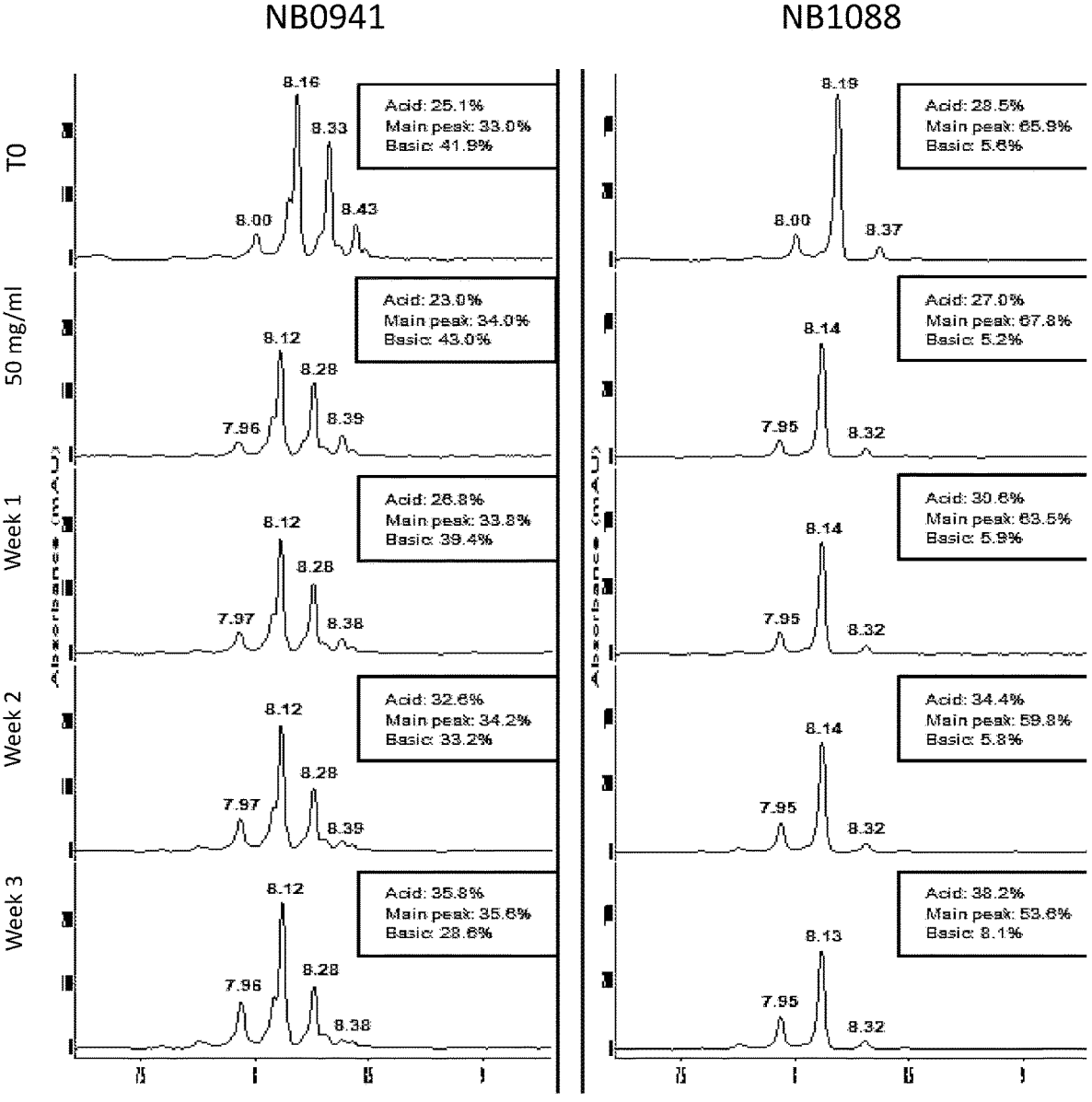

To select a lead candidate, the expression levels after transient expression in HEK 293 EBNA cells, and similarity to human germline sequence were considered (FIG. 6). FIG. 6A summarizes the titers of all variants after transient transfection. Variant VH4/Vk2 showed the highest expression titers and possesses a high percentage of sequence identity with human germ line genes (FIG. 6B). Finally, a producibility assessment of VH4/Vk2 variant (NB1088) was performed in comparison to a variant identical to NB1088, but with the original, deamidation competent LC CDR2 of 5B9 (WASSRHNG) termed NB0941. The biophysical properties of NB0941 and NB1088 were determined. As shown in FIGS. 7A and 7B, high pH stress and incubation at 40° C. revealed changes in the capillary isoelectric focusing (cIEF), specifically an increase in the percent of acid species, possibly due to deamidation. These changes were more pronounced in NB0941 compared to NB1088. Therefore, NB1088 with optimized immunogenicity, expression and binding profile as well as desirable biophysical properties was chosen as the lead humanized variant for functional analysis.

The decrease in affinity, observed in some of the variants, is particularly advantageous in designing CAR driver, given the fact that normal tissues express PVR at minimal levels. The results (FIG. 16) indicate that PVR is overexpressed in variety of tumors, allowing for efficient targeting of these tumors by PVR driven CAR-T. The potential safety concern can be easily addressed by the affinity "tuned down" anti-PVR variants as described in Liu et al. (Cancer research, 2015; Volume 75, Issue 17).

Example 6—NB1088 Inhibits Binding of PVR to TIGIT, CD96 and CD226

Figure 8A:
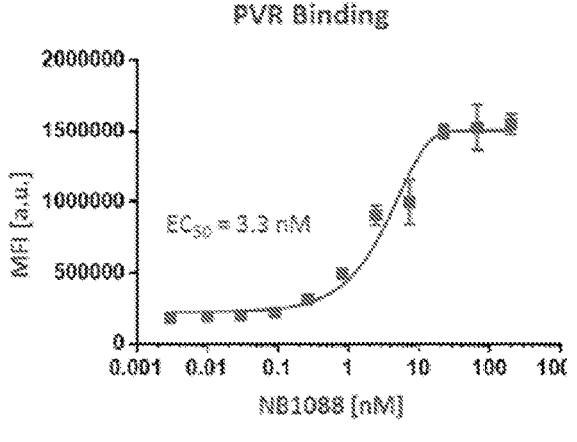
FIGS. 8A-8D illustrate the $EC_{50}$ of NB1088 binding to PVR (FIG. 8A); $IC_{50}$ of NB1088 inhibition of PVR-TIGIT binding (FIG. 8B); $IC_{50}$ of NB1088 inhibition of PVR-CD96 binding (FIG. 8C); and $IC_{50}$ of NB1088 inhibition of PVR-CD226 binding (FIG. 8D).
Figure 8B:
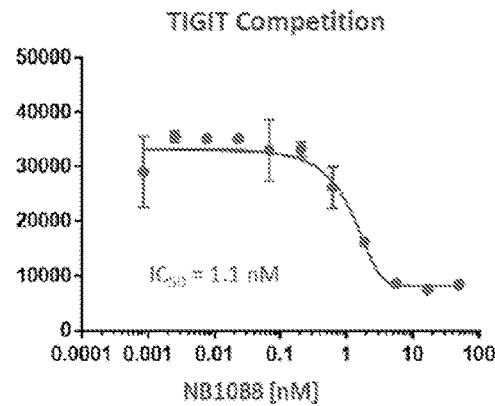
Figure 8C:
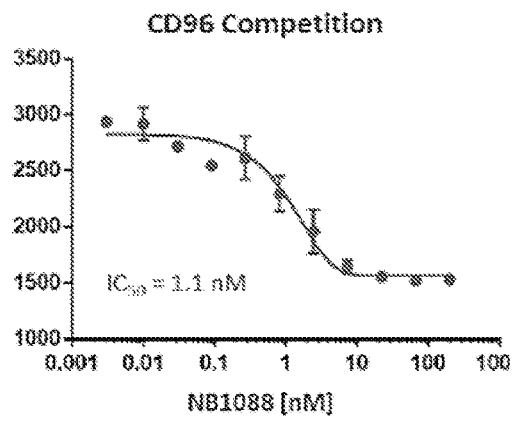
Figure 8D:
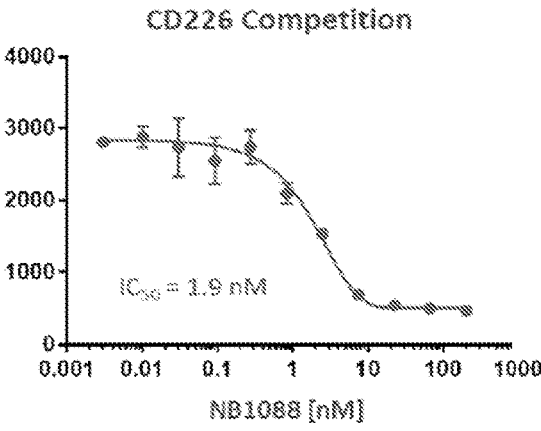

NB1088 was tested for its ability to block TIGIT, CD96, and CD226 binding to PVR. Dissociated CHO cells (Chinese Hamster Ovary) stably expressing human PVR were incubated with NB1088 at the indicated concentrations for 20 minutes on ice followed by addition of biotinylated recombinant TIGIT, CD96 or CD226-Fc, respectively, at 10 ug/ml for an additional 120 minutes on ice. After washing, surface bound NB1088 was detected with anti-human Alexa-488 conjugated secondary antibody and biotinylated proteins were detected with Alexa647 conjugated Streptavidin and analyzed by flow cytometry. FIG. 8A shows that NB1088 binds to PVR with an $EC_{50}$ of about 3.3 nanomolar. The $IC_{50}$ for NB1088 to compete with TIGIT, CD96, or CD226 for PVR binding is 1.1, 1.1 and 1.9 nM respectively, as shown in FIGS. 8B to 8D.

Example 7—NB1088 Stimulates Cytotoxic T and NK Cells

Figure 9A:
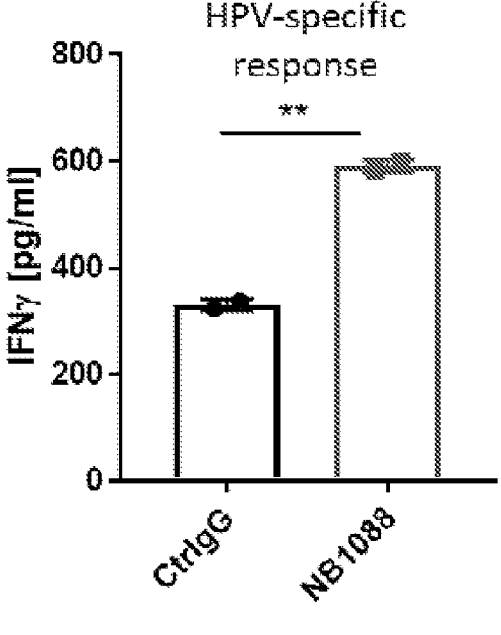
FIGS. 9A-9B illustrate that NB1088 alone (FIGS. 9A and 9B) and in combination with PD1 inhibition by pembrolizumab (FIG. 9B) increases interferon gamma release in a tumor/T cell coculture system using an antigen specific T cell assay (human papillomavirus; HPV) (FIG. 9A) or a non-specific allogenic T cell assay (FIG. 9B). **p<0.01 one-way Anova.
Figure 9B:
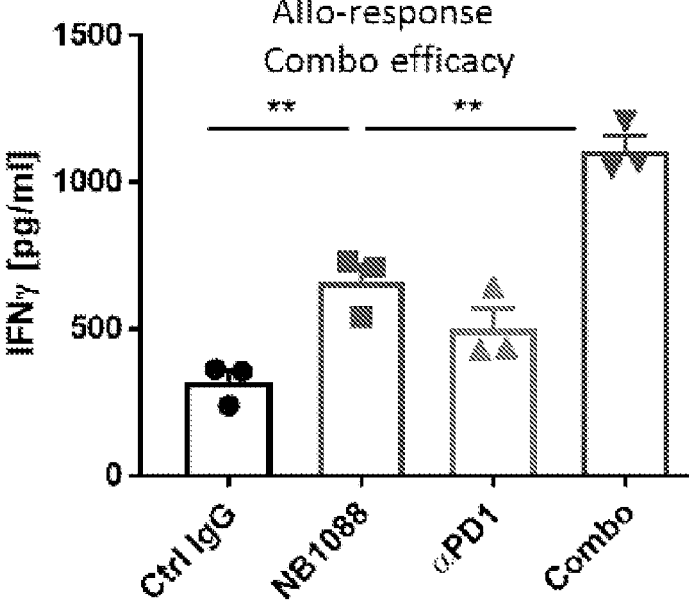

The ability of NB1088 to stimulate T and NK cell activity in vitro was determined. Using an antigen-specific human papillomavirus (HPV) assay, 30,000 HPV+ human cervical epidermoid carcinoma cell line (CaSki cells) and 30,000 HPV-specific CD8 T-cells were co-incubated with control IgG or NB1088 at 10 ug/ml overnight. Interferon gamma release into the supernatant was detected using a human interferon gamma specific MSD system. As shown in FIG. 9A, NB1088 increased the interferon gamma release from human, HPV-specific CD8+ (cytotoxic) T cells when incubated with HPV+ CaSki cells. To test CD8 T-cell activity in an allogenic system, PBMCs were preactivated for three days with Phytohemagglutinin (PHA) and Interleukin 2 (IL2), rested overnight in the absence of PHA/IL2 before isolating CD8 T-cells using a magnetic, negative isolation procedure. 10,000 A549 tumor cells and 100,000 healthy donor CD8+ T cells were co-cultured overnight in the presence of 100 U/ml IL2 and 1 ug/ml anti-CD28 antibody. As shown in FIG. 9B, NB1088 increased interferon gamma release from CD8+ T cells to a greater extent than anti-PD-1 (pembrolizumab), which was further increased as a result of the combination of the NB1088 and the anti-PD-1 antibody.

The effect of NB1088 on antibody dependent cell cytotoxicity (ADCC) was also determined. NK cells from healthy donors were isolated from PBMCs rested overnight using a magnetic, negative isolation procedure. 10,000 PVR+ and EGFR+A549 tumor cells and 50,000 NK cells were either incubated with control IgG; control IgG and the anti-EGFR antibody cetuximab (5 ug/mL); or cetuximab and NB1088. Activity of NK cells to mediate antibody dependent cytotoxicity or interferon gamma release was determined with Cell Titer Glow by analyzing viability of adherent A549 after co-culture and removal of NK-cells, or by MSD analysis of supernatants as above. As shown in FIG. 10A and FIG. 10B, NB1088 when incubated with cetuximab was able to increase the NK-cell mediated killing of A549 cells as well as interferon gamma release.

Example 8—NB1088 Restores CD226 Expression and Activity on CD8 T and NK Cells The ability of NB1088 to affect the function of CD226 was determined. CD226 (DNAM-1) is a cell-surface glycoprotein receptor, expressed by NK and T cells, that serves as a ligand for PVR and aides in tumor killing by CD8+ T and NK cells. In its function, it is opposed by TIGIT and CD96, which are inhibitory molecules expressed on T and NK cells. Thus, an increase in CD226 function due to NB1088 would indicate that NB1088 would enhance T and NK cell activity and have broad anti-tumor activity. The impact of NB1088 on CD226 expression and function was tested in antigen specific and allogenic co-culture systems as described above. As shown in FIGS. 11A and 11B, co-culture of CD8 T cells and NK cells with PVR+ target cells led to a strong reduction in CD226 surface expression on CD8 T cells and NK cells. NB1088 restored cell surface expression of CD226 on CD8 T cells or NK cells, regardless of co-culture system (FIGS. 11A and B) whereas anti-TIGIT did not. The functional consequence of increased CD226 expression on T and NK cells following NB1088 treatment was evaluated using the antigen specific and allogenic coculture systems described above with slight modifications (FIGS. 12A and B). Increased CD226 expression correlated with significantly higher levels of interferon gamma release following NB1088 treatment compared to control IgG or anti-TIGIT treatment (FIGS. 12A and B). Superior T and NK cell activity with NB1088 treatment was at least partially mediated via CD226 activity. Anti-CD226 (DX11, 20 ug/ml) reduced NB1088-dependent interferon gamma release by both allo- and antigen-stimulated CD8 T cells (FIG. 12A) and NK cells following A549 co-culture (FIG. 12B) to levels observed with anti-TIGIT. These data demonstrate that NB1088 improves T and NK cell activity over TIGIT blockade by increasing CD226 expression and/or function.

Example 9—NB1088 Monotherapy Efficacy in Humanized Mouse Tumor Xenograft Models The ability of NB1088 to kill tumors in a humanized mouse model, either A549 (lung adenocarcinoma) or HPAF (pancreatic) was determined. Briefly, $5 \times 10^6$ tumor cells (either A549 or HPAF) were mixed with activated human peripheral blood mononuclear cells at a 1:1 ratio in matrigel and implanted subcutaneously into the flank of immunodeficient NOD/SCID mice (12 animals per condition). As shown in FIGS. 13A and 13B, NB1088 was able to reduce tumor volume at least as well as the anti-PD-1 antibody pembrolizumab. NB1088 was also able to reduce tumor volume in the A549/PBMC model (FIG. 13C), but not with A549 cells alone (FIG. 13D). In the A549/PBMC model, reduced tumor volume correlated with increased CD226 expression on CD8 T cells isolated from NB1088-treated tumors. (FIG. 13E). The effects of NB1088 on CD8 T cell effector function ex vivo was also assessed (FIGS. 14A and B). Digested single cell suspensions from tumors were stimulated with anti-CD28/anti-CD3 in the presence of Brefeldin A and anti-CD107a for 5 hrs at 37° C. Following stimulation, cells were stained to detect production of interferon gamma by CD8+ T cells using flow cytometry by standard surface/intracellular staining methods. As shown in FIGS. 14A and 14B, NB1088 increased the frequency of total interferon gamma positive (FIG. 14A) and polyfunctional interferon gamma/CD107a double positive (FIG. 14B) tumor derived CD8 T-cells. Furthermore, the increased frequency of interferon gamma positive CD8+ T cells in NB1088 treated tumors were derived exclusively from CD226 positive CD8+ T-cells (FIGS. 14C and 14D), suggesting an important in vivo contribution of CD226 function to the anti-tumor activity of NB1088.

Example 10—NB1088 Pharmacokinetics and Pharmacodynamic Changes in CD226 Expression on CD4 T Cells in Cynomolgus Monkey The pharmacokinetic properties of NB1088 was measured following a single or 4×1 weekly IV bolus injections at 2, 50 or 200 mg/kg dose levels in cynomolgus monkey (2 female monkeys/dose group). In addition, changes in CD226 expression on circulating peripheral CD4 T cells was evaluated. FIG. 15A shows the plasma concentrations (ug/ml) of NB1088 as a function of time (hours) and dose. IC90 and 10×IC90 were calculated based on in vitro potency assays using cynomolgus monkey PBMC assay. NB1088 shows a typical PK profile and reached concentrations above 10×IC90 for the duration of the study following repeat dosing at 200 mg/kg dose level. FIG. 15B shows CD226 expression levels on circulating CD4 T-cells normalized to pre-dose, as measured by flow cytometry with specific antibodies. NB1088 increased CD226 surface expression levels up to 1.5-fold in the 50 mg/kg dose group and 200 mg/kg repeat dose group and remained elevated in the 200 mg/kg repeat dose group. These data indicate that NB1088 can engage and modulate CD226 expression on CD4 T cells in cynomolgus monkey.

Example 11—Expression of Human PVR across Different Tumor Types

The expression levels of PVR in human cancer of different origin was evaluated. PVR expression was detected by standard immunohistochemistry procedures using the commercially available rabbit monoclonal antibody clone D3G7H and cancer tissue microarrays. Staining was digitized and intensities were quantified to calculate H-scores within and across indications. FIG. 16 shows elevated expression levels of PVR in most indications analyzed at varying frequencies. The elevated expression of PVR was shown in liver cancer, colon cancer, adrenal cancer, uterine cancer, testicular cancer, squamous cell lung cancer, stomach cancer, esophagus cancer, ovary cancer, bladder cancer, prostate cancer, Cholangiocarcinoma, skin cancer, HNSCC cancer, breast cancer, pancreatic cancer, non-small cell lung cancer, and melanoma. These data suggest contribution of PVR to tumor progression in multiple indications of human cancer.

Example 12—Designing a Humanized Antibody

Humanized IgG antibodies were designed based on one of the variants having the heavy and light chains VH4 and VK2, respectively. An exemplified VK2 sequence is set forth in SEQ ID NO: 49. Exemplified VH4 sequences for hIgG4 (S241P) is set forth in SEQ ID NO: 50, and for hIgG1 is set forth in SEQ ID NO: 51. Further, exemplary nucleotide sequences optimized for expressing the amino acid sequences in CHO cells were designed as follows: For VK2, nucleotide sequence set forth in SEQ ID NO: 52 or SEQ ID NO: 53. For VH4 of IgG4 nucleotide sequence set forth in SEQ ID NO: 54 or SEQ ID NO: 55.

Example 12—CAR-T Cells Expressing scFv Derived from Humanized Anti-PVR Antibody Variants are Specifically Activated in the Presence of Tumor Cells CAR-T construct were designed based on variants H4K2-NTX-1088C and H3K4-NTX-1034C. The amino acid sequences of the scFv molecules are set forth in SEQ ID Nos: 56 and 57, respectively. Parental Jurkat cells or Jurkat cells overexpressing anti-hPVR CAR-T (40K/well) were incubated with A549 or MDA-231 breast cancer cells (PVR positive) at 1:1 E:T for 24 hours. As shown in FIG. 18, both CAR-T drivers led to secretion of hundreds pg of IL2, while the parental Jurkat cells had no detectable IL2 secreted, in presence of the indicated targets. IL2 secretion was quantified using Biolegend hIL2 (cat 431804) These results suggest that αPVR based CAR-T driver is highly functional in inducing T cells activation in presence of target cells expressing PVR.

To examine the CAR-T tumor cell killing, 200K of A549 or MDA-231 cells were plated in a plate of 12 wells with either CAR-T-PVR variants (NTX-1088C or NTX1034C) at E:T of 0.4 and 0.8 to 1 (based on GFP positivity) respectively in NK media for 72 hours. Tumor cell killing was assessed using the standard CTG protocol (Promega G9241). As shown in FIGS. 19A-19C, both PVR variants exhibited over 2-fold increased killing of MDA-231 cells and 8-fold increased killing of A549 cells compared to activated PBMCs. These findings strongly suggest that the αPVR CAR-T constructs significantly increase the killing of targets expressing PVR.

Example 13—Efficient Hematological Target Cell Killing by αPVR CAR-Ts

CAR-T construct were designed based on variants H4K2-NTX-1088C and H3K4-NTX-1034C. The scFv sequences are set forth in SEQ ID Nos: 56 and 57, respectively.

To examine the CAR-T hematological tumor cell killing, 20K/well of K562 cells were plated in 96 wells plates either alone or with CAR-T-PVR variants (NTX-1088C or NTX1034C) at E:Ts ranging from 3.4 to 0.22 to 1 in RPMI supplemented with 100 IU/IL-2/ml for 18 hours. Tumor cell killing was evaluated by flow cytometry. Both NTX-1034C and NTX-1088C were extremely effective in eliminating the targets at higher E:Ts. A clear advantage in NTX-1088C over NTX-1034C at lower E:Ts is probably due to the moderate levels of PVR expressed on K562. These results suggest that αPVR CAR-T can be effective against hematological tumors that express PVR.

The invention claimed is:

1. A humanized antibody or antigen binding fragment thereof comprising a heavy chain variable region and a light chain variable region, wherein the heavy chain variable region comprises an amino acid sequence identical to a sequence selected from the group consisting of SEQ ID NO: 1, SEQ ID NO: 3, SEQ ID NO: 4, SEQ ID NO: 5 and SEQ ID NO: 6, and wherein the light chain variable region comprises an amino acid sequence identical to a sequence selected from the group consisting of SEQ ID NO: 2, SEQ ID NO: 7, SEQ ID NO: 8 and SEQ ID NO: 9.

2. The humanized antibody or antigen binding fragment thereof of claim 1, wherein the heavy chain variable region comprises the amino acid sequence set forth in SEQ ID NO: 1, and the light chain variable region comprises the amino acid sequence set forth in SEQ ID NO:2.

3. The humanized antibody or antigen binding fragment thereof of claim 1, wherein the humanized antibody or antigen binding fragment thereof is an IgG antibody.

4. The humanized antibody or antigen binding fragment thereof of claim 3, wherein the humanized antibody or antigen binding fragment thereof comprises an IgG4 or IgG1 heavy chain constant region.

5. The humanized antibody or antigen binding fragment thereof according to claim 4, wherein the humanized antibody or antigen binding fragment thereof comprises an IgG4 heavy chain constant region having an alteration of a serine residue substituted for proline at position 228 of said IgG4 heavy chain constant region, wherein the positions are numbered according to Kabat.

6. The humanized antibody or antigen binding fragment thereof of claim 1, wherein the humanized antibody or antigen binding fragment thereof is a Fab, F(ab)$_2$, a single-domain antibody, or a single chain variable fragment (scFv).

7. A single chain variable fragment (scFv) of the humanized antibody according to claim 1, comprising an amino acid sequence selected from SEQ ID NO: 56 and SEQ ID NO: 57.

8. The humanized antibody or antigen binding fragment thereof of claim 1, wherein the humanized antibody inhibits binding of PVR to at least one of TIGIT, CD96, and CD226.

9. A nucleic acid or nucleic acids encoding at least one chain or region of the humanized antibody or antigen binding fragment thereof of claim 1.

10. A cell line comprising the nucleic acid or nucleic acids of claim 9.

11. A chimeric antigen receptor (CAR) comprising a combination of heavy and light chain variable region sequences of the humanized antibody according to claim 1.

12. A pharmaceutical composition comprising the humanized antibody or antigen binding fragment thereof of claim 1, and a pharmaceutically acceptable excipient, carrier, or diluent.

13. A method of increasing surface expression and/or signaling of CD226 in the CD8+ T or NK cells of an individual comprising administering to the individual a therapeutically effective amount of the humanized antibody or antigen binding fragment thereof of claim 1.

14. A method of treating a cancer in an individual afflicted with a cancer comprising administering to the individual a therapeutically effective amount of the humanized antibody or antigen binding fragment thereof of claim 1.

15. A method of treating a cancer in an individual in need thereof, comprising administering to the individual a therapeutically effective amount of the CAR of claim 11.

16. A method of treating a cancer in an individual in need thereof, comprising administering to the individual a therapeutically effective amount of the scFv of claim 7.

17. A pharmaceutical composition comprising the scFv of claim 7, and a pharmaceutically acceptable excipient, carrier, or diluent.

18. A pharmaceutical composition comprising the CAR of claim 11, and a pharmaceutically acceptable excipient, carrier, or diluent.

19. A population of T-cells or NK-cells comprising the CAR of claim 11.

* * * * *

SEQUENCE LISTING

<160> NUMBER OF SEQ ID NOS: 58

<210> SEQ ID NO 1
<211> LENGTH: 119
<212> TYPE: PRT
<213> ORGANISM: Artificial sequence
<220> FEATURE:
<223> OTHER INFORMATION: Amino acids

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Thr Phe Ser Asn Tyr
                20                  25                  30

Trp Ile Glu Trp Val Arg Gln Ala Pro Gly Gln Gly Leu Glu Trp Ile
            35                  40                  45

Gly Glu Ile Phe Pro Gly Ser Gly Arg Ile Asn Phe Asn Glu Lys Phe
        50                  55                  60

Lys Gly Arg Val Thr Phe Thr Ala Asp Thr Ser Ile Ser Thr Thr Tyr
65                  70                  75                  80

Met Glu Leu Ser Arg Leu Arg Ser Asp Asp Thr Ala Val Tyr Tyr Cys
                85                  90                  95

Ala Arg Thr Lys Ile Tyr Gly Asn Ser Phe Asp Tyr Trp Gly Gln Gly
                100                 105                 110

Thr Leu Val Thr Val Ser Ser
            115

<210> SEQ ID NO 2
<211> LENGTH: 107
<212> TYPE: PRT
<213> ORGANISM: Artificial sequence
<220> FEATURE:
<223> OTHER INFORMATION: Amino acids

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
                20                  25                  30

Val Val Trp Tyr Gln Gln Lys Pro Gly Lys Ala Pro Lys Leu Leu Ile
            35                  40                  45

Tyr Trp Ala Ser Ser Arg His Glu Gly Val Pro Asp Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Ser Arg Tyr Pro Leu
                85                  90                  95

Thr Phe Gly Gln Gly Thr Lys Leu Glu Ile Lys
                100                 105

<210> SEQ ID NO 3
<211> LENGTH: 119
<212> TYPE: PRT
<213> ORGANISM: Artificial sequence
<220> FEATURE:
<223> OTHER INFORMATION: Amino acids

<400> SEQUENCE: 3

Gln Val Gln Leu Val Gln Ser Gly Ala Glu Leu Lys Lys Pro Gly Ala
1               5                   10                  15

-continued

---

```
Ser Val Lys Ile Ser Cys Lys Ala Thr Gly Tyr Thr Phe Ser Asn Tyr
        20                  25                  30

Trp Ile Glu Trp Ile Lys Gln Ala Pro Gly Gln Gly Leu Glu Trp Ile
        35                  40                  45

Gly Glu Ile Phe Pro Gly Ser Gly Arg Ile Asn Phe Asn Glu Lys Phe
    50                  55                  60

Lys Gly Arg Ala Thr Phe Thr Ala Asp Thr Ser Ile Asp Thr Thr Tyr
65                  70                  75                  80

Met Gln Leu Ser Ser Leu Thr Ser Asp Asp Ser Ala Val Tyr Tyr Cys
                85                  90                  95

Ala Arg Thr Lys Ile Tyr Gly Asn Ser Phe Asp Tyr Trp Gly Gln Gly
            100                 105                 110

Thr Thr Val Thr Val Ser Ser
            115

<210> SEQ ID NO 4
<211> LENGTH: 119
<212> TYPE: PRT
<213> ORGANISM: Artificial sequence
<220> FEATURE:
<223> OTHER INFORMATION: Amino acids

<400> SEQUENCE: 4

Gln Val Gln Leu Val Gln Ser Gly Ala Glu Val Lys Lys Pro Gly Ala
1               5                   10                  15

Ser Val Lys Ile Ser Cys Lys Ala Thr Gly Tyr Thr Phe Ser Asn Tyr
        20                  25                  30

Trp Ile Glu Trp Ile Lys Gln Ala Pro Gly Gln Gly Leu Glu Trp Ile
        35                  40                  45

Gly Glu Ile Phe Pro Gly Ser Gly Arg Ile Asn Phe Asn Glu Lys Phe
    50                  55                  60

Lys Gly Arg Ala Thr Phe Thr Ala Asp Thr Ser Ile Asp Thr Thr Tyr
65                  70                  75                  80

Met Glu Leu Ser Arg Leu Arg Ser Asp Asp Thr Ala Val Tyr Tyr Cys
                85                  90                  95

Ala Arg Thr Lys Ile Tyr Gly Asn Ser Phe Asp Tyr Trp Gly Gln Gly
            100                 105                 110

Thr Leu Val Thr Val Ser Ser
            115

<210> SEQ ID NO 5
<211> LENGTH: 119
<212> TYPE: PRT
<213> ORGANISM: Artificial sequence
<220> FEATURE:
<223> OTHER INFORMATION: Amino acids

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Thr Phe Ser Asn Tyr
        20                  25                  30

Trp Ile Glu Trp Ile Lys Gln Ala Pro Gly Gln Gly Leu Glu Trp Ile
        35                  40                  45

Gly Glu Ile Phe Pro Gly Ser Gly Arg Ile Asn Phe Asn Glu Lys Phe
    50                  55                  60

Lys Gly Arg Val Thr Phe Thr Ala Asp Thr Ser Ile Ser Thr Thr Tyr
```

-continued

```
65                    70                    75                    80

Met Glu Leu Ser Arg Leu Arg Ser Asp Asp Thr Ala Val Tyr Tyr Cys
                    85                    90                    95

Ala Arg Thr Lys Ile Tyr Gly Asn Ser Phe Asp Tyr Trp Gly Gln Gly
                100                   105                   110

Thr Leu Val Thr Val Ser Ser
        115

<210> SEQ ID NO 6
<211> LENGTH: 119
<212> TYPE: PRT
<213> ORGANISM: Artificial sequence
<220> FEATURE:
<223> OTHER INFORMATION: Amino acids

<400> SEQUENCE: 6

Gln Val Gln Leu Val Gln Ser Gly Ala Glu Val Lys Lys Pro Gly Ala
1                   5                    10                   15

Ser Val Lys Val Ser Cys Lys Ala Thr Gly Tyr Thr Phe Ser Asn Tyr
                20                    25                    30

Trp Ile Glu Trp Val Arg Gln Ala Pro Gly Gln Gly Leu Glu Trp Met
            35                    40                    45

Gly Glu Ile Phe Pro Gly Ser Gly Arg Ile Asn Phe Asn Glu Lys Phe
        50                    55                    60

Lys Gly Arg Val Thr Phe Thr Ala Asp Thr Ser Ile Ser Thr Ala Tyr
65                    70                    75                    80

Met Glu Leu Ser Arg Leu Arg Ser Asp Asp Thr Ala Val Tyr Tyr Cys
                    85                    90                    95

Ala Arg Thr Lys Ile Tyr Gly Asn Ser Phe Asp Tyr Trp Gly Gln Gly
                100                   105                   110

Thr Leu Val Thr Val Ser Ser
        115

<210> SEQ ID NO 7
<211> LENGTH: 107
<212> TYPE: PRT
<213> ORGANISM: Artificial sequence
<220> FEATURE:
<223> OTHER INFORMATION: Amino acids

<400> SEQUENCE: 7

Asp Ile Met Met Thr Gln Ser Pro Ser Phe Leu Ser Ala Ser Val Gly
1                   5                    10                   15

Asp Arg Val Thr Ile Thr Cys Lys Ala Ser Gln Asp Val Gly Thr Ala
                20                    25                    30

Val Val Trp Tyr Gln Gln Lys Pro Gly Lys Ala Pro Lys Leu Leu Ile
            35                    40                    45

Tyr Trp Ala Ser Ser Arg His Glu Gly Val Pro Asp Arg Phe Thr Gly
        50                    55                    60

Ser Gly Ser Gly Thr Asp Phe Thr Leu Thr Ile Ser Ser Leu Gln Ser
65                    70                    75                    80

Glu Asp Phe Ala Asp Tyr Phe Cys Gln Gln Tyr Ser Arg Tyr Pro Leu
                    85                    90                    95

Thr Phe Gly Gln Gly Thr Lys Leu Glu Ile Lys
                100                   105

<210> SEQ ID NO 8
<211> LENGTH: 107
```

-continued

```
<212> TYPE: PRT
<213> ORGANISM: Artificial sequence
<220> FEATURE:
<223> OTHER INFORMATION: Amino acids

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Thr Ala
            20                  25                  30

Val Val Trp Tyr Gln Gln Lys Pro Gly Lys Ala Pro Lys Leu Leu Ile
        35                  40                  45

Tyr Trp Ala Ser Ser Arg His Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: Artificial sequence
<220> FEATURE:
<223> OTHER INFORMATION: Amino acids

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Thr Ala
            20                  25                  30

Val Ala Trp Tyr Gln Gln Lys Pro Gly Lys Ala Pro Lys Ser Leu Ile
        35                  40                  45

Tyr Trp Ala Ser Ser Arg His Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 10
<211> LENGTH: 5
<212> TYPE: PRT
<213> ORGANISM: Artificial sequence
<220> FEATURE:
<223> OTHER INFORMATION: Amino acids

<400> SEQUENCE: 10

Asn Tyr Trp Ile Glu
1               5

<210> SEQ ID NO 11
<211> LENGTH: 17
<212> TYPE: PRT
<213> ORGANISM: Artificial sequence
<220> FEATURE:
<223> OTHER INFORMATION: Amino acids
```

<400> SEQUENCE: 11

Glu Ile Phe Pro Gly Ser Gly Arg Ile Asn Phe Asn Glu Lys Phe Lys
1               5                   10                  15

Gly

<210> SEQ ID NO 12
<211> LENGTH: 10
<212> TYPE: PRT
<213> ORGANISM: Artificial sequence
<220> FEATURE:
<223> OTHER INFORMATION: Amino acids

<400> SEQUENCE: 12

Thr Lys Ile Tyr Gly Asn Ser Phe Asp Tyr
1               5                   10

<210> SEQ ID NO 13
<211> LENGTH: 11
<212> TYPE: PRT
<213> ORGANISM: Artificial sequence
<220> FEATURE:
<223> OTHER INFORMATION: Amino acids
<220> FEATURE:
<221> NAME/KEY: MISC_FEATURE
<222> LOCATION: (1)..(1)
<223> OTHER INFORMATION: X=K or R
<220> FEATURE:
<221> NAME/KEY: MISC_FEATURE
<222> LOCATION: (11)..(11)
<223> OTHER INFORMATION: X=V or A

<400> SEQUENCE: 13

Xaa Ala Ser Gln Asp Val Gly Thr Ala Val Xaa
1               5                   10

<210> SEQ ID NO 14
<211> LENGTH: 7
<212> TYPE: PRT
<213> ORGANISM: Artificial sequence
<220> FEATURE:
<223> OTHER INFORMATION: Amino acids

<400> SEQUENCE: 14

Trp Ala Ser Ser Arg His Glu
1               5

<210> SEQ ID NO 15
<211> LENGTH: 9
<212> TYPE: PRT
<213> ORGANISM: Artificial sequence
<220> FEATURE:
<223> OTHER INFORMATION: Amino acids

<400> SEQUENCE: 15

Gln Gln Tyr Ser Arg Tyr Pro Leu Thr
1               5

<210> SEQ ID NO 16
<211> LENGTH: 119
<212> TYPE: PRT
<213> ORGANISM: Mus musculus

<400> SEQUENCE: 16

Gln Val Gln Leu Gln Gln Ser Gly Ala Glu Leu Met Lys Pro Gly Ala
1               5                   10                  15

-continued

```
Ser Val Lys Ile Ser Cys Lys Ala Thr Gly Tyr Thr Phe Ser Asn Tyr
            20                  25                  30

Trp Ile Glu Trp Ile Lys Gln Arg Pro Gly His Gly Leu Glu Trp Ile
            35                  40                  45

Gly Glu Ile Phe Pro Gly Ser Gly Arg Ile Asn Phe Asn Glu Lys Phe
            50                  55                  60

Lys Gly Lys Ala Thr Phe Thr Ala Asp Thr Ser Ser Asp Thr Thr Tyr
65                  70                  75                  80

Met Gln Leu Ser Ser Leu Thr Ser Ala Asp Ser Ala Val Tyr Tyr Cys
                    85                  90                  95

Ala Arg Thr Lys Ile Tyr Gly Asn Ser Phe Asp Tyr Trp Gly Gln Gly
            100                 105                 110

Thr Thr Leu Thr Val Ser Pro
            115

<210> SEQ ID NO 17
<211> LENGTH: 107
<212> TYPE: PRT
<213> ORGANISM: Mus musculus

<400> SEQUENCE: 17

Asp Ile Met Met Thr Gln Ser His Lys Phe Met Ser Thr Ser Val Gly
1               5                   10                  15

Asp Arg Val Asn Ile Thr Cys Lys Ala Ser Gln Asp Val Gly Thr Ala
            20                  25                  30

Val Val Trp Tyr Gln Gln Lys Pro Gly Gln Ser Pro Lys Leu Leu Ile
            35                  40                  45

Tyr Trp Ala Ser Ser Arg His Asn Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Arg Tyr Pro Leu
                    85                  90                  95

Thr Phe Gly Ala Gly Thr Lys Leu Glu Leu Lys
            100                 105

<210> SEQ ID NO 18
<211> LENGTH: 30
<212> TYPE: PRT
<213> ORGANISM: Artificial sequence
<220> FEATURE:
<223> OTHER INFORMATION: Amino acids

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Thr Phe Ser
            20                  25                  30

<210> SEQ ID NO 19
<211> LENGTH: 14
<212> TYPE: PRT
<213> ORGANISM: Artificial sequence
<220> FEATURE:
<223> OTHER INFORMATION: Amino acids

<400> SEQUENCE: 19

Trp Val Arg Gln Ala Pro Gly Gln Gly Leu Glu Trp Ile Gly
1               5                   10
```

-continued

```
<210> SEQ ID NO 20
<211> LENGTH: 32
<212> TYPE: PRT
<213> ORGANISM: Artificial sequence
<220> FEATURE:
<223> OTHER INFORMATION: Amino acids

<400> SEQUENCE: 20

Arg Val Thr Phe Thr Ala Asp Thr Ser Ile Ser Thr Thr Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 21
<211> LENGTH: 11
<212> TYPE: PRT
<213> ORGANISM: Artificial sequence
<220> FEATURE:
<223> OTHER INFORMATION: Amino acids

<400> SEQUENCE: 21

Trp Gly Gln Gly Thr Leu Val Thr Val Ser Ser
1               5                   10

<210> SEQ ID NO 22
<211> LENGTH: 30
<212> TYPE: PRT
<213> ORGANISM: Artificial sequence
<220> FEATURE:
<223> OTHER INFORMATION: Amino acids

<400> SEQUENCE: 22

Gln Val Gln Leu Val Gln Ser Gly Ala Glu Leu Lys Lys Pro Gly Ala
1               5                   10                  15

Ser Val Lys Ile Ser Cys Lys Ala Thr Gly Tyr Thr Phe Ser
            20                  25                  30

<210> SEQ ID NO 23
<211> LENGTH: 14
<212> TYPE: PRT
<213> ORGANISM: Artificial sequence
<220> FEATURE:
<223> OTHER INFORMATION: Amino acids

<400> SEQUENCE: 23

Trp Ile Lys Gln Ala Pro Gly Gln Gly Leu Glu Trp Ile Gly
1               5                   10

<210> SEQ ID NO 24
<211> LENGTH: 32
<212> TYPE: PRT
<213> ORGANISM: Artificial seuence
<220> FEATURE:
<223> OTHER INFORMATION: Amino acids

<400> SEQUENCE: 24

Arg Ala Thr Phe Thr Ala Asp Thr Ser Ile Asp Thr Thr Tyr Met Gln
1               5                   10                  15

Leu Ser Ser Leu Thr Ser Asp Asp Ser Ala Val Tyr Tyr Cys Ala Arg
            20                  25                  30

<210> SEQ ID NO 25
<211> LENGTH: 11
<212> TYPE: PRT
<213> ORGANISM: Artificial sequence
```

```
<220> FEATURE:
<223> OTHER INFORMATION: Amino acids

<400> SEQUENCE: 25

Trp Gly Gln Gly Thr Thr Val Thr Val Ser Ser
1               5                   10

<210> SEQ ID NO 26
<211> LENGTH: 30
<212> TYPE: PRT
<213> ORGANISM: Artificial sequence
<220> FEATURE:
<223> OTHER INFORMATION: Amino acids

<400> SEQUENCE: 26

Gln Val Gln Leu Val Gln Ser Gly Ala Glu Val Lys Lys Pro Gly Ala
1               5                   10                  15

Ser Val Lys Ile Ser Cys Lys Ala Thr Gly Tyr Thr Phe Ser
            20                  25                  30

<210> SEQ ID NO 27
<211> LENGTH: 32
<212> TYPE: PRT
<213> ORGANISM: Artificial sequence
<220> FEATURE:
<223> OTHER INFORMATION: Amino acids

<400> SEQUENCE: 27

Arg Ala Thr Phe Thr Ala Asp Thr Ser Ile Asp Thr Thr Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 28
<211> LENGTH: 14
<212> TYPE: PRT
<213> ORGANISM: Artificial sequence
<220> FEATURE:
<223> OTHER INFORMATION: Amino acids

<400> SEQUENCE: 28

Trp Val Arg Gln Ala Pro Gly Gln Gly Leu Glu Trp Met Gly
1               5                   10

<210> SEQ ID NO 29
<211> LENGTH: 32
<212> TYPE: PRT
<213> ORGANISM: Artificial sequence
<220> FEATURE:
<223> OTHER INFORMATION: Amino acids

<400> SEQUENCE: 29

Arg Val Thr Phe Thr Ala Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 30
<211> LENGTH: 23
<212> TYPE: PRT
<213> ORGANISM: Artificial sequence
<220> FEATURE:
<223> OTHER INFORMATION: Amino acids

<400> SEQUENCE: 30
```

```
Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 31
<211> LENGTH: 15
<212> TYPE: PRT
<213> ORGANISM: Artificial sequence
<220> FEATURE:
<223> OTHER INFORMATION: Amino acids

<400> SEQUENCE: 31

Trp Tyr Gln Gln Lys Pro Gly Lys Ala Pro Lys Leu Leu Ile Tyr
1               5                   10                  15

<210> SEQ ID NO 32
<211> LENGTH: 32
<212> TYPE: PRT
<213> ORGANISM: Artificial sequence
<220> FEATURE:
<223> OTHER INFORMATION: Amino acids

<400> SEQUENCE: 32

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Asp Tyr Phe Cys
            20                  25                  30

<210> SEQ ID NO 33
<211> LENGTH: 10
<212> TYPE: PRT
<213> ORGANISM: Artificial sequence
<220> FEATURE:
<223> OTHER INFORMATION: Amino acids

<400> SEQUENCE: 33

Phe Gly Gln Gly Thr Lys Leu Glu Ile Lys
1               5                   10

<210> SEQ ID NO 34
<211> LENGTH: 23
<212> TYPE: PRT
<213> ORGANISM: Artificial sequence
<220> FEATURE:
<223> OTHER INFORMATION: Amino acids

<400> SEQUENCE: 34

Asp Ile Met Met Thr Gln Ser Pro Ser Phe Leu Ser Ala Ser Val Gly
1               5                   10                  15

Asp Arg Val Thr Ile Thr Cys
            20

<210> SEQ ID NO 35
<211> LENGTH: 32
<212> TYPE: PRT
<213> ORGANISM: Artificial sequence
<220> FEATURE:
<223> OTHER INFORMATION: Amino acids

<400> SEQUENCE: 35

Gly Val Pro Asp Arg Phe Thr Gly Ser Gly Ser Gly Thr Asp Phe Thr
1               5                   10                  15

Leu Thr Ile Ser Ser Leu Gln Ser Glu Asp Phe Ala Asp Tyr Phe Cys
            20                  25                  30
```

```
<210> SEQ ID NO 36
<211> LENGTH: 32
<212> TYPE: PRT
<213> ORGANISM: Artificial sequence
<220> FEATURE:
<223> OTHER INFORMATION: Amino acids

<400> SEQUENCE: 36

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
                20                  25                  30

<210> SEQ ID NO 37
<211> LENGTH: 15
<212> TYPE: PRT
<213> ORGANISM: Artificial sequence
<220> FEATURE:
<223> OTHER INFORMATION: Amino acids

<400> SEQUENCE: 37

Trp Tyr Gln Gln Lys Pro Gly Lys Ala Pro Lys Ser Leu Ile Tyr
1               5                   10                  15

<210> SEQ ID NO 38
<211> LENGTH: 357
<212> TYPE: DNA
<213> ORGANISM: Artificial sequence
<220> FEATURE:
<223> OTHER INFORMATION: Nucleic acid

<400> SEQUENCE: 38
caggtgcagc tggtgcagag cggcgcggaa ctgaaaaaac cgggcgcgag cgtgaaaatt      60
agctgcaaag cgaccggcta tacctttagc aactattgga ttgaatggat taaacaggcg     120
ccgggccagg gcctggaatg gattggcgaa attttttccgg gcagcggccg cattaacttt    180
aacgaaaaat ttaaaggccg cgcgaccttt accgcggata ccagcattga taccacctat     240
atgcagctga gcagcctgac cagcgatgat agcgcggtgt attattgcgc gcgcaccaaa     300
atttatggca acagctttga ttattggggc cagggcacca ccgtgaccgt gagcagc        357

<210> SEQ ID NO 39
<211> LENGTH: 357
<212> TYPE: DNA
<213> ORGANISM: Artificial sequence
<220> FEATURE:
<223> OTHER INFORMATION: Nucleic acid

<400> SEQUENCE: 39
caggtgcagc tggtgcagag cggcgcggaa gtgaaaaaac cgggcgcgag cgtgaaaatt      60
agctgcaaag cgaccggcta tacctttagc aactattgga ttgaatggat taaacaggcg     120
ccgggccagg gcctggaatg gattggcgaa attttttccgg gcagcggccg cattaacttt    180
aacgaaaaat ttaaaggccg cgcgaccttt accgcggata ccagcattga taccacctat     240
atggaactga gccgcctgcg cagcgatgat accgcggtgt attattgcgc gcgcaccaaa     300
atttatggca acagctttga ttattggggc cagggcaccc tggtgaccgt gagcagc        357

<210> SEQ ID NO 40
<211> LENGTH: 357
<212> TYPE: DNA
<213> ORGANISM: Artificial sequence
```

<220> FEATURE:
<223> OTHER INFORMATION: Nucleic acid

<400> SEQUENCE: 40
caggtgcagc tggtgcagag cggcgcggaa gtgaaaaaac cgggcgcgag cgtgaaagtg      60
agctgcaaag cgaccggcta tacctttagc aactattgga ttgaatggat taaacaggcg     120
ccgggccagg gcctggaatg gattggcgaa atttttccgg gcagcggccg cattaacttt     180
aacgaaaaat ttaaaggccg cgtgaccttt accgcggata ccagcattag caccacctat     240
atggaactga gccgcctgcg cagcgatgat accgcggtgt attattgcgc gcgcaccaaa     300
atttatggca acagctttga ttattggggc cagggcaccc tggtgaccgt gagcagc       357

<210> SEQ ID NO 41
<211> LENGTH: 357
<212> TYPE: DNA
<213> ORGANISM: Artificial sequence
<220> FEATURE:
<223> OTHER INFORMATION: Nucleic acid

<400> SEQUENCE: 41
caggtgcagc tggtgcagag cggcgcggaa gtgaaaaaac cgggcgcgag cgtgaaagtg      60
agctgcaaag cgaccggcta tacctttagc aactattgga ttgaatgggt gcgccaggcg     120
ccgggccagg gcctggaatg gattggcgaa atttttccgg gcagcggccg cattaacttt     180
aacgaaaaat ttaaaggccg cgtgaccttt accgcggata ccagcattag caccacctat     240
atggaactga gccgcctgcg cagcgatgat accgcggtgt attattgcgc gcgcaccaaa     300
atttatggca acagctttga ttattggggc cagggcaccc tggtgaccgt gagcagc       357

<210> SEQ ID NO 42
<211> LENGTH: 357
<212> TYPE: DNA
<213> ORGANISM: Artificial sequence
<220> FEATURE:
<223> OTHER INFORMATION: Nucleic acid

<400> SEQUENCE: 42
caggtgcagc tggtgcagag cggcgcggaa gtgaaaaaac cgggcgcgag cgtgaaagtg      60
agctgcaaag cgaccggcta tacctttagc aactattgga ttgaatgggt gcgccaggcg     120
ccgggccagg gcctggaatg gatgggcgaa atttttccgg gcagcggccg cattaacttt     180
aacgaaaaat ttaaaggccg cgtgaccttt accgcggata ccagcattag caccgcgtat     240
atggaactga gccgcctgcg cagcgatgat accgcggtgt attattgcgc gcgcaccaaa     300
atttatggca acagctttga ttattggggc cagggcaccc tggtgaccgt gagcagc       357

<210> SEQ ID NO 43
<211> LENGTH: 321
<212> TYPE: DNA
<213> ORGANISM: Artificial sequence
<220> FEATURE:
<223> OTHER INFORMATION: Nucleic acid

<400> SEQUENCE: 43
gatattatga tgacccagag cccgagcttt ctgagcgcga gcgtgggcga tcgcgtgacc      60
attacctgca aagcgagcca ggatgtgggc accgcggtgg tgtggtatca gcagaaaccg     120
ggcaaagcgc cgaaactgct gatttattgg gcgagcagcc gccatgaagg cgtgccggat     180
cgctttaccg gcagcggcag cggcaccgat tttaccctga ccattagcag cctgcagagc     240

```
gaagattttg cggattattt ttgccagcag tatagccgct atccgctgac ctttggccag       300
ggcaccaaac tggaaattaa a                                                 321

<210> SEQ ID NO 44
<211> LENGTH: 321
<212> TYPE: DNA
<213> ORGANISM: Artificial sequence
<220> FEATURE:
<223> OTHER INFORMATION: Nucleic acid

<400> SEQUENCE: 44
gatattcaga tgacccagag cccgagcagc ctgagcgcga gcgtgggcga tcgcgtgacc        60
attacctgca aagcgagcca ggatgtgggc accgcggtgg tgtggtatca gcagaaaccg       120
ggcaaagcgc cgaaactgct gatttattgg gcgagcagcc gccatgaagg cgtgccggat       180
cgctttagcg gcagcggcag cggcaccgat tttaccctga ccattagcag cctgcagccg       240
gaagattttg cggattattt ttgccagcag tatagccgct atccgctgac ctttggccag       300
ggcaccaaac tggaaattaa a                                                 321

<210> SEQ ID NO 45
<211> LENGTH: 321
<212> TYPE: DNA
<213> ORGANISM: Artificial sequence
<220> FEATURE:
<223> OTHER INFORMATION: Nucleic acid

<400> SEQUENCE: 45
gatattcaga tgacccagag cccgagcagc ctgagcgcga gcgtgggcga tcgcgtgacc        60
attacctgcc gcgcgagcca ggatgtgggc accgcggtgg tgtggtatca gcagaaaccg       120
ggcaaagcgc cgaaactgct gatttattgg gcgagcagcc gccatgaagg cgtgccgagc       180
cgctttagcg gcagcggcag cggcaccgat tttaccctga ccattagcag cctgcagccg       240
gaagattttg cgacctattt ttgccagcag tatagccgct atccgctgac ctttggccag       300
ggcaccaaac tggaaattaa a                                                 321

<210> SEQ ID NO 46
<211> LENGTH: 321
<212> TYPE: DNA
<213> ORGANISM: Artificial sequence
<220> FEATURE:
<223> OTHER INFORMATION: Nucleic acid

<400> SEQUENCE: 46
gatattcaga tgacccagag cccgagcagc ctgagcgcga gcgtgggcga tcgcgtgacc        60
attacctgcc gcgcgagcca ggatgtgggc accgcggtgg cgtggtatca gcagaaaccg       120
ggcaaagcgc cgaaaagcct gatttattgg gcgagcagcc gccatgaagg cgtgccgagc       180
cgctttagcg gcagcggcag cggcaccgat tttaccctga ccattagcag cctgcagccg       240
gaagattttg cgacctattt ttgccagcag tatagccgct atccgctgac ctttggccag       300
ggcaccaaac tggaaattaa a                                                 321

<210> SEQ ID NO 47
<211> LENGTH: 119
<212> TYPE: PRT
<213> ORGANISM: Artificial seuence
<220> FEATURE:
<223> OTHER INFORMATION: Amino acids
<220> FEATURE:
<221> NAME/KEY: MISC_FEATURE
```

```
<222> LOCATION: (11)..(11)
<223> OTHER INFORMATION: X=L or V
<220> FEATURE:
<221> NAME/KEY: MISC_FEATURE
<222> LOCATION: (20)..(20)
<223> OTHER INFORMATION: X=I or V
<220> FEATURE:
<221> NAME/KEY: MISC_FEATURE
<222> LOCATION: (37)..(37)
<223> OTHER INFORMATION: X=I or V
<220> FEATURE:
<221> NAME/KEY: MISC_FEATURE
<222> LOCATION: (38)..(38)
<223> OTHER INFORMATION: X=K or R
<220> FEATURE:
<221> NAME/KEY: MISC_FEATURE
<222> LOCATION: (48)..(48)
<223> OTHER INFORMATION: X=I or M
<220> FEATURE:
<221> NAME/KEY: MISC_FEATURE
<222> LOCATION: (68)..(68)
<223> OTHER INFORMATION: X=A or V
<220> FEATURE:
<221> NAME/KEY: MISC_FEATURE
<222> LOCATION: (77)..(77)
<223> OTHER INFORMATION: X=D or S
<220> FEATURE:
<221> NAME/KEY: MISC_FEATURE
<222> LOCATION: (79)..(79)
<223> OTHER INFORMATION: X=T or A
<220> FEATURE:
<221> NAME/KEY: MISC_FEATURE
<222> LOCATION: (82)..(82)
<223> OTHER INFORMATION: X=Q or E
<220> FEATURE:
<221> NAME/KEY: MISC_FEATURE
<222> LOCATION: (85)..(85)
<223> OTHER INFORMATION: X=S or R
<220> FEATURE:
<221> NAME/KEY: MISC_FEATURE
<222> LOCATION: (87)..(87)
<223> OTHER INFORMATION: X=T or R
<220> FEATURE:
<221> NAME/KEY: MISC_FEATURE
<222> LOCATION: (91)..(91)
<223> OTHER INFORMATION: X=S or T
<220> FEATURE:
<221> NAME/KEY: MISC_FEATURE
<222> LOCATION: (114)..(114)
<223> OTHER INFORMATION: X=T or L

<400> SEQUENCE: 47

Gln Val Gln Leu Val Gln Ser Gly Ala Glu Xaa Lys Lys Pro Gly Ala
1               5                   10                  15

Ser Val Lys Xaa Ser Cys Lys Ala Thr Gly Tyr Thr Phe Ser Asn Tyr
            20                  25                  30

Trp Ile Glu Trp Xaa Xaa Gln Ala Pro Gly Gln Gly Leu Glu Trp Xaa
        35                  40                  45

Gly Glu Ile Phe Pro Gly Ser Gly Arg Ile Asn Phe Asn Glu Lys Phe
    50                  55                  60

Lys Gly Arg Xaa Thr Phe Thr Ala Asp Thr Ser Ile Xaa Thr Xaa Tyr
65                  70                  75                  80

Met Xaa Leu Ser Xaa Leu Xaa Ser Asp Asp Xaa Ala Val Tyr Tyr Cys
                85                  90                  95

Ala Arg Thr Lys Ile Tyr Gly Asn Ser Phe Asp Tyr Trp Gly Gln Gly
            100                 105                 110

Thr Xaa Val Thr Val Ser Ser
        115

<210> SEQ ID NO 48
```

```
<211> LENGTH: 107
<212> TYPE: PRT
<213> ORGANISM: Artificial sequence
<220> FEATURE:
<223> OTHER INFORMATION: Amino acids
<220> FEATURE:
<221> NAME/KEY: MISC_FEATURE
<222> LOCATION: (3)..(3)
<223> OTHER INFORMATION: X=M or Q
<220> FEATURE:
<221> NAME/KEY: MISC_FEATURE
<222> LOCATION: (10)..(10)
<223> OTHER INFORMATION: X=F or S
<220> FEATURE:
<221> NAME/KEY: MISC_FEATURE
<222> LOCATION: (24)..(24)
<223> OTHER INFORMATION: X=K or R
<220> FEATURE:
<221> NAME/KEY: MISC_FEATURE
<222> LOCATION: (34)..(34)
<223> OTHER INFORMATION: X=V or A
<220> FEATURE:
<221> NAME/KEY: MISC_FEATURE
<222> LOCATION: (46)..(46)
<223> OTHER INFORMATION: X=L or S
<220> FEATURE:
<221> NAME/KEY: MISC_FEATURE
<222> LOCATION: (60)..(60)
<223> OTHER INFORMATION: X=D or S
<220> FEATURE:
<221> NAME/KEY: MISC_FEATURE
<222> LOCATION: (63)..(63)
<223> OTHER INFORMATION: X=T or S
<220> FEATURE:
<221> NAME/KEY: MISC_FEATURE
<222> LOCATION: (80)..(80)
<223> OTHER INFORMATION: X=S or P
<220> FEATURE:
<221> NAME/KEY: MISC_FEATURE
<222> LOCATION: (85)..(85)
<223> OTHER INFORMATION: X=D or T

<400> SEQUENCE: 48

Asp Ile Xaa Met Thr Gln Ser Pro Ser Xaa Leu Ser Ala Ser Val Gly
1               5                   10                  15

Asp Arg Val Thr Ile Thr Cys Xaa Ala Ser Gln Asp Val Gly Thr Ala
            20                  25                  30

Val Xaa Trp Tyr Gln Gln Lys Pro Gly Lys Ala Pro Lys Xaa Leu Ile
        35                  40                  45

Tyr Trp Ala Ser Ser Arg His Glu Gly Val Pro Xaa Arg Phe Xaa Gly
    50                  55                  60

Ser Gly Ser Gly Thr Asp Phe Thr Leu Thr Ile Ser Ser Leu Gln Xaa
65                  70                  75                  80

Glu Asp Phe Ala Xaa Tyr Phe Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 49
<211> LENGTH: 236
<212> TYPE: PRT
<213> ORGANISM: Artificial sequence
<220> FEATURE:
<223> OTHER INFORMATION: Amino acids

<400> SEQUENCE: 49

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
```

-continued

```
           20                25                30
Leu Ser Ala Ser Val Gly Asp Arg Val Thr Ile Thr Cys Lys Ala Ser
       35                40                45
Gln Asp Val Gly Thr Ala Val Val Trp Tyr Gln Gln Lys Pro Gly Lys
   50                55                60
Ala Pro Lys Leu Leu Ile Tyr Trp Ala Ser Ser Arg His Glu Gly Val
65                70                75                80
Pro Asp Arg Phe Ser Gly Ser Gly Ser Gly Thr Asp Phe Thr Leu Thr
               85                90                95
Ile Ser Ser Leu Gln Pro Glu Asp Phe Ala Asp Tyr Phe Cys Gln Gln
           100               105               110
Tyr Ser Arg Tyr Pro Leu Thr Phe Gly Gln Gly Thr Lys Leu Glu Ile
       115               120               125
Lys Arg Thr Val Ala Ala Pro Ser Val Phe Ile Phe Pro Pro Ser Asp
   130               135               140
Glu Gln Leu Lys Ser Gly Thr Ala Ser Val Val Cys Leu Leu Asn Asn
145               150               155               160
Phe Tyr Pro Arg Glu Ala Lys Val Gln Trp Lys Val Asp Asn Ala Leu
               165               170               175
Gln Ser Gly Asn Ser Gln Glu Ser Val Thr Glu Gln Asp Ser Lys Asp
           180               185               190
Ser Thr Tyr Ser Leu Ser Ser Thr Leu Thr Leu Ser Lys Ala Asp Tyr
       195               200               205
Glu Lys His Lys Val Tyr Ala Cys Glu Val Thr His Gln Gly Leu Ser
   210               215               220
Ser Pro Val Thr Lys Ser Phe Asn Arg Gly Glu Cys
225               230               235

<210> SEQ ID NO 50
<211> LENGTH: 446
<212> TYPE: PRT
<213> ORGANISM: Artificial sequence
<220> FEATURE:
<223> OTHER INFORMATION: Amino acids

<400> SEQUENCE: 50

Gln Val Gln Leu Val Gln Ser Gly Ala Glu Val Lys Lys Pro Gly Ala
1               5                10                15
Ser Val Lys Val Ser Cys Lys Ala Thr Gly Tyr Thr Phe Ser Asn Tyr
               20                25                30
Trp Ile Glu Trp Val Arg Gln Ala Pro Gly Gln Gly Leu Glu Trp Ile
       35                40                45
Gly Glu Ile Phe Pro Gly Ser Gly Arg Ile Asn Phe Asn Glu Lys Phe
   50                55                60
Lys Gly Arg Val Thr Phe Thr Ala Asp Thr Ser Ile Ser Thr Thr Tyr
65                70                75                80
Met Glu Leu Ser Arg Leu Arg Ser Asp Asp Thr Ala Val Tyr Tyr Cys
               85                90                95
Ala Arg Thr Lys Ile Tyr Gly Asn Ser Phe Asp Tyr Trp Gly Gln Gly
           100               105               110
Thr Leu Val Thr Val Ser Ser Ala Ser Thr Lys Gly Pro Ser Val Phe
       115               120               125
Pro Leu Ala Pro Cys Ser Arg Ser Thr Ser Glu Ser Thr Ala Ala Leu
   130               135               140
Gly Cys Leu Val Lys Asp Tyr Phe Pro Glu Pro Val Thr Val Ser Trp
```

-continued

```
145                    150                    155                    160

Asn Ser Gly Ala Leu Thr Ser Gly Val His Thr Phe Pro Ala Val Leu
                165                    170                    175

Gln Ser Ser Gly Leu Tyr Ser Leu Ser Ser Val Val Thr Val Pro Ser
                180                    185                    190

Ser Ser Leu Gly Thr Lys Thr Tyr Thr Cys Asn Val Asp His Lys Pro
                195                    200                    205

Ser Asn Thr Lys Val Asp Lys Arg Val Glu Ser Lys Tyr Gly Pro Pro
                210                    215                    220

Cys Pro Pro Cys Pro Ala Pro Glu Phe Leu Gly Gly Pro Ser Val Phe
225                    230                    235                    240

Leu Phe Pro Pro Lys Pro Lys Asp Thr Leu Met Ile Ser Arg Thr Pro
                245                    250                    255

Glu Val Thr Cys Val Val Val Asp Val Ser Gln Glu Asp Pro Glu Val
                260                    265                    270

Gln Phe Asn Trp Tyr Val Asp Gly Val Glu Val His Asn Ala Lys Thr
                275                    280                    285

Lys Pro Arg Glu Glu Gln Phe Asn Ser Thr Tyr Arg Val Val Ser Val
                290                    295                    300

Leu Thr Val Leu His Gln Asp Trp Leu Asn Gly Lys Glu Tyr Lys Cys
305                    310                    315                    320

Lys Val Ser Asn Lys Gly Leu Pro Ser Ser Ile Glu Lys Thr Ile Ser
                325                    330                    335

Lys Ala Lys Gly Gln Pro Arg Glu Pro Gln Val Tyr Thr Leu Pro Pro
                340                    345                    350

Ser Gln Glu Glu Met Thr Lys Asn Gln Val Ser Leu Thr Cys Leu Val
                355                    360                    365

Lys Gly Phe Tyr Pro Ser Asp Ile Ala Val Glu Trp Glu Ser Asn Gly
                370                    375                    380

Gln Pro Glu Asn Asn Tyr Lys Thr Thr Pro Pro Val Leu Asp Ser Asp
385                    390                    395                    400

Gly Ser Phe Phe Leu Tyr Ser Arg Leu Thr Val Asp Lys Ser Arg Trp
                405                    410                    415

Gln Glu Gly Asn Val Phe Ser Cys Ser Val Met His Glu Ala Leu His
                420                    425                    430

Asn His Tyr Thr Gln Lys Ser Leu Ser Leu Ser Leu Gly Lys
                435                    440                    445

<210> SEQ ID NO 51
<211> LENGTH: 449
<212> TYPE: PRT
<213> ORGANISM: Artificial sequence
<220> FEATURE:
<223> OTHER INFORMATION: Amino acids

<400> SEQUENCE: 51

Gln Val Gln Leu Val Gln Ser Gly Ala Glu Val Lys Lys Pro Gly Ala
1               5                      10                     15

Ser Val Lys Val Ser Cys Lys Ala Thr Gly Tyr Thr Phe Ser Asn Tyr
                20                     25                     30

Trp Ile Glu Trp Val Arg Gln Ala Pro Gly Gln Gly Leu Glu Trp Ile
                35                     40                     45

Gly Glu Ile Phe Pro Gly Ser Gly Arg Ile Asn Phe Asn Glu Lys Phe
                50                     55                     60

Lys Gly Arg Val Thr Phe Thr Ala Asp Thr Ser Ile Ser Thr Thr Tyr
```

-continued

```
            65                    70                    75                    80
Met Glu Leu Ser Arg Leu Arg Ser Asp Asp Thr Ala Val Tyr Tyr Cys
                85                    90                    95

Ala Arg Thr Lys Ile Tyr Gly Asn Ser Phe Asp Tyr Trp Gly Gln Gly
                100                   105                   110

Thr Leu Val Thr Val Ser Ser Ala Ser Thr Lys Gly Pro Ser Val Phe
                115                   120                   125

Pro Leu Ala Pro Ser Ser Lys Ser Thr Ser Gly Gly Thr Ala Ala Leu
        130                   135                   140

Gly Cys Leu Val Lys Asp Tyr Phe Pro Glu Pro Val Thr Val Ser Trp
145                   150                   155                   160

Asn Ser Gly Ala Leu Thr Ser Gly Val His Thr Phe Pro Ala Val Leu
                165                   170                   175

Gln Ser Ser Gly Leu Tyr Ser Leu Ser Ser Val Val Thr Val Pro Ser
                180                   185                   190

Ser Ser Leu Gly Thr Gln Thr Tyr Ile Cys Asn Val Asn His Lys Pro
                195                   200                   205

Ser Asn Thr Lys Val Asp Lys Lys Val Glu Pro Lys Ser Cys Asp Lys
        210                   215                   220

Thr His Thr Cys Pro Pro Cys Pro Ala Pro Glu Leu Leu Gly Gly Pro
225                   230                   235                   240

Ser Val Phe Leu Phe Pro Pro Lys Pro Lys Asp Thr Leu Met Ile Ser
                245                   250                   255

Arg Thr Pro Glu Val Thr Cys Val Val Val Asp Val Ser His Glu Asp
                260                   265                   270

Pro Glu Val Lys Phe Asn Trp Tyr Val Asp Gly Val Glu Val His Asn
                275                   280                   285

Ala Lys Thr Lys Pro Arg Glu Glu Gln Tyr Asn Ser Thr Tyr Arg Val
        290                   295                   300

Val Ser Val Leu Thr Val Leu His Gln Asp Trp Leu Asn Gly Lys Glu
305                   310                   315                   320

Tyr Lys Cys Lys Val Ser Asn Lys Ala Leu Pro Ala Pro Ile Glu Lys
                325                   330                   335

Thr Ile Ser Lys Ala Lys Gly Gln Pro Arg Glu Pro Gln Val Tyr Thr
                340                   345                   350

Leu Pro Pro Ser Arg Asp Glu Leu Thr Lys Asn Gln Val Ser Leu Thr
                355                   360                   365

Cys Leu Val Lys Gly Phe Tyr Pro Ser Asp Ile Ala Val Glu Trp Glu
        370                   375                   380

Ser Asn Gly Gln Pro Glu Asn Asn Tyr Lys Thr Thr Pro Pro Val Leu
385                   390                   395                   400

Asp Ser Asp Gly Ser Phe Phe Leu Tyr Ser Lys Leu Thr Val Asp Lys
                405                   410                   415

Ser Arg Trp Gln Gln Gly Asn Val Phe Ser Cys Ser Val Met His Glu
                420                   425                   430

Ala Leu His Asn His Tyr Thr Gln Lys Ser Leu Ser Leu Ser Pro Gly
                435                   440                   445

Lys
```

<210> SEQ ID NO 52
<211> LENGTH: 711
<212> TYPE: DNA
<213> ORGANISM: Artificial sequence
<220> FEATURE:

<223> OTHER INFORMATION: Nucleic acid

<400> SEQUENCE: 52

```
atggacatga gggtccccgc tcagctcctg gggctcctgc tactctggct ccgaggtgcc      60
agatgtgaca tccagatgac ccagtcccct tcctctttat ccgcttccgt gggcgatagg     120
gtgaccatca cttgtaaggc ctcccaagat gtgggcacag ctgtggtgtg gtaccagcag     180
aagcccggca aggcccccaa gctgctgatc tactgggctt cctctcgtca cgagggcgtg     240
cccgatcgtt tctccggctc cggatccggc accgacttca ctttaaccat ctcctcttta     300
cagcccgagg acttcgccga ctacttctgc cagcagtact ctcgttaccc tttaaccttt     360
ggccaaggta ccaagctgga gatcaagcgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac     540 tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgttg a              711
```

<210> SEQ ID NO 53
<211> LENGTH: 718
<212> TYPE: DNA
<213> ORGANISM: Artificial sequence
<220> FEATURE:
<223> OTHER INFORMATION: Nucleic acid

<400> SEQUENCE: 53

```
atggacatga gagtgcctgc tcagctgctg ggactgctgc tgttgtggtt gagaggcgcc      60
agatgcgaca tccagatgac ccagtctcca tcctctctgt ccgcctctgt gggcgacaga     120
gtgaccatca catgcaaggc ctctcaggat gtgggcaccg ccgttgtgtg gtatcagcag     180
aagcctggca aggcccctaa gctgctgatc tactgggcct cctctagaca cgagggcgtg     240
cccgatagat tctccggctc tggctctggc accgacttta ccctgacaat ctccagcctg     300
cagcctgagg acttcgccga ctacttctgc cagcagtaca gcagataccc tctgaccttt     360
ggccagggca ccaagctgga aatcaagcgt acggtggccg ctcccagcgt gttcatcttc     420
cccccaagcg acgagcagct gaagagcggc accgccagcg tggtgtgtct gctgaacaac     480
ttctacccca gggaggccaa ggtgcagtgg aaggtggaca cgccctgca gagcggcaac     540 agccaggaga gcgtcaccga gcaggacagc aaggactcca cctacagcct gagcagcacc     600
ctgaccctga gcaaggccga ctacgagaag cacaaggtgt acgcctgtga ggtgacccac     660
cagggcctgt ccagccccgt gaccaagagc ttcaacaggg gcgagtgctg atgaattc      718
```

<210> SEQ ID NO 54
<211> LENGTH: 1398
<212> TYPE: DNA
<213> ORGANISM: Artificial sequence
<220> FEATURE:
<223> OTHER INFORMATION: Nucleic acid

<400> SEQUENCE: 54

```
atggggtcaa ccgccatcct ggcctcctc ctggctgttc tccaaggagt ctgtgcccaa      60
gttcagctgg tgcagagcgg cgctgaggtg aagaagcccg gtgcctccgt gaaggtgtct     120
tgtaaggcca ccggctacac cttctccaac tactggatcg agtgggtgag gcaagctccc     180
ggtcaaggtt tagagtggat cggagagatc ttccccggct ccgccggat caacttcaac     240
```

-continued

```
gagaagttca agggccgggt gacctttacc gccgacacca gcatctccac cacctacatg      300
gagctgtctc gtctgaggtc cgacgacacc gccgtgtact actgcgctcg taccaagatc      360
tacggcaact ccttcgacta ctggggccaa ggtactttag tgacagtgtc ctccgctagc      420
accaagggcc catccgtctt ccccctggcg ccctgctcca ggagcacctc cgagagcaca      480
gccgccctgg gctgcctggt caaggactac ttccccgaac cggtgacggt gtcgtggaac      540
tcaggcgccc tgaccagcgg cgtgcacacc ttccccggctg tcctacagtc ctcaggactc      600
tactccctca gcagcgtggt gaccgtgccc tccagcagct tgggcacgaa gacctacacc      660
tgcaacgtag atcacaagcc cagcaacacc aaggtggaca agagagttga gtccaaatat      720
ggtcccccat gcccaccatg cccagcacct gagttcctgg ggggaccatc agtcttcctg      780 ttcccccaa aacccaagga cactctcatg atctcccgga cccctgaggt cacgtgcgtg      840
gtggtggacg tgagccagga agaccccgag gtccagttca actggtacgt ggatggcgtg      900
gaggtgcata atgccaagac aaagccgcgg gaggagcagt tcaacagcac gtaccgtgtg      960
gtcagcgtcc tcaccgtcct gcaccaggac tggctgaacg gcaaggagta caagtgcaag     1020
gtctccaaca aaggcctccc gtcctccatc gagaaaacca tctccaaagc caaagggcag     1080
ccccgagagc cacaggtgta caccctgccc ccatcccagg aggagatgac caagaaccag     1140
gtcagcctga cctgcctggt caaaggcttc tacccccagcg acatcgccgt ggagtgggag     1200
agcaatgggc agccggagaa caactacaag accacgcctc ccgtgctgga ctccgacggc     1260
tccttcttcc tctacagcag gctaaccgtg gacaagagca ggtggcagga ggggaatgtc     1320
ttctcatgct ccgtgatgca tgaggctctg cacaaccact acacacagaa gagcctctcc     1380
ctgtctctgg gtaaatga                                                    1398
```

<210> SEQ ID NO 55
<211> LENGTH: 1402
<212> TYPE: DNA
<213> ORGANISM: Artificial sequence
<220> FEATURE:
<223> OTHER INFORMATION: Nucleic acid

<400> SEQUENCE: 55

```
atgggctcta cagctatcct gggactgctg ctggctgtgc tgcaaggcgt ttgtgctcag       60
gtgcagctgg ttcagtctgg cgccgaagtg aagaaacctg gcgcctctgt gaaggtgtcc      120
tgcaaggcta ccggctacac cttctccaac tactggatcg agtgggtccg acaggctcct      180
ggacaaggcc tggaatggat cggcgagatc tttcctggca gcggccggat caacttcaac      240
gagaagttca agggcagagt gaccttcacc gccgacacct ccatctccac cacctacatg      300
gaactgtccc ggctgagatc tgacgacacc gccgtgtact actgcgcccg gaccaagatc      360
tacggcaact ccttcgatta ctggggccag ggcacactgg tcaccgtgtc ctctgcttct      420
acaaagggcc caagcgtgtt ccccctggcc cctgctcca gaagcaccag cgagagcaca      480
gccgccctgg gctgcctggt gaaggactac ttccccgagc ccgtgaccgt gtcctggaac      540
agcggagccc tgaccagcgg cgtgcacacc ttccccgccg tgctgcagag cagcggcctg      600
tacagcctga gcagcgtggt gaccgtgccc agcagcagcc tgggcaccaa gacctacacc      660
tgtaacgtgg accacaagcc cagcaacacc aaggtggaca gagagggtgga gagcaagtac      720 ggcccaccct gccccccctg cccagccccc gagttcctgg gcggacccag cgtgttcctg      780
ttccccccca agcccaagga caccctgatg atcagcagaa cccccgaggt gacctgtgtg      840
```

-continued

```
gtggtggacg tgtcccagga ggaccccgag gtccagttca actggtacgt ggacggcgtg      900
gaggtgcaca cgccaagac caagcccaga gaggagcagt ttaacagcac ctaccgggtg        960
gtgtccgtgc tgaccgtgct gcaccaggac tggctgaacg gcaaagagta caagtgtaag      1020
gtctccaaca agggcctgcc aagcagcatc gaaaagacca tcagcaaggc caagggccag      1080
cctagagagc cccaggtcta cacctgcca cccagccaag aggagatgac caagaaccag       1140
gtgtccctga cctgtctggt gaagggcttc tacccaagcg acatcgccgt ggagtgggag      1200
agcaacggcc agcccgagaa caactacaag accacccccc cagtgctgga cagcgacggc      1260
agcttcttcc tgtacagcag gctgaccgtg gacaagtcca gatggcagga gggcaacgtc      1320
tttagctgct ccgtgatgca cgaggccctg cacaaccact acacccagaa gagcctgagc      1380
ctgtccctgg gctgatgaat tc                                              1402
```

```
<210> SEQ ID NO 56
<211> LENGTH: 260
<212> TYPE: PRT
<213> ORGANISM: Artificial sequence
<220> FEATURE:
<223> OTHER INFORMATION: Amino acids

<400> SEQUENCE: 56

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Thr Gly Tyr Thr Phe
        35                  40                  45

Ser Asn Tyr Trp Ile Glu Trp Val Arg Gln Ala Pro Gly Gln Gly Leu
    50                  55                  60

Glu Trp Ile Gly Glu Ile Phe Pro Gly Ser Gly Arg Ile Asn Phe Asn
65                  70                  75                  80

Glu Lys Phe Lys Gly Arg Val Thr Phe Thr Ala Asp Thr Ser Ile Ser
                85                  90                  95

Thr Thr Tyr Met Glu Leu Ser Arg Leu Arg Ser Asp Asp Thr Ala Val
            100                 105                 110

Tyr Tyr Cys Ala Arg Thr Lys Ile Tyr Gly Asn Ser Phe Asp Tyr Trp
        115                 120                 125

Gly Gln Gly Thr Leu Val Thr Val Ser Ser Gly Gly Gly Ser Gly
    130                 135                 140

Gly Gly Gly Ser Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Lys Ala Ser Gln Asp Val Gly Thr Ala Val Val Trp Tyr Gln Gln Lys
            180                 185                 190

Pro Gly Lys Ala Pro Lys Leu Leu Ile Tyr Trp Ala Ser Ser Arg His
        195                 200                 205

Glu Gly Val Pro Asp Arg Phe Ser Gly Ser Gly Ser Gly Thr Asp Phe
    210                 215                 220

Thr Leu Thr Ile Ser Ser Leu Gln Pro Glu Asp Phe Ala Asp Tyr Phe
225                 230                 235                 240

Cys Gln Gln Tyr Ser Arg Tyr Pro Leu Thr Phe Gly Gln Gly Thr Lys
                245                 250                 255

Leu Glu Ile Lys
```

-continued

```
                260

<210> SEQ ID NO 57
<211> LENGTH: 260
<212> TYPE: PRT
<213> ORGANISM: Artificial sequence
<220> FEATURE:
<223> OTHER INFORMATION: Amino acids

<400> SEQUENCE: 57

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Thr Gly Tyr Thr Phe
            35                  40                  45

Ser Asn Tyr Trp Ile Glu Trp Ile Lys Gln Ala Pro Gly Gln Gly Leu
        50                  55                  60

Glu Trp Ile Gly Glu Ile Phe Pro Gly Ser Gly Arg Ile Asn Phe Asn
65                  70                  75                  80

Glu Lys Phe Lys Gly Arg Val Thr Phe Thr Ala Asp Thr Ser Ile Ser
                85                  90                  95

Thr Thr Tyr Met Glu Leu Ser Arg Leu Arg Ser Asp Asp Thr Ala Val
                100                 105                 110

Tyr Tyr Cys Ala Arg Thr Lys Ile Tyr Gly Asn Ser Phe Asp Tyr Trp
            115                 120                 125

Gly Gln Gly Thr Leu Val Thr Val Ser Ser Gly Gly Gly Ser Gly
        130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Asp Val Gly Thr Ala Val Ala Trp Tyr Gln Gln Lys
                180                 185                 190

Pro Gly Lys Ala Pro Lys Ser Leu Ile Tyr Trp Ala Ser Ser Arg His
            195                 200                 205

Glu Gly Val Pro Ser Arg Phe Ser Gly Ser Gly Ser Gly Thr Asp Phe
        210                 215                 220

Thr Leu Thr Ile Ser Ser Leu Gln Pro Glu Asp Phe Ala Thr Tyr Phe
225                 230                 235                 240

Cys Gln Gln Tyr Ser Arg Tyr Pro Leu Thr Phe Gly Gln Gly Thr Lys
                245                 250                 255

Leu Glu Ile Lys
            260

<210> SEQ ID NO 58
<211> LENGTH: 10
<212> TYPE: PRT
<213> ORGANISM: Artificial sequence
<220> FEATURE:
<223> OTHER INFORMATION: Amino acids

<400> SEQUENCE: 58

Gly Tyr Thr Phe Ser Asn Tyr Trp Ile Glu
1               5                   10
```